(12) United States Patent
Muni et al.

(10) Patent No.: US 10,441,758 B2
(45) Date of Patent: Oct. 15, 2019

(54) FRONTAL SINUS SPACER

(71) Applicant: Acclarent, Inc., Irvine, CA (US)

(72) Inventors: Ketan P. Muni, San Jose, CA (US);
Hung V. Ha, San Jose, CA (US);
Randy S. Chan, San Jose, CA (US);
Nga K. Van, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 0 days.

(21) Appl. No.: 15/595,319

(22) Filed: May 15, 2017

(65) Prior Publication Data

US 2017/0312485 A1    Nov. 2, 2017

Related U.S. Application Data

(63) Continuation of application No. 14/266,002, filed on Apr. 30, 2014, now Pat. No. 9,649,477, which is a
(Continued)

(51) Int. Cl.
*A61M 25/10* (2013.01)
*A61B 17/24* (2006.01)
(Continued)

(52) U.S. Cl.
CPC .......... *A61M 25/1002* (2013.01); *A61B 17/24* (2013.01); *A61B 17/3417* (2013.01);
(Continued)

(58) Field of Classification Search
CPC .. A61M 25/04; A61M 25/10; A61M 25/1002; A61M 25/10186; A61M 25/104; A61M 2025/0008; A61M 2025/0226; A61M 2025/0293; A61M 2025/0681; A61M 2025/1047; A61M 2025/105;
(Continued)

(56) References Cited

U.S. PATENT DOCUMENTS 446,173 A    2/1891  Hancock
504,424 A    9/1893  De Pezzer
(Continued)

FOREIGN PATENT DOCUMENTS

CA    2013323    9/1990
CH     668188   12/1988
(Continued)

OTHER PUBLICATIONS

U.S. Appl. No. 10/912,557.
(Continued)

*Primary Examiner* — Kami A Bosworth
(74) *Attorney, Agent, or Firm* — Frost Brown Todd LLC

(57) ABSTRACT

Substance delivering spacer devices may comprise expandable reservoirs that are implantable in paranasal sinuses and other cavities, openings and passageways of the body to maintain patency and to provide sustained local delivery of a therapeutic or diagnostic substance. Delivery apparatus including elongate tubular members as well as shapeable distal portions and atraumatic tips are provided. Also provided are sinus penetrator devices and systems for performing ethmoidotomy procedures or for creating other openings in the walls of paranasal sinuses or other anatomical structures.

20 Claims, 41 Drawing Sheets

Related U.S. Application Data continuation of application No. 12/341,602, filed on Dec. 22, 2008, now Pat. No. 8,764,729, which is a continuation-in-part of application No. 12/100,361, filed on Apr. 9, 2008, now Pat. No. 8,864,787, which is a continuation-in-part of application No. 11/544,009, filed on Oct. 4, 2006, now Pat. No. 7,419,497, which is a continuation-in-part of application No. 11/234,395, filed on Sep. 23, 2005, now Pat. No. 7,410,480, which is a continuation-in-part of application No. 11/037,548, filed on Jan. 18, 2005, now Pat. No. 7,462,175, which is a continuation-in-part of application No. 10/912,578, filed on Aug. 4, 2004, now Pat. No. 7,361,168, which is a continuation-in-part of application No. 10/829,917, filed on Apr. 21, 2004, now Pat. No. 7,654,997.

(51) Int. Cl.
| | | |
|---|---|---|
| A61B 17/34 | (2006.01) | |
| A61F 11/00 | (2006.01) | |
| A61M 25/04 | (2006.01) | |
| A61M 25/06 | (2006.01) | |
| A61M 25/00 | (2006.01) | |
| A61M 29/02 | (2006.01) | |
| A61M 25/02 | (2006.01) | |
| A61B 90/00 | (2016.01) | |

(52) U.S. Cl.
CPC ........ *A61B 17/3421* (2013.01); *A61F 11/004* (2013.01); *A61M 25/04* (2013.01); *A61M 25/0662* (2013.01); *A61B 2090/062* (2016.02); *A61M 25/0075* (2013.01); *A61M 25/0084* (2013.01); *A61M 25/10* (2013.01); *A61M 29/02* (2013.01); *A61M 2025/0008* (2013.01); *A61M 2025/0226* (2013.01); *A61M 2025/0681* (2013.01); *A61M 2025/0687* (2013.01); *A61M 2025/105* (2013.01); *A61M 2210/0618* (2013.01)

(58) Field of Classification Search
CPC .. A61M 2025/1054; A61M 2025/1063; A61M 2025/1079; A61M 2025/1081; A61M 2025/1086; A61M 2210/0618; A61M 31/002; A61M 2025/1013; A61M 2029/025

See application file for complete search history.

(56) References Cited

U.S. PATENT DOCUMENTS

| | | | |
|---|---|---|---|
| 513,667 A | 1/1894 | Buckingham | |
| 705,346 A | 7/1902 | Hamilton | |
| 798,775 A | 9/1905 | Forsyte | |
| 816,792 A | 4/1906 | Green | |
| 1,080,934 A | 12/1913 | Shackleford | |
| 1,200,267 A | 10/1916 | Sunnergren | |
| 1,650,959 A | 11/1927 | Pitman | |
| 1,735,519 A | 11/1929 | Vance | |
| 1,828,986 A | 10/1931 | Stevens | |
| 1,878,671 A | 9/1932 | Cantor | |
| 2,201,749 A | 5/1940 | Vandegrift | |
| 2,493,326 A | 1/1950 | Trinder | |
| 2,525,183 A | 10/1950 | Robison | |
| 2,847,997 A | 8/1958 | Tibone | |
| 2,899,227 A | 8/1959 | Jeanrenaud | |
| 2,906,179 A | 9/1959 | Bower | |
| 2,995,832 A | 8/1961 | Alderson | |
| 3,009,265 A | 11/1961 | Bexark | |
| 3,037,286 A | 6/1962 | Bower | |
| 3,173,418 A | 3/1965 | baran | |
| 3,347,061 A | 10/1967 | Stuemky | |
| 3,376,659 A | 4/1968 | Asin et al. | |
| 3,384,970 A | 5/1968 | Avalear | |
| 3,393,073 A | 7/1968 | Reutenauer et al. | |
| 3,435,826 A | 4/1969 | Fogarty | |
| 3,447,061 A | 5/1969 | Russell et al. | |
| 3,469,578 A | 9/1969 | Bierman | |
| 3,481,043 A | 12/1969 | Esch | |
| 3,486,539 A | 12/1969 | Jacuzzi | |
| 3,506,005 A | 4/1970 | Gilio et al. | |
| 3,509,638 A | 5/1970 | Macleod | |
| 3,515,137 A | 6/1970 | Santomieri | |
| 3,515,888 A | 6/1970 | Lewis | |
| 3,527,220 A | 9/1970 | Summers | |
| 3,531,868 A | 10/1970 | Stevenson | |
| 3,552,384 A | 1/1971 | Pierie et al. | |
| 3,624,661 A | 11/1971 | Shebanow | |
| 3,731,963 A | 5/1973 | Pond | |
| 3,766,924 A | 10/1973 | Pidgeon | |
| 3,792,391 A | 2/1974 | Ewing | |
| 3,800,788 A | 4/1974 | White | |
| 3,802,096 A | 4/1974 | Matern | |
| 3,804,081 A | 4/1974 | Kinoshita | |
| 3,834,394 A | 9/1974 | Hunter et al. | |
| 3,847,145 A | 11/1974 | Grossan | |
| 3,850,176 A | 11/1974 | Gottschalk | |
| 3,856,000 A | 12/1974 | Chikama | |
| 3,859,993 A | 1/1975 | Bitner | |
| 3,871,365 A | 3/1975 | Chikama | |
| 3,894,538 A | 7/1975 | Richter | |
| 3,903,893 A | 9/1975 | Scheer | |
| 3,910,617 A | 10/1975 | Scalza et al. | |
| 3,921,636 A | 11/1975 | Zaffaroni | |
| 3,948,254 A | 4/1976 | Zaffaroni | |
| 3,948,262 A | 4/1976 | Zaffaroni | |
| 3,967,618 A | 7/1976 | Zaffaroni | |
| 3,993,069 A | 11/1976 | Buckles et al. | |
| 3,993,072 A | 11/1976 | Zaffaroni | |
| 3,993,073 A | 11/1976 | Zaffaroni | |
| 4,016,251 A | 4/1977 | Higuchi et al. | |
| 4,052,505 A | 10/1977 | Higuchi et al. | |
| 4,053,975 A | 10/1977 | Olbrich et al. | |
| 4,069,307 A | 1/1978 | Higuchi et al. | |
| 4,102,342 A | 7/1978 | Akiyama et al. | |
| 4,138,151 A | 2/1979 | Nakao | |
| 4,184,497 A | 1/1980 | Kolff et al. | |
| 4,198,766 A | 4/1980 | Camin et al. | |
| 4,207,890 A | 6/1980 | Mamajek et al. | |
| 4,209,919 A | 7/1980 | Kirikae et al. | |
| 4,213,095 A | 7/1980 | Falconer | |
| 4,217,898 A | 8/1980 | Theeuwes | |
| 4,268,115 A | 5/1981 | Slemon et al. | |
| 4,299,226 A | 11/1981 | Banka | |
| 4,299,227 A | 11/1981 | Lincoff | |
| 4,311,146 A | 1/1982 | Wonder | |
| 4,312,353 A | 1/1982 | Shahbabian | |
| 4,338,941 A | 7/1982 | Payton | |
| 4,364,392 A * | 12/1982 | Strother ............ A61B 17/0057 604/103.01 |
| D269,204 S | 5/1983 | Trepp | |
| 4,388,941 A | 6/1983 | Riedhammer | |
| RE31,351 E | 8/1983 | Falconer | |
| 4,435,716 A | 3/1984 | Zandbergen | |
| 4,437,856 A | 3/1984 | Valli | |
| 4,441,495 A | 4/1984 | Hicswa | |
| 4,450,150 A | 5/1984 | Sidman | |
| 4,459,977 A | 7/1984 | Pizon et al. | |
| 4,464,175 A | 8/1984 | Altman et al. | |
| 4,471,779 A | 9/1984 | Antoshkiw et al. | |
| 4,499,899 A | 2/1985 | Lyons, III | |
| 4,517,979 A | 5/1985 | Pecenka | |
| 4,554,929 A | 11/1985 | Samson et al. | |
| 4,564,364 A | 1/1986 | Zaffaroni et al. | |
| 4,571,239 A | 2/1986 | Heyman | |
| 4,571,240 A | 2/1986 | Samson et al. | |
| 4,581,017 A | 4/1986 | Sahota | |
| 4,585,000 A | 4/1986 | Hershenson | |
| D283,921 S | 5/1986 | Dyak | |
| 4,589,868 A | 5/1986 | Dretler | |

(56) References Cited

U.S. PATENT DOCUMENTS

| | | |
|---|---|---|
| 4,592,357 A | 6/1986 | Ersek |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,641,654 A | 2/1987 | Samson et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,682,607 A | 7/1987 | Vaillancourt et al. |
| 4,691,948 A | 9/1987 | Austin, Jr. et al. |
| 4,696,544 A | 9/1987 | Costella |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,753,637 A | 6/1988 | Horneffer |
| 4,755,171 A | 7/1988 | Tennant |
| 4,771,776 A | 9/1988 | Powell et al. |
| 4,784,117 A | 11/1988 | Miyazaki |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,834,709 A | 5/1989 | Banning et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,953,553 A | 9/1990 | Tremulis |
| 4,961,433 A | 10/1990 | Christian |
| 4,966,163 A | 10/1990 | Kraus et al. |
| 4,984,581 A | 1/1991 | Stice |
| 4,986,810 A | 1/1991 | Semrad |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,040,548 A | 8/1991 | Yock |
| 5,041,089 A | 8/1991 | Mueller et al. |
| 5,044,678 A | 9/1991 | Detweiler |
| 5,049,132 A | 9/1991 | Shaffer et al. |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Tamauchi et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,099,845 A | 3/1992 | Besz et al. |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Olivier |
| 5,156,595 A | 10/1992 | Adams |
| 5,161,534 A | 11/1992 | Berthiaume |
| 5,163,989 A | 11/1992 | Campbell et al. |
| 5,167,220 A | 12/1992 | Brown |
| 5,168,864 A | 12/1992 | Skockey |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,195,971 A | 3/1993 | Sirhan |
| 5,197,457 A | 3/1993 | Adair |
| 5,207,695 A | 5/1993 | Trout, III |
| 5,211,952 A | 5/1993 | Spicer et al. |
| 5,213,576 A | 5/1993 | Abiuso et al. |
| 5,215,105 A | 6/1993 | Kizelshteyn et al. |
| 5,221,260 A | 6/1993 | Burns et al. |
| 5,221,261 A * | 6/1993 | Termin ............... A61F 2/90 604/104 |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| 5,246,421 A * | 9/1993 | Saab ............... A61M 25/104 128/898 |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deniega |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A | 4/1994 | Yock |
| 5,304,123 A | 4/1994 | Atala et al. |
| 5,306,272 A | 4/1994 | Cohen et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,315,618 A | 5/1994 | Yoshida |
| 5,318,528 A | 6/1994 | Heaven et al. |
| 5,324,306 A | 6/1994 | Makower et al. |
| 5,333,620 A | 8/1994 | Moutafis et al. |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |

(56) References Cited

U.S. PATENT DOCUMENTS

| | | | |
|---|---|---|---|
| 5,341,818 A | | 8/1994 | Abrams et al. |
| 5,342,296 A | | 8/1994 | Persson et al. |
| 5,343,865 A | | 9/1994 | Gardineer et al. |
| 5,345,945 A | | 9/1994 | Hodgson et al. |
| 5,346,075 A | | 9/1994 | Nichols et al. |
| 5,346,508 A | | 9/1994 | Hastings |
| 5,348,537 A | | 9/1994 | Wiesner et al. |
| 5,350,396 A | | 9/1994 | Eliachar |
| 5,356,418 A | | 10/1994 | Shturman |
| 5,368,049 A | | 11/1994 | Raman et al. |
| 5,368,558 A | | 11/1994 | Nita |
| 5,368,566 A | | 11/1994 | Crocker |
| 5,370,640 A | | 12/1994 | Koloff |
| 5,372,138 A | | 12/1994 | Crowley et al. |
| 5,372,584 A | | 12/1994 | Zink et al. |
| D355,031 S | | 1/1995 | Yoshikawa |
| 5,385,562 A | | 1/1995 | Adams et al. |
| 5,386,817 A | | 2/1995 | Jones |
| 5,386,828 A | | 2/1995 | Owens et al. |
| 5,391,147 A | | 2/1995 | Imran et al. |
| 5,391,179 A | | 2/1995 | Mezzoli |
| 5,395,367 A | | 3/1995 | Wilk |
| 5,402,799 A | | 4/1995 | Colon et al. |
| 5,409,444 A | * | 4/1995 | Kensey ............ A61B 17/12109 600/16 |
| 5,411,475 A | | 5/1995 | Atala et al. |
| 5,411,476 A | | 5/1995 | Abrams et al. |
| 5,411,477 A | | 5/1995 | Saab |
| 5,415,633 A | | 5/1995 | Lazarus |
| 5,425,370 A | | 6/1995 | Vilkomerson |
| 5,439,446 A | | 8/1995 | Barry |
| 5,441,494 A | | 8/1995 | Ortiz |
| 5,441,497 A | | 8/1995 | Narciso, Jr. |
| 5,445,646 A | | 8/1995 | Euteneuer et al. |
| 5,450,853 A | | 9/1995 | Hastings et al. |
| 5,451,221 A | | 9/1995 | Cho et al. |
| 5,454,817 A | | 10/1995 | Katz |
| 5,458,572 A | | 10/1995 | Campbell et al. |
| 5,459,700 A | | 10/1995 | Jacobs |
| 5,465,717 A | | 11/1995 | Imran et al. |
| 5,465,733 A | | 11/1995 | Hinohara et al. |
| 5,478,565 A | | 12/1995 | Geria |
| 5,486,181 A | | 1/1996 | Cohen et al. |
| 5,496,338 A | | 3/1996 | Miyagi et al. |
| 5,497,783 A | | 3/1996 | Urick et al. |
| 5,507,301 A | | 4/1996 | Wasicek et al. |
| 5,507,725 A | | 4/1996 | Savage et al. |
| 5,507,766 A | | 4/1996 | Kugo et al. |
| 5,507,795 A | | 4/1996 | Chiang et al. |
| 5,509,900 A | * | 4/1996 | Kirkman ............ A61M 25/0082 604/104 |
| 5,512,055 A | | 4/1996 | Domb et al. |
| 5,514,128 A | | 5/1996 | Hillsman et al. |
| 5,519,532 A | | 5/1996 | Broome |
| 5,531,676 A | | 7/1996 | Edwards et al. |
| 5,533,985 A | | 7/1996 | Wong |
| 5,538,008 A | | 7/1996 | Crowe |
| 5,546,964 A | | 8/1996 | Stangerup |
| 5,549,542 A | | 8/1996 | Kovalcheck |
| 5,558,073 A | | 9/1996 | Pomeranz et al. |
| 5,558,652 A | | 9/1996 | Henke |
| 5,562,619 A | | 10/1996 | Mirarchi et al. |
| 5,568,809 A | | 10/1996 | Ben-Haim |
| 5,571,086 A | | 11/1996 | Kaplan et al. |
| 5,578,007 A | | 11/1996 | Imran |
| 5,578,048 A | | 11/1996 | Pasqualucci et al. |
| 5,582,575 A | | 12/1996 | Heckele et al. |
| 5,584,827 A | | 12/1996 | Korteweg et al. |
| 5,591,194 A | | 1/1997 | Berthiaume |
| 5,599,284 A | | 2/1997 | Shea |
| 5,599,304 A | | 2/1997 | Shaari |
| 5,599,576 A | | 2/1997 | Opolski |
| 5,601,087 A | | 2/1997 | Gunderson et al. |
| 5,601,594 A | | 2/1997 | Best |
| 5,607,386 A | | 3/1997 | Flam |
| 5,617,870 A | | 4/1997 | Hastings et al. |
| 5,626,374 A | | 5/1997 | Kim |
| 5,633,000 A | | 5/1997 | Grossman et al. |
| 5,634,908 A | | 6/1997 | Loomas |
| 5,638,819 A | | 6/1997 | Manwaring et al. |
| 5,643,251 A | | 7/1997 | Hillsman et al. |
| 5,645,789 A | | 7/1997 | Roucher, Jr. |
| 5,647,361 A | | 7/1997 | Damadian |
| 5,653,690 A | | 8/1997 | Booth et al. |
| 5,656,030 A | | 8/1997 | Hunjan et al. |
| 5,662,674 A | | 9/1997 | Debbas |
| 5,664,567 A | | 9/1997 | Linder |
| 5,664,580 A | | 9/1997 | Erickson et al. |
| 5,665,052 A | | 9/1997 | Bullard |
| 5,669,388 A | | 9/1997 | Vilkomerson |
| 5,673,707 A | | 10/1997 | Chandrasekaran |
| 5,676,673 A | | 10/1997 | Ferre et al. |
| 5,679,400 A | | 10/1997 | Tuch |
| 5,682,199 A | | 10/1997 | Lankford |
| 5,685,838 A | | 11/1997 | Peters et al. |
| 5,685,847 A | | 11/1997 | Barry |
| 5,690,373 A | | 11/1997 | Luker |
| 5,693,065 A | | 12/1997 | Rains, III |
| 5,694,945 A | | 12/1997 | Ben-Haim |
| 5,695,468 A | * | 12/1997 | Lafontaine ......... A61M 25/1018 604/96.01 |
| 5,697,159 A | | 12/1997 | Linden |
| 5,700,286 A | | 12/1997 | Tartaglia et al. |
| 5,704,910 A | * | 1/1998 | Humes ................ A61F 2/01 604/502 |
| 5,707,376 A | | 1/1998 | Kavteladze et al. |
| 5,707,389 A | | 1/1998 | Louw et al. |
| 5,708,175 A | | 1/1998 | Loyanagi et al. |
| 5,711,315 A | | 1/1998 | Jerusalmy |
| 5,713,839 A | | 2/1998 | Shea |
| 5,713,946 A | | 2/1998 | Ben-Haim |
| 5,718,702 A | | 2/1998 | Edwards |
| 5,720,300 A | | 2/1998 | Fagan et al. |
| 5,720,719 A | | 2/1998 | Edwards et al. |
| 5,722,401 A | | 3/1998 | Pietroski et al. |
| 5,722,984 A | | 3/1998 | Fischell et al. |
| 5,729,129 A | | 3/1998 | Acker |
| 5,730,128 A | | 3/1998 | Pomeranz et al. |
| 5,733,248 A | | 3/1998 | Adams et al. |
| 5,749,357 A | | 5/1998 | Linder |
| 5,752,513 A | | 5/1998 | Acker et al. |
| 5,752,971 A | | 5/1998 | Rosenbluth et al. |
| 5,762,604 A | | 6/1998 | Kieturakis |
| 5,766,158 A | | 6/1998 | Opolski |
| 5,769,821 A | | 6/1998 | Abrahamson et al. |
| 5,772,639 A | * | 6/1998 | Lampropoulos .. A61M 25/0014 604/264 |
| 5,775,327 A | | 7/1998 | Randolph et al. |
| 5,776,158 A | | 7/1998 | Chou |
| 5,779,699 A | | 7/1998 | Lipson |
| 5,789,391 A | | 8/1998 | Jacobus et al. |
| 5,792,100 A | | 8/1998 | Shantha |
| 5,797,878 A | | 8/1998 | Bleam |
| 5,803,089 A | | 9/1998 | Ferre et al. |
| 5,814,016 A | | 9/1998 | Valley et al. |
| 5,819,723 A | | 10/1998 | Joseph |
| 5,820,568 A | | 10/1998 | Willis |
| 5,820,592 A | | 10/1998 | Hammerslag |
| 5,824,044 A | | 10/1998 | Quiachon et al. |
| 5,824,048 A | | 10/1998 | Tuch |
| 5,824,173 A | | 10/1998 | Fontirroche et al. |
| 5,826,576 A | | 10/1998 | West |
| 5,827,224 A | | 10/1998 | Shippert |
| 5,830,188 A | | 11/1998 | Abouleish |
| 5,833,608 A | | 11/1998 | Acker |
| 5,833,645 A | | 11/1998 | Lieber et al. |
| 5,833,650 A | | 11/1998 | Imran |
| 5,833,682 A | | 11/1998 | Amplatz et al. |
| 5,836,638 A | | 11/1998 | Slocum |
| 5,836,935 A | | 11/1998 | Ashton et al. |
| 5,836,951 A | | 11/1998 | Rosenbluth et al. |
| 5,837,313 A | | 11/1998 | Ding et al. |
| 5,843,089 A | | 12/1998 | Sahatjian et al. |
| 5,843,113 A | | 12/1998 | High |

(56) References Cited

U.S. PATENT DOCUMENTS

| | | |
|---|---|---|
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | Von Hoffmann |
| 5,882,333 A | 3/1999 | Schaer et al. |
| 5,882,346 A | 3/1999 | Pomeranz et al. |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,967,984 A | 10/1999 | Chu et al. |
| 5,968,069 A * | 10/1999 | Dusbabek ............... A61F 2/958 604/96.01 |
| 5,968,085 A | 10/1999 | Morris et al. |
| 5,971,975 A | 10/1999 | Mills et al. |
| 5,976,074 A | 11/1999 | Moriyama |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,987,344 A | 11/1999 | West |
| 5,993,462 A | 11/1999 | Pomeranz et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,022 A | 5/2000 | Ben-Haim |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,776 B1 | 1/2001 | Adams et al. |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,248,092 B1 | 6/2001 | Miraki et al. |
| 6,249,180 B1 | 6/2001 | Maalej et al. |
| 6,254,550 B1 | 7/2001 | McNamara et al. |
| 6,268,574 B1 | 7/2001 | Edens |
| 6,270,477 B1 | 8/2001 | Bagaoisan et al. |
| 6,280,433 B1 | 8/2001 | McIvor et al. |
| 6,283,908 B1 | 9/2001 | Aviram et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,302,875 B1 | 10/2001 | Makower et al. |
| 6,304,768 B1 | 10/2001 | Blume et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,328,730 B1 | 12/2001 | Harkrider, Jr. |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,379,319 B1 | 4/2002 | Garibotto et al. |
| 6,381,485 B1 | 4/2002 | Hunter et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,436,119 B1 | 8/2002 | Erb et al. |
| 6,440,061 B1 | 8/2002 | Wenner et al. |
| 6,443,947 B1 | 9/2002 | Marko et al. |

(56) References Cited

U.S. PATENT DOCUMENTS

| | | |
|---|---|---|
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,485,500 B1 * | 11/2002 | Kokish ............... A61M 25/104 604/101.01 |
| 6,488,653 B1 | 12/2002 | Lombardo |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,511,471 B2 | 1/2003 | Rosenman et al. |
| 6,514,249 B1 | 2/2003 | Maguire et al. |
| 6,517,478 B2 | 2/2003 | Khadem |
| 6,520,954 B2 | 2/2003 | Ouchi |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,223 B1 | 4/2003 | Kokish |
| 6,544,230 B1 | 4/2003 | Flaherty et al. |
| 6,547,804 B2 * | 4/2003 | Porter ............... A61B 17/12113 606/195 |
| 6,549,800 B1 | 4/2003 | Atalar et al. |
| 6,551,239 B2 | 4/2003 | Renner et al. |
| 6,562,022 B2 | 5/2003 | Hoste et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,718 B2 | 7/2003 | Hayzelden et al. |
| 6,585,794 B2 | 7/2003 | Shimoda et al. |
| 6,589,164 B1 | 7/2003 | Flaherty |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,610,059 B1 | 8/2003 | West, Jr. |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B2 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,659,106 B1 | 12/2003 | Hovda et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,833 B2 | 1/2004 | Smith et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,738,656 B1 | 5/2004 | Ferre et al. |
| 6,755,812 B2 | 6/2004 | Peterson et al. |
| 6,758,857 B2 | 7/2004 | Cioanta et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovengo |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,849,062 B2 | 2/2005 | Kantor |
| 6,851,290 B1 | 2/2005 | Meier et al. |
| 6,855,136 B2 | 2/2005 | Dorros et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,979,979 B2 | 12/2005 | Xu et al. |
| 6,984,203 B2 | 1/2006 | Tartaglia et al. |
| 6,989,024 B2 | 1/2006 | Hebert et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,004,176 B2 | 2/2006 | Lau |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,044,964 B2 | 5/2006 | Jang et al. |
| 7,048,711 B2 | 5/2006 | Rosenman et al. |
| 7,052,474 B2 | 5/2006 | Castell et al. |
| 7,056,284 B2 | 6/2006 | Martone et al. |
| 7,056,303 B2 | 6/2006 | Dennis et al. |
| 7,056,314 B1 | 6/2006 | Florio et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,117,039 B2 | 10/2006 | Manning et al. |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |

(56) References Cited

U.S. PATENT DOCUMENTS

| | | | |
|---|---|---|---|
| 7,174,774 B2 | 2/2007 | Pawar et al. |
| 7,182,735 B2 | 2/2007 | Shireman et al. |
| 7,184,827 B1 | 2/2007 | Edwards |
| 7,186,224 B2 | 3/2007 | Windheuser |
| 7,207,981 B2 | 4/2007 | Quinn et al. |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,248,914 B2 | 7/2007 | Hastings et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,347,868 B2 | 3/2008 | Burnett et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,566,300 B2 | 7/2009 | Devierre et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,697,972 B2 | 4/2010 | Verard et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,775,968 B2 | 8/2010 | Mathis |
| 7,785,315 B1 | 8/2010 | Muni et al. |
| 7,799,048 B2 | 9/2010 | Hudson et al. |
| 7,799,337 B2 | 9/2010 | Levin |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| 7,857,750 B2 | 12/2010 | Belafsky |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,883,717 B2 | 2/2011 | Varner et al. |
| 7,896,891 B2 | 3/2011 | Catanese, III et al. |
| 7,927,271 B2 | 4/2011 | Dimitriou et al. |
| 7,951,132 B2 | 5/2011 | Eaton et al. |
| 7,988,705 B2 | 8/2011 | Galdonik et al. |
| 7,993,353 B2 | 8/2011 | Roβner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,075,476 B2 | 12/2011 | Vargas |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,146,400 B2 | 4/2012 | Goldfarb et al. |
| 8,147,545 B2 | 4/2012 | Avior |
| 8,167,821 B2 | 5/2012 | Sharrow |
| 8,172,828 B2 | 5/2012 | Chang et al. |
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,414,473 B2 | 4/2013 | Jenkins et al. |
| 8,425,457 B2 | 4/2013 | John et al. |
| 8,439,687 B1 | 5/2013 | Morriss et al. |
| 8,475,360 B2 | 7/2013 | Brown |
| 8,529,439 B2 | 9/2013 | Ito et al. |
| 8,535,707 B2 | 9/2013 | Arensdorf et al. |
| 8,702,626 B1 | 4/2014 | Kim et al. |
| 8,715,169 B2 | 5/2014 | Chang et al. |
| 8,721,591 B2 | 5/2014 | Chang et al. |
| 8,747,389 B2 | 6/2014 | Goldfarb et al. |
| 8,764,709 B2 | 7/2014 | Chang et al. |
| 8,764,726 B2 | 7/2014 | Chang et al. |
| 8,764,729 B2 | 7/2014 | Muni et al. |
| 8,777,926 B2 | 7/2014 | Chang et al. |
| 8,828,041 B2 | 9/2014 | Chang et al. |
| 8,852,143 B2 | 10/2014 | Chang et al. |
| 9,649,477 B2 | 5/2017 | Muni et al. |
| 9,700,326 B2 | 7/2017 | Morriss et al. |
| 2001/0004644 A1 | 6/2001 | Levin |
| 2001/0005785 A1 | 6/2001 | Sachse |
| 2001/0034530 A1 | 10/2001 | Malackowski et al. |
| 2002/0006961 A1 | 1/2002 | Katz et al. |
| 2002/0055746 A1 | 5/2002 | Burke et al. |
| 2002/0068851 A1 | 6/2002 | Gravenstein et al. |
| 2002/0077593 A1 | 6/2002 | Perkins et al. |
| 2002/0077594 A1* | 6/2002 | Chien ............... A61M 25/10 604/103.02 |
| 2002/0090388 A1 | 7/2002 | Humes et al. |
| 2002/0115963 A1 | 8/2002 | Clarke et al. |
| 2003/0013985 A1 | 1/2003 | Saadat |

(56) References Cited

U.S. PATENT DOCUMENTS

| | | | |
|---|---|---|---|
| 2003/0017111 A1 | 1/2003 | Rabito | |
| 2003/0018291 A1 | 1/2003 | Hill et al. | |
| 2003/0040697 A1 | 2/2003 | Pass et al. | |
| 2003/0073900 A1 | 4/2003 | Senarith et al. | |
| 2003/0083608 A1 | 5/2003 | Evans et al. | |
| 2003/0114732 A1 | 6/2003 | Webler et al. | |
| 2003/0163154 A1 | 8/2003 | Miyata et al. | |
| 2003/0220551 A1 | 11/2003 | Kimball et al. | |
| 2004/0015150 A1 | 1/2004 | Zadno-Azizi | |
| 2004/0018980 A1 | 1/2004 | Gurney et al. | |
| 2004/0020492 A1 | 2/2004 | Dubrul et al. | |
| 2004/0034311 A1 | 2/2004 | Mihalcik | |
| 2004/0043052 A1 | 3/2004 | Hunter et al. | |
| 2004/0044361 A1* | 3/2004 | Frazier | A61B 17/0057 606/200 |
| 2004/0058992 A1 | 3/2004 | Marinello et al. | |
| 2004/0064105 A1 | 4/2004 | Capes et al. | |
| 2004/0116958 A1 | 6/2004 | Gopferich et al. | |
| 2004/0127820 A1 | 7/2004 | Clayman et al. | |
| 2004/0158229 A1 | 8/2004 | Quinn | |
| 2004/0181175 A1 | 9/2004 | Clayman et al. | |
| 2004/0193073 A1 | 9/2004 | DeMello et al. | |
| 2004/0220516 A1 | 11/2004 | Solomon et al. | |
| 2004/0230156 A1 | 11/2004 | Schreck et al. | |
| 2004/0236231 A1 | 11/2004 | Knighton et al. | |
| 2004/0249243 A1 | 12/2004 | Kleiner | |
| 2004/0267347 A1 | 12/2004 | Cervantes | |
| 2005/0027249 A1 | 2/2005 | Reifart et al. | |
| 2005/0038319 A1 | 2/2005 | Goldwasser et al. | |
| 2005/0043678 A1* | 2/2005 | Freyman | A61M 29/02 604/103.01 |
| 2005/0055077 A1 | 3/2005 | Marco | |
| 2005/0059930 A1 | 3/2005 | Garrison et al. | |
| 2005/0059931 A1 | 3/2005 | Garrison et al. | |
| 2005/0089670 A1 | 4/2005 | Large | |
| 2005/0107738 A1 | 5/2005 | Slater et al. | |
| 2005/0113687 A1 | 5/2005 | Herweck et al. | |
| 2005/0113850 A1 | 5/2005 | Tagge | |
| 2005/0119590 A1 | 6/2005 | Burmeister et al. | |
| 2005/0131316 A1 | 6/2005 | Flagle et al. | |
| 2005/0143687 A1 | 6/2005 | Rosenblatt et al. | |
| 2005/0154416 A1* | 7/2005 | Herweck | A61L 29/041 606/194 |
| 2005/0182319 A1 | 8/2005 | Glossop | |
| 2005/0228224 A1 | 10/2005 | Okada et al. | |
| 2005/0234388 A1* | 10/2005 | Amos | A61M 27/008 604/8 |
| 2005/0234507 A1 | 10/2005 | Geske et al. | |
| 2005/0240120 A1 | 10/2005 | Modesitt | |
| 2005/0244472 A1 | 11/2005 | Hughes et al. | |
| 2005/0245906 A1* | 11/2005 | Makower | A61B 5/06 604/891.1 |
| 2005/0283221 A1 | 12/2005 | Mann et al. | |
| 2006/0004323 A1 | 1/2006 | Chang et al. | |
| 2006/0047261 A1 | 3/2006 | Joshi | |
| 2006/0063973 A1 | 3/2006 | Makower et al. | |
| 2006/0173382 A1 | 8/2006 | Schreiner | |
| 2006/0189844 A1 | 8/2006 | Tien | |
| 2006/0190022 A1 | 8/2006 | Beyar et al. | |
| 2006/0211752 A1 | 9/2006 | Kohn et al. | |
| 2006/0271024 A1 | 11/2006 | Gertner et al. | |
| 2006/0284428 A1 | 12/2006 | Beadle et al. | |
| 2007/0020196 A1 | 1/2007 | Pipkin et al. | |
| 2007/0112358 A1 | 5/2007 | Abbott | |
| 2007/0129751 A1 | 6/2007 | Muni et al. | |
| 2007/0135789 A1 | 6/2007 | Chang et al. | |
| 2007/0167682 A1 | 7/2007 | Goldfarb et al. | |
| 2007/0207186 A1 | 9/2007 | Scanlon et al. | |
| 2007/0208252 A1 | 9/2007 | Makower | |
| 2007/0208301 A1 | 9/2007 | Evard et al. | |
| 2007/0249896 A1 | 10/2007 | Goldfarb et al. | |
| 2007/0250105 A1 | 10/2007 | Ressemann et al. | |
| 2007/0269385 A1 | 11/2007 | Yun et al. | |
| 2007/0282305 A1 | 12/2007 | Goldfarb et al. | |
| 2007/0293727 A1 | 12/2007 | Goldfarb et al. | |
| 2007/0293946 A1 | 12/2007 | Gonzales et al. | |
| 2008/0015544 A1 | 1/2008 | Keith et al. | |
| 2008/0033519 A1 | 2/2008 | Burwell et al. | |
| 2008/0051804 A1 | 2/2008 | Cottler et al. | |
| 2008/0097516 A1 | 4/2008 | Chang et al. | |
| 2008/0103521 A1 | 5/2008 | Makower et al. | |
| 2008/0119693 A1 | 5/2008 | Makower et al. | |
| 2008/0125626 A1 | 5/2008 | Chang et al. | |
| 2008/0132938 A1 | 6/2008 | Chang et al. | |
| 2008/0172033 A1 | 7/2008 | Keith et al. | |
| 2008/0183128 A1 | 7/2008 | Morriss et al. | |
| 2008/0188803 A1 | 8/2008 | Jang | |
| 2008/0188870 A1 | 8/2008 | Andre et al. | |
| 2008/0195041 A1 | 8/2008 | Goldfarb et al. | |
| 2008/0228085 A1 | 9/2008 | Jenkins et al. | |
| 2008/0262508 A1 | 10/2008 | Clifford et al. | |
| 2008/0275483 A1 | 11/2008 | Makower et al. | |
| 2008/0281156 A1 | 11/2008 | Makower et al. | |
| 2008/0287908 A1 | 11/2008 | Muni et al. | |
| 2008/0319424 A1 | 12/2008 | Muni et al. | |
| 2009/0030274 A1 | 1/2009 | Goldfarb et al. | |
| 2009/0088728 A1 | 4/2009 | Dollar et al. | |
| 2009/0156980 A1 | 6/2009 | Eaton et al. | |
| 2009/0163890 A1 | 6/2009 | Clifford et al. | |
| 2009/0187089 A1 | 7/2009 | Say et al. | |
| 2009/0187098 A1 | 7/2009 | Makower et al. | |
| 2009/0198216 A1 | 8/2009 | Muni et al. | |
| 2009/0240112 A1 | 9/2009 | Goldfarb et al. | |
| 2009/0240237 A1 | 9/2009 | Goldfarb et al. | |
| 2009/0312745 A1 | 12/2009 | Goldfarb et al. | |
| 2010/0030031 A1 | 2/2010 | Goldfarb et al. | |
| 2010/0042046 A1 | 2/2010 | Chang et al. | |
| 2010/0087811 A1 | 4/2010 | Herrin et al. | |
| 2010/0114066 A1 | 5/2010 | Makower et al. | |
| 2010/0174138 A1 | 7/2010 | Chang et al. | |
| 2010/0174308 A1 | 7/2010 | Chang et al. | |
| 2010/0198191 A1 | 8/2010 | Clifford et al. | |
| 2010/0198247 A1 | 8/2010 | Chang et al. | |
| 2010/0198302 A1 | 8/2010 | Shalev | |
| 2010/0210901 A1 | 8/2010 | Makower et al. | |
| 2010/0211007 A1 | 8/2010 | Lesch, Jr. et al. | |
| 2010/0268245 A1 | 10/2010 | Chang et al. | |
| 2010/0274188 A1 | 10/2010 | Chang et al. | |
| 2010/0290244 A1 | 11/2010 | Nath | |
| 2010/0298862 A1 | 11/2010 | Chang et al. | |
| 2011/0004057 A1 | 1/2011 | Goldfarb et al. | |
| 2011/0015482 A1 | 1/2011 | Carrillo, Jr. | |
| 2011/0060214 A1 | 3/2011 | Makower | |
| 2011/0112512 A1 | 5/2011 | Muni et al. | |
| 2011/0166190 A1 | 7/2011 | Anderson et al. | |
| 2012/0071710 A1 | 3/2012 | Gazdzinski | |
| 2012/0071824 A1 | 3/2012 | Chang et al. | |
| 2012/0136207 A1 | 5/2012 | Goldfarb et al. | |
| 2012/0184983 A1 | 7/2012 | Chang et al. | |
| 2012/0245419 A1 | 9/2012 | Makower et al. | |
| 2012/0265094 A1 | 10/2012 | Goldfarb et al. | |
| 2013/0231529 A1 | 9/2013 | John et al. | |
| 2013/0245608 A1 | 9/2013 | Muni et al. | |
| 2013/0261388 A1 | 10/2013 | Jenkins et al. | |

FOREIGN PATENT DOCUMENTS

| | | |
|---|---|---|
| CN | 2151720 | 1/1994 |
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 0515201 | 11/1992 |

(56) References Cited

FOREIGN PATENT DOCUMENTS

| | | |
|---|---|---|
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1166710 | 1/2002 |
| EP | 1413258 | 4/2004 |
| EP | 1944053 | 7/2008 |
| FR | 2662083 | 11/1991 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | 10-24098 | 1/1989 |
| JP | 10-034376 | 2/1989 |
| JP | 3-503011 | 7/1991 |
| JP | 3-504935 | 10/1991 |
| JP | 4-221313 | 8/1992 |
| JP | 4-224766 | 8/1992 |
| JP | H5-503650 | 6/1993 |
| JP | 5-211985 | 8/1993 |
| JP | 06-17751 | 3/1994 |
| JP | 6-277296 | 10/1994 |
| JP | 7-327916 | 12/1995 |
| JP | 8-317989 | 12/1996 |
| JP | H10-94543 | 4/1998 |
| JP | 11-507251 | 6/1999 |
| JP | 2000-501634 | 2/2000 |
| JP | 2000-126303 | 5/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-049583 | 2/2004 |
| JP | 2004-357728 | 12/2004 |
| JP | 2005-323702 | 11/2005 |
| JP | 2005-532869 | 11/2005 |
| JP | 2008-539031 | 11/2008 |
| RU | 2108764 | 4/1998 |
| RU | 2213530 | 10/2003 |
| SU | 1662571 | 7/1991 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 94/021320 | 9/1994 |
| WO | WO 95/002430 | 1/1995 |
| WO | WO 96/029071 | 9/1996 |
| WO | WO 97/021461 | 6/1997 |
| WO | WO 98/055174 | 12/1998 |
| WO | WO 99/000064 | 1/1999 |
| WO | WO 99/024106 | 5/1999 |
| WO | WO 99/026692 | 6/1999 |
| WO | WO 99/030655 | 6/1999 |
| WO | WO 99/032041 | 7/1999 |
| WO | WO 99/059649 | 11/1999 |
| WO | WO 00/009190 | 2/2000 |
| WO | WO 00/009192 | 2/2000 |
| WO | WO 00/023009 | 4/2000 |
| WO | WO 00/051672 | 9/2000 |
| WO | WO 00/053252 | 9/2000 |
| WO | WO 00/067834 | 11/2000 |
| WO | WO 01/005462 | 1/2001 |
| WO | WO 01/045572 | 6/2001 |
| WO | WO 01/054558 | 8/2001 |
| WO | WO 01/056481 | 8/2001 |
| WO | WO 01/068178 | 9/2001 |
| WO | WO 01/070325 | 9/2001 |
| WO | WO 01/074266 | 10/2001 |
| WO | WO 01/097895 | 12/2001 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/045387 | 6/2004 |
| WO | WO 04/058045 | 7/2004 |
| WO | WO 04/082525 A2 | 9/2004 |
| WO | WO 04/082525 A3 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/034203 | 3/2007 |
| WO | WO 07/035204 | 3/2007 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |

OTHER PUBLICATIONS

U.S. Appl. No. 10/944,270.
U.S. Appl. No. 11/193,020.
U.S. Appl. No. 11/355,512.
U.S. Appl. No. 11/436,892.
U.S. Appl. No. 11/438,090.
U.S. Appl. No. 11/647,530.
U.S. Appl. No. 11/648,158.
U.S. Appl. No. 11/655,794.
U.S. Appl. No. 11/725,151.
U.S. Appl. No. 11/789,704.
U.S. Appl. No. 11/789,705.
U.S. Appl. No. 11/803,695.
U.S. Appl. No. 11/804,308.
U.S. Appl. No. 11/804,309.
U.S. Appl. No. 11/888,284.
U.S. Appl. No. 11/926,565.
U.S. Appl. No. 11/928,097.
U.S. Appl. No. 11/929,667.
U.S. Appl. No. 11/929,808.
U.S. Appl. No. 11/930,716.
U.S. Appl. No. 11/930,786.
U.S. Appl. No. 12/100,361.
U.S. Appl. No. 12/143,698.
U.S. Appl. No. 12/184,166.
U.S. Appl. No. 12/341,602.
U.S. Appl. No. 12/496,226.
U.S. Appl. No. 12/543,445.
U.S. Appl. No. 12/639,919.
U.S. Appl. No. 12/649,027.
U.S. Appl. No. 12/727,190.
U.S. Appl. No. 12/729,109.
U.S. Appl. No. 12/768,963.
U.S. Appl. No. 12/769,915.
U.S. Appl. No. 12/793,352.

(56) References Cited

OTHER PUBLICATIONS

U.S. Appl. No. 12/828,170.
U.S. Appl. No. 12/949,708.
U.S. Appl. No. 13/301,406.
U.S. Appl. No. 13/315,191.
U.S. Appl. No. 13/355,758.
U.S. Appl. No. 13/429,857.
U.S. Appl. No. 13/451,453.
U.S. Appl. No. 13/784,293.
U.S. Appl. No. 13/840,430.
U.S. Appl. No. 13/858,580.
U.S. Appl. No. 13/867,972.
U.S. Appl. No. 14/221,550.
U.S. Appl. No. 14/221,621.
U.S. Appl. No. 14/221,714.
U.S. Appl. No. 14/265,787.
U.S. Appl. No. 14/265,888.
U.S. Appl. No. 14/266,002.
U.S. Appl. No. 14/266,025.
U.S. Appl. No. 14/327,593.
U.S. Appl. No. 14/464,948.
U.S. Appl. No. 14/515,687.
Supplemental European Search Report dated Sep. 8, 2011 for Application No. EP 06800540.4.
Extended European Search Report dated Jun. 28, 2017 for Application No. EP 17159646.3.
Argon Medical. Maxxim Medical. Ad for Sniper EliteTM Hydrophilic Ni-Ti Alloy Guidewire (2001).
Aust, R., et al. 'The Functional Size of the Human Maxillary Ostium in Vivo' Acta. Otolaryn. (9178) vol. 78 pp. 432-435.
Baim, D.S., MD 'Grossman's Cardiac Catheterization, Angiography, and Intervention' (2000) Lippincott Williams & Wilkins pp. 76, 84 & 214.
Barrett, S. 'Be Wary of Neurocranial Restructuring (NCR)' Chirobase; Jul. 2003; www.chirobase.org/06DD/ncr.html.
Bartal, N. 'An Improved stent for Use in the Surgical Management of Congential Posterior Choanal Atresia' J. Laryngol. Otol (1988) vol. 102 pp. 146-147.
Becker, A.E. 'Restenosis After Angioplasty' The Lancet (1988) vol. 331, No. 8584 p. 532.
Bellis, M. History of the Catheter-Balloon Catheter—Thomas Fogarty. www.inventors.about.com/library/inventors/blcatheter.htm?p=1.
Benninger et al.; Adult Chronic Rhinosinusitis: Definitions, Diagnosis, Epidemiology, and Pathophysilogy Arch Otolarygol Head and Neck Surg. vol. 129 (Sep. 2003) pp. A1-S32.
Bent et al. 'The Frontal Cell as a Cause of Frontal Sinus Obstruction' American Journal of Rhinology, vol. 8, No. 4 (1994) pp. 185-191.
Binner et al. 'Fibre-Optic Transillunination of the Sinuses: A Comparison of the Value of Radiography and Transillummination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: the University of Miami Experience' American Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery' Drugs and Pharmaceutical Sciences, vol. 39, pp. 60-63.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers-General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue 1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Teknika, No. 5 (1974) pp. 54.55.
Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatrc Otorhinolaryngol (1991) vol. 21 pp. 97-101.
Gerus, I.I. et al. 'β-Ethosyvinyl Polyfluroroalkyl Ketones—Versatile Synthones in Floroorganic Chemistry' Journal of Fluorine Chemistry. vol. 69 (1994) pp. 195-198. Elesvier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE Abstract (Mar. 2001) B-04353.
Gottman, et al., Balloon Dilatation of Recurrent Ostial Occlusion of the Front Sinus' OASIS-Online Abstract Submission and Invitation System, 1996-2006, Coe Truman Technologies, Inc.
Gottmann, et al. 'Successful Treatment of Recurrent Post-Operative Frontal Sinus Stenoses by Balloon Dilatation' CIRSE. (Oct. 5, 2002).
Gottmann, D. 'Treatment of Stenoses of Upper Air Routes by Balloon Dilation' Proceeding of the 83rd Annual Convention of Association of West German ENT Physicians (1999).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.

(56) References Cited

OTHER PUBLICATIONS

Hashim, et al. 'Balloon Compression of the Intermaxillary Sinus for Intractable Post Traumatic Bleeding from the Maxillary Artery' Scandinavian Journal of Plastic and reconstruction Sergery and Hand Surgery (1999) vol. 33 pp. 321-324.
Hojo, M. et al, 'Electrophilic Substiutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Miniature Edoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Would Healing of the Paranasal Sinuses—Clinical and Experimental Investigations' Eur Arch Otorhinolarygol. vol. 248, (1991) pp. 390-394.
Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes (Apr. 1999) www.brooksidepress.org/Products/Operationa. Medicine/DATA. 2001 pp. 1-6.
Hybels, R.L. 'Transillumination Durning Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' Ther Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clincal Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net/rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa In the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.

Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' Internatinal Advanced Sinus Symposium (1993) Jul. 21-24.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopostic Approach' Op Tech Otolaryngo Head Neck Surgery. 6 (1995) pp. 184-192.
Medtronic, xomed.com—MicroFrance Catalog Browser. www.xomcat.com/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 57-512.
Min, Y-G et al. 'Mucociliary Activity and Histopathology of Sinus Mucosa in Experimental Maxilary Sinusitis: A Comparison of Systemic Administration of Antibiotic Delivery by Polyactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exhange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com.au/ent/nasal.html.
Park. K. et al. 'Biodegradable Hydrogels for Durg Delivery' (1993) Technomic Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedon for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Rhinology Products, Boston Medical Products, www.bosmed.com, [date of publication unknown], pp. 1-16.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine (May 1952) pp. 281-288.

(56) References Cited

OTHER PUBLICATIONS

St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. www.pinpointmedical.com/ent-news (2009) vol. 17, No. 6 pp. 60-63.
Sanborn, T.A. et al., 'Percutaneous Endocardial Transfer and Expression of Genes to Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems.
Sinusitis, Maxillary, Acute Surgical Treatement. http://www.emedicine.com/ent/topic340.htm. Aug. 29, 2006. pp. 1-11.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasen-nebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation (Sep. 25, 1999) pp. 1-4.
Strohm, et al 'Le Traitement Des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 2003, Surg Trainer, Ltd. Ibaraki, Japan.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn-Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngolgoy (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying copy of poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
Australian Office Action, Examiners First Report dated Dec. 9, 2011 for Application No. AU 2006292818.
Australian Office Action, dated Feb. 12, 2014 for Application No. AU 2012202103.
Chinese Office Action, First Office Action dated Nov. 5, 2012 for CN 200980137396.1.
Chinese Search Report dated Oct. 29, 2012 for Application No. CN 200980137396.1.
Chinese Search Report dated Jan. 11, 2013 for Application No. CN 200980152995.0.
Chinese Office Action, First Office Action dated Jan. 29, 2013 for CN 200980152995.1.
European Communication dated Sep. 4, 2008 for Application No. EP 05773189.
European Communication dated Jun. 19, 2009 for Application No. EP 05773189.
European Communication dated Aug. 1, 2012 for Application No. EP 06784759.0.
European Communication dated Aug. 24, 2012 for Application No. EP 05798331.4.
European Communication dated Nov. 9, 2012 for Application No. EP 07750248.2.
European Communication dated Apr. 19, 2012 for Application No. EP 08746715.5.
European Communication dated Jan. 7, 2013 for Application No. EP 08746715.5.
European Communication dated Apr. 11, 2013 for Application No. EP 05778834.1.
European Communication dated May 10, 2013 for Application No. EP 06751637.7.
European Communication dated Sep. 27, 2011 for Application No. EP 06800540.4.
European Communication dated Sep. 3, 2013 for Application No. EP 12182998.0
European Communication dated Feb. 26, 2014 for Application No. EP 06800540.4
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Mar. 16, 2010 re Application No. EP 06718986.
European Search Report dated Sep. 27, 2011 for Application No. EP 10182961.
European Search Report dated Sep. 29, 2011 Application No. EP 10182893.
European Search Report dated Jul. 23, 2012 for Application No. EP 12162709.
European Search Report dated Jul. 24, 2012 for Application No. EP 12162712.

(56) References Cited

OTHER PUBLICATIONS

European Search Report dated Aug. 31, 2012 for Application No. EP 12173295.
European Search Report dated Oct. 10, 2012 for Application No. EP 12175607.
European Search Report dated Nov. 22, 2012 for Application No. EP 12182993.
European Search Report dated Dec. 5, 2012 for Application No. EP 12182998.
European Search Report dated Jan. 9, 2013 for Application No. EP 12183000.
European Search Report dated Jan. 11, 2013 for Application No. EP 12183002.
European Search Report dated Aug. 13, 2013 for Application No. EP 13172140.
European Search Report dated Sep. 9, 2013 for Application No. EP 13179223.
Extended European Search Report dated Jan. 17, 2014 for Application No. EP 108426321.1.
Partial European Search Report dated Sep. 20, 2007 for Application No. EP 07252018.
Partial European Search Report dated Mar. 25, 2008 for Application No. EP 07252018.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
Supplemental European Search Report dated Jan. 14, 2014 for Application No. EP 13184009.
Supplemental European Search Report dated Jan. 17, 2014 for Application No. EP 1084263.
Supplemental European Search Report dated Feb. 13, 2014 for Application No. EP 08746464.
PCT Search Report dated Nov. 30, 2009 for Application No. UPCT/US2009/057203.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Prelimary Report on Patentability dated Feb. 15, 2008 for Application No. PCT/US05/13617.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Prelminary Report on Patentability and Written Opinion dated May 5, 2009 for Application No. PCT/US06/036960.
International Prelminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability dated Jun. 29, 2011 for Application No. PCT/US2009/069143.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report dated Aug. 17, 2007 for Application No. PCT/US05/013617.
International Search Report dated Aug. 29, 2007 for Application No. PCT/US06/002004.
International Search Report dated Sep. 25, 2007 for Application No. PCT/US06/037167.
International Search Report dated Oct. 19, 2007 for Application No. PCT/US07/003394.
International Search Report dated May 29, 2008 for Application No. PCT/US07/021170.
International Search Report dated May 29, 2008 for Application No. PCT/US07/021922.
International Search Report dated Jul. 1, 2008 for Application No. PCT/US06/022745.
International Search Report dated Jul. 3, 2008 for Application No. PCT/US2006/029695.
International Search Report dated Jul. 7, 2008 for Application No. PCT/US07/016213.
International Search Report dated Jul. 8, 2008 for Application No. PCT/US07/011474.
International Search Report dated Jul. 17, 2008 for Application No. PCT/US06/036960.
International Search Report and Written Opinion dated Jul. 21, 2008 for Application No. PCT/US05/033090.
International Search Report dated Aug. 25, 2008 for Application No. PCT/US2008/000911.
International Search Report dated Sep. 10, 2008 for Application No. PCT/US07/016212.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/011449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Aug. 9, 2011 for Application No. PCT/US2011/038751.

(56) References Cited

OTHER PUBLICATIONS

International Search Report dated May 18, 2012 for Application No. PCT/US2011/052321.
Partial International Search Report dated Feb. 7, 2012 for Application No. PCT/US2011/052321.
Japanese Office Action, Examiner's Decision of Refusal dated Oct. 18, 2011 for Application No. JP 2007-509632.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.
Japanese Office Action, Notification of Reasons for Refusal dated Jun. 25, 2013 for Application No. JP 2012-131840.
Japanese Office Action, Notification of Reasons for Refusal dated Sep. 18, 2013 for Application No. JP 2011-527942.
Japanese Office Action, Notification of Reasons for Refusal dated Nov. 12, 2013 for Application No. JP 2011-542562.
Japanese Office Action, Notification of Reasons for Refusal dated Jan. 7, 2014 for Application No. JP 2012-266049.
Russian Office Action dated Sep. 28, 2012 for Application No. RU 2011130530.
Russian Office Action dated Mar. 19, 2013 for Application No. RU 2011130530.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
USPTO Office Action dated Dec. 29, 2008 for U.S. Appl. No. 11/193,020.
USPTO Office Action dated May 13, 2009 for U.S. Appl. No. 11/193,020.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 14/221,550, filed Mar. 21, 2014.
U.S. Appl. No. 14/221,621, filed Mar. 21, 2014.
U.S. Appl. No. 14/221,714, filed Mar. 21, 2014.
U.S. Appl. No. 14/265,787, filed Apr. 30, 2014.
U.S. Appl. No. 14/265,888, filed Apr. 30, 2014.
U.S. Appl. No. 14/266,002, filed Apr. 30, 2014.
U.S. Appl. No. 14/266,025, filed Apr. 30, 2014.
U.S. Appl. No. 14/327,593, filed Jul. 10, 2014.
U.S. Appl. No. 14/464,948, filed Aug. 21, 2014.
U.S. Appl. No. 15/624,093, filed Jun. 15, 2017.

\* cited by examiner

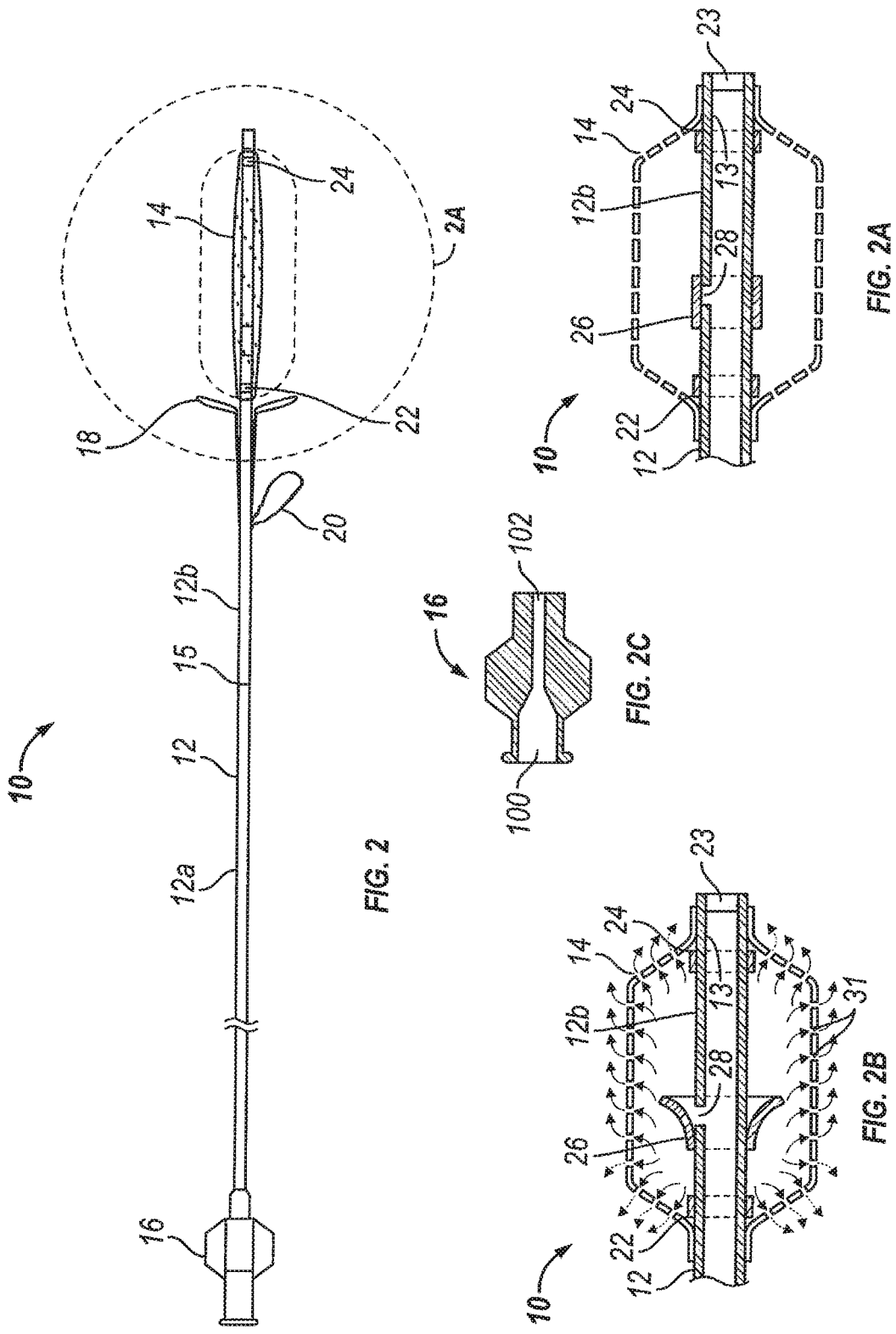

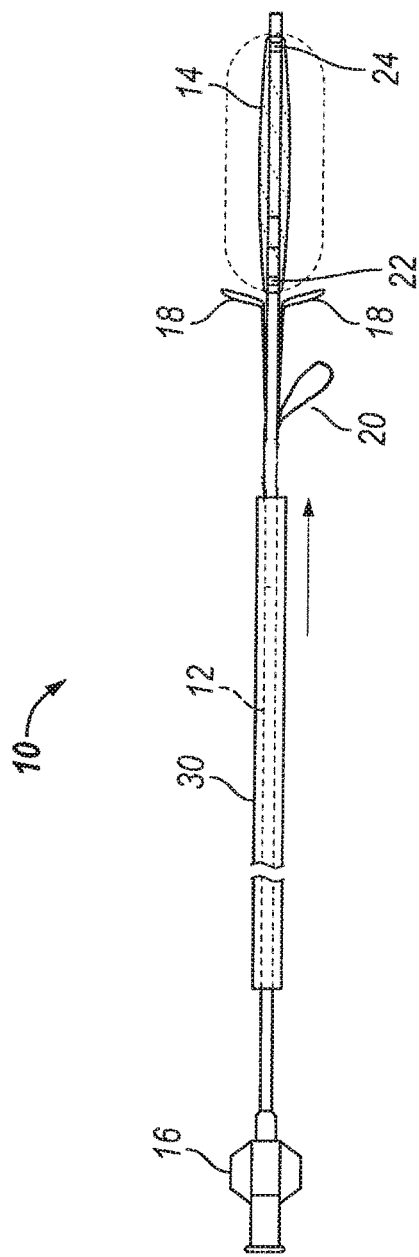
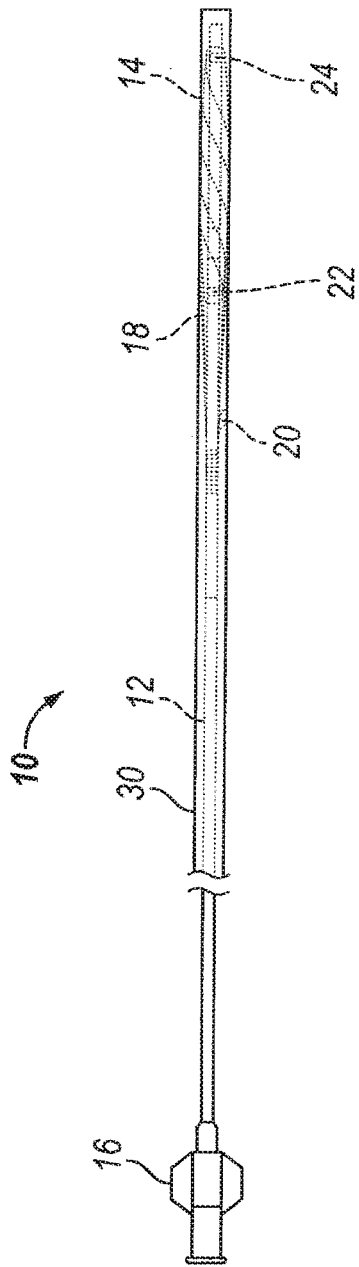
FIG. 2D
FIG. 2E

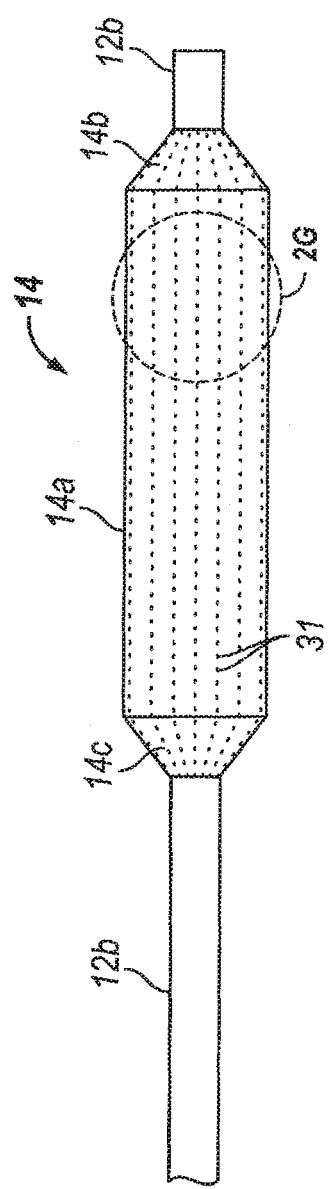
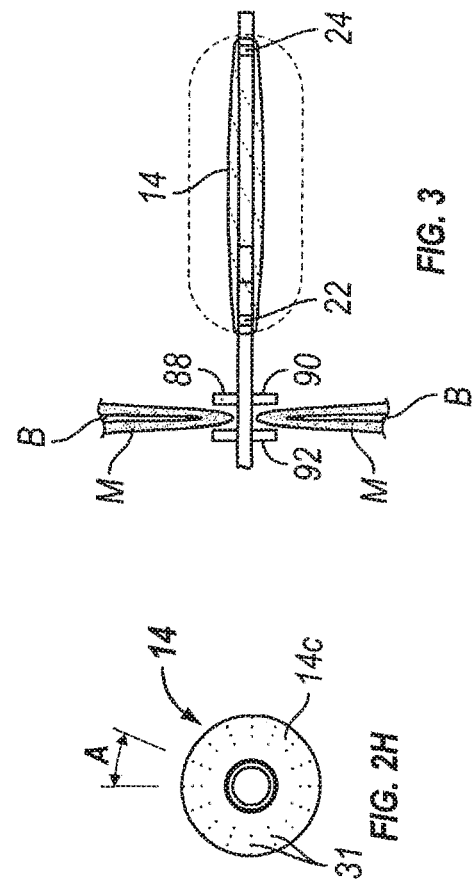
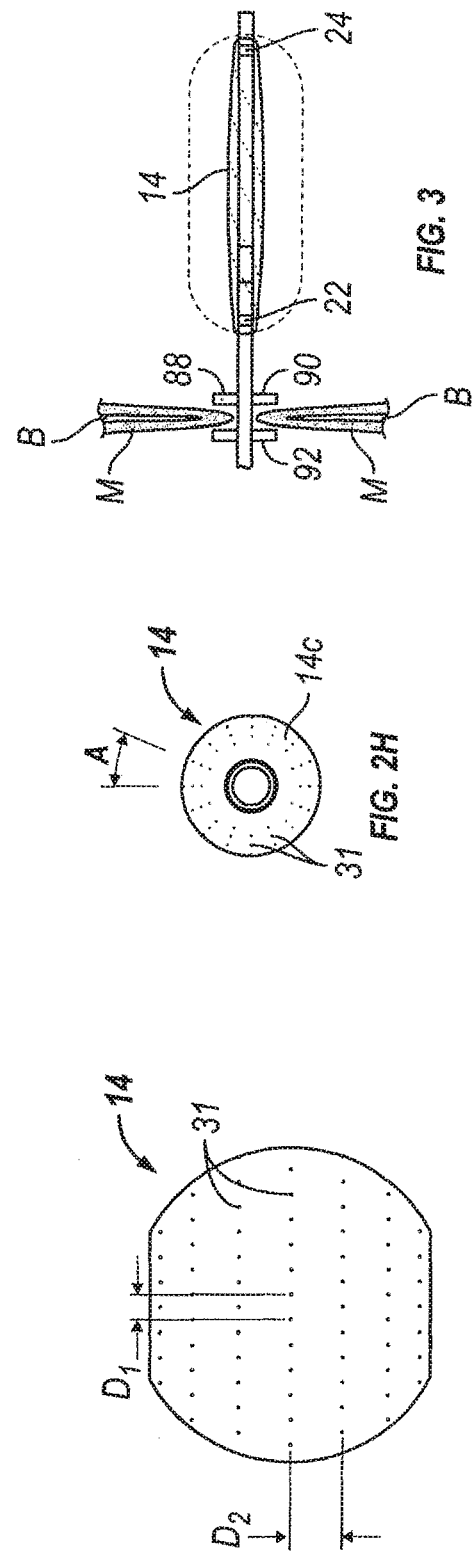

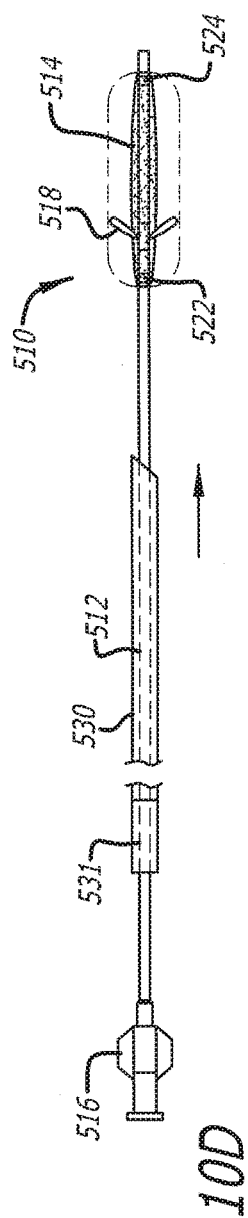
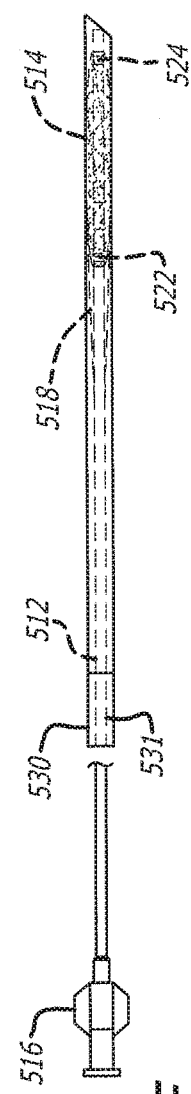
FIG. 10D
FIG. 10E

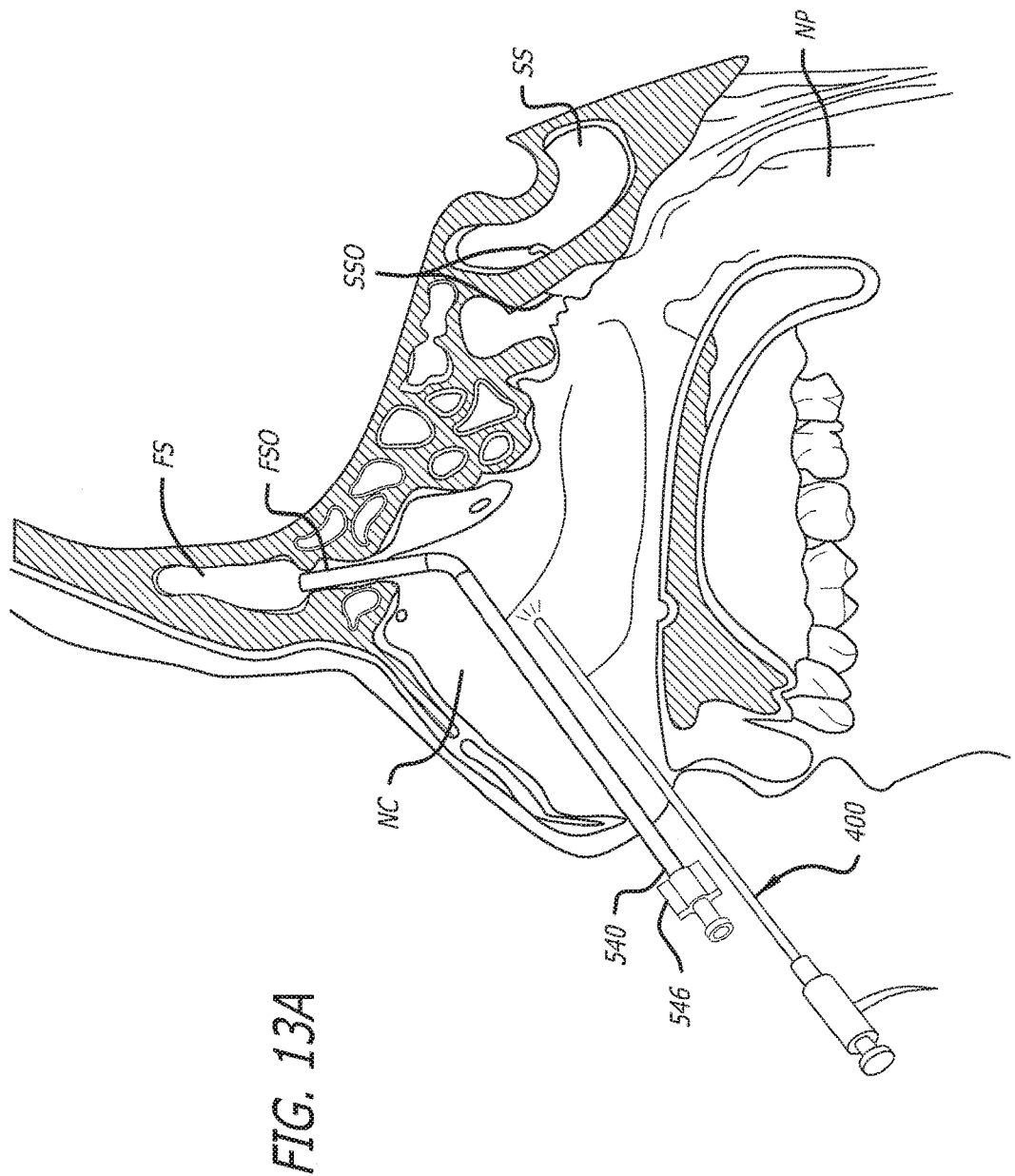

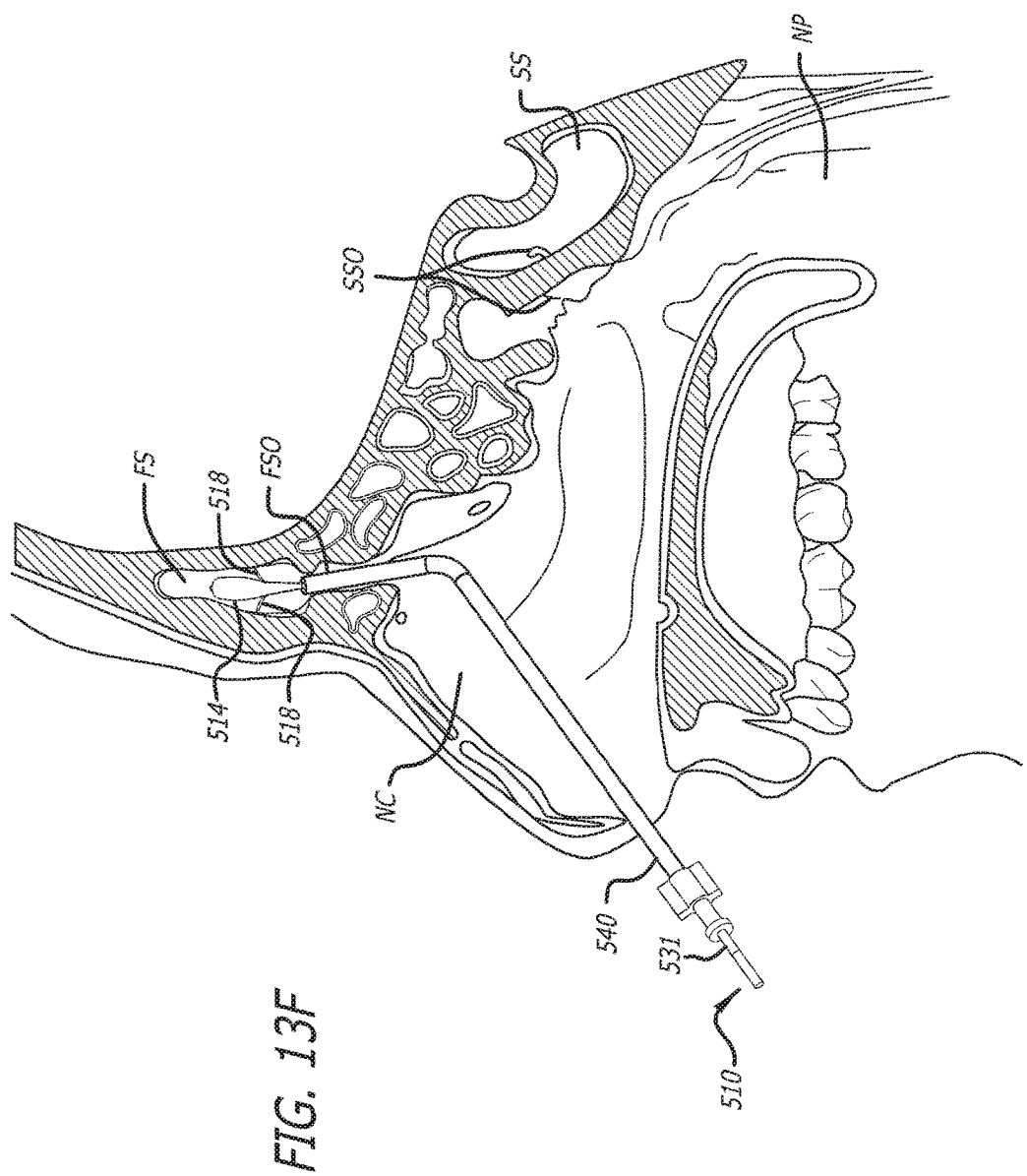

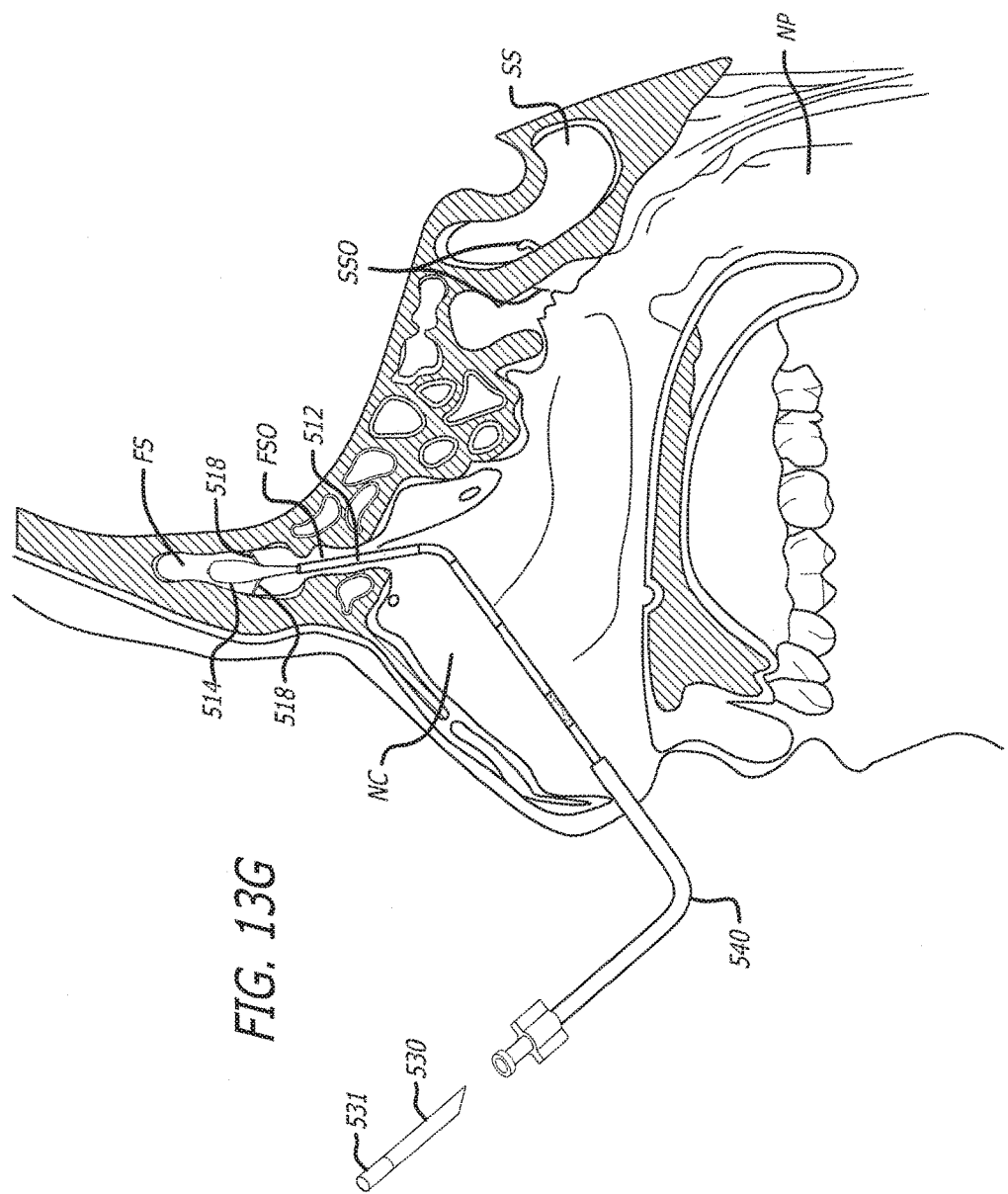

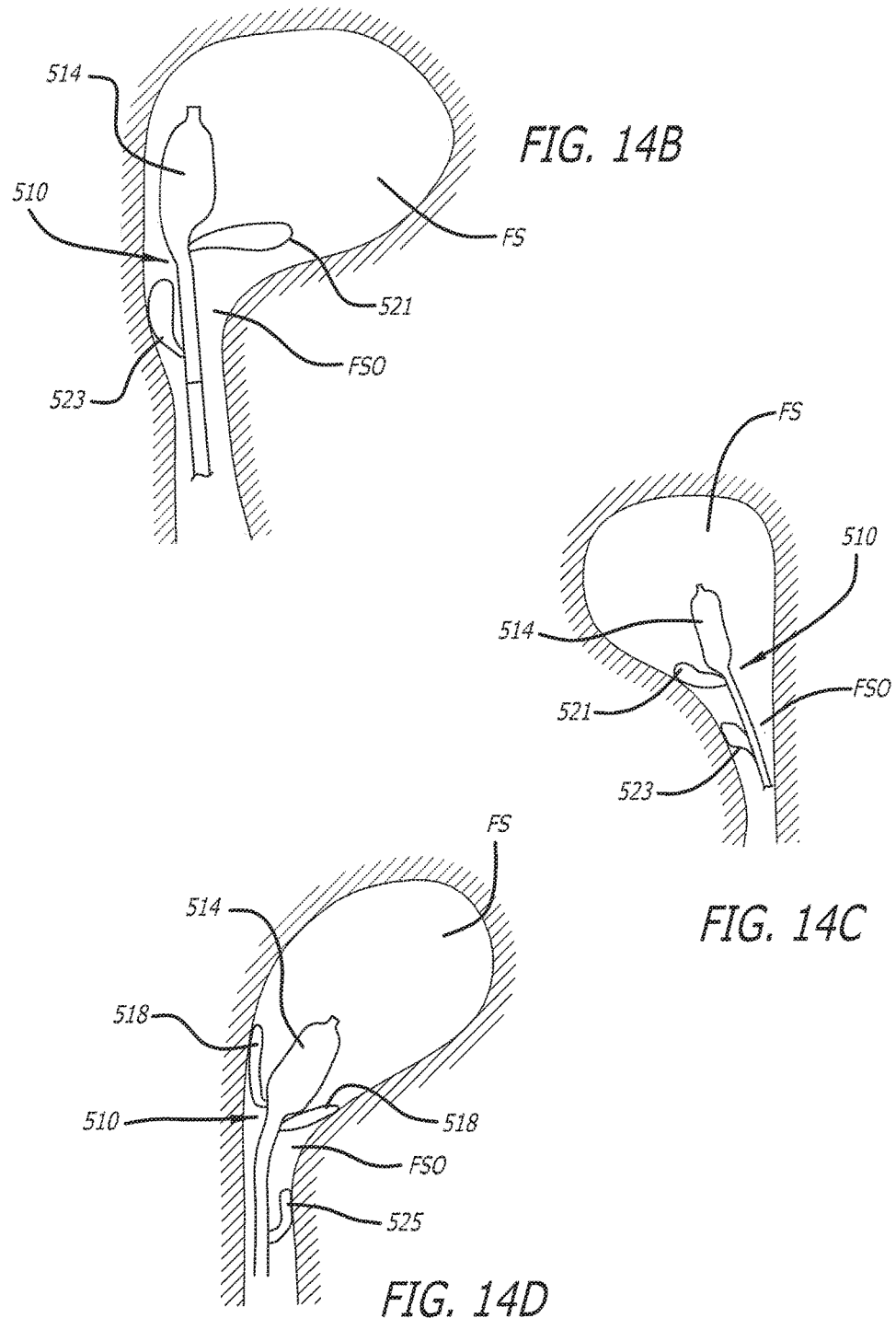

FRONTAL SINUS SPACER

RELATED APPLICATIONS

This patent application is a continuation of U.S. patent application Ser. No. 14/266,002 entitled "Frontal Sinus Spacer" filed on Apr. 30, 2014, now U.S. Pat. No. 9,649,477, which is a continuation of Ser. No. 12/341,602 entitled "Frontal Sinus Spacer" filed on Dec. 22, 2008, now U.S. Pat. No. 8,764,729, which is a continuation-in-part of Ser. No. 12/100,361 entitled "Ethmoidotomy System And Implantable Spacer Devices Having Therapeutic Substance Delivery Capability For Treatment Of Paranasal Sinusitis" filed on Apr. 9, 2008, now U.S. Pat. No. 8,864,787, 1) which is a continuation-in-part of Ser. No. 11/544,009 entitled "Implantable Devices and Methods for Treating Sinusitis and Other Disorders" filed on Oct. 4, 2006, now U.S. Pat. No. 7,419,497, which is a continuation-in-part of Ser. No. 11/234,395 entitled "Devices and Methods for Delivering Therapeutic Substances for the Treatment of Sinusitis and Other Disorders" filed on Sep. 23, 2005, now U.S. Pat. No. 7,410,480, which is a continuation-in-part of Ser. No. 10/829,917 entitled "Devices, Systems and Methods for Diagnosing and Treating Sinusitis and Other Disorders of the Ears, Nose and/or Throat" filed on Apr. 21, 2004, now U.S. Pat. No. 7,654,997, and of Ser. No. 10/912,578 entitled "Implantable Device and Methods for Delivering Drugs and Other Substances to Treat Sinusitis and Other Disorders" filed on Aug. 4, 2004, now U.S. Pat. No. 7,361,168, and 2) which is a continuation-in-part of Ser. No. 11/037,548 entitled "Devices, Systems and Methods for Treating Disorders of the Ear, Nose and Throat" filed on Jan. 18, 2005, now U.S. Pat. No. 7,462,175, the entire disclosure of each such application being expressly incorporated herein by reference.

FIELD OF THE INVENTION

The present invention relates generally to medical devices and methods and more particularly to substance delivering implants and methods for treating a broad range of disorders including but not limited to sinusitis and other ear, nose and throat disorders.

BACKGROUND

The paranasal sinuses require adequate ventilation to prevent microbial chronic infection within the sinus cavities. Normally, ventilation is provided through the small natural openings, known as ostia, through which the sinus cavities open into the nose. In addition to ventilation, the natural ostia serve as drainage channels as ciliated cells lining the interior of the sinus cavity continually direct a flow of mucus toward the ostia. Thus, when the natural ostia become narrowed or blocked, ventilation and drainage from the sinus cavity is impaired. The resultant hypoxia, pH changes and mucus stasis within the sinus cavity gives rise to an environment in which some types of microbial growth can flourish. Such microbial infection can, in itself, result in further mucosal inflammation and even further constriction or blockage of the natural sinus ostium.

Techniques for Improving Ventilation and Drainage of Paranasal Sinuses

Functional endoscopic sinus surgery (FESS) is a common type of surgery wherein an endoscope is inserted into the nose and, under visualization through the endoscope, the surgeon may remove diseased or hypertrophic tissue or bone and may surgically enlarge the ostia of the sinuses to restore normal ventilation and drainage of the sinuses.

As an alternative to incisional surgery, in some patients, a balloon catheter may be advanced into the constricted sinus ostium and used to dilate the ostium, thereby eliminating the need for cutting or removing tissue surrounding the ostium (BALLOON SINUPLASTY™ sinus dilation technology, Acclarent, Inc., Menlo Park, Calif.). Examples of such balloon dilation procedures are described in United States Patent Application Publications No. 2006/0004286, now U.S. Pat. No. 7,720,521, issued May 18, 2010, 2006/0063973, now abandoned, 2006/0210605, now U.S. Pat. No. 7,803,150, issued Sep. 28, 2010, 2007/0129751, now U.S. Pat. No. 8,894,614, issued Nov. 25, 2014, 2007/0135789, now U.S. Pat. No. 8,858,586, issued Oct. 14, 2014, 2007/0167682, now abandoned, 2007/0208252, now abandoned, 2007/0208301, now U.S. Pat. No. 8,951,225, issued Feb. 10, 2015, and 2007/0293727, now U.S. Pat. No. 9,265,407, issued Feb. 23, 2016, the entire disclosure of each such patent application being expressly incorporated herein by reference.

Implantation of Stents and Space Occupying Materials to Deter Re-Occlusion Following Surgery In cases where tissue adjacent to the ostium has been surgically removed or incised, post-operative scar tissue, fibrosis, polyposis or tissue ingrowth can result in re-occlusion of the sinus ostium. To deter such re-occlusion of frontal and sphenoid sinuses following surgery, small tubular stents have been placed in the surgically altered sinus ostium or outflow tract for a limited time period following surgery.

One example of a commercially available frontal sinus stent is the FREEMAN™ Frontal Sinus Stent (InHealth Technologies, Inc., Carpinteria, Calif.). The FREEMAN™ stent comprises a silicon tube that has flanges on either end to retain the stent within the frontal outflow tract for a desired period of time following surgery. Other commercially available frontal sinus stents include the Jasin Frontal Sinus Stent (Medtronic Xomed, Inc., Jacksonville, Fla.), and the Salman FES Stent (Boston Medical Products, Westborough, Mass.).

A sphenoid sinus stent is described in U.S. Pat. No. 7,235,099 (Duncavage, et al.). This stent comprises a soft compressible plastic tube having a generally hemispherical hollow dome on one end. The diameter of the dome is greater than the predetermined diameter of the plastic tube. The stent further includes an annular flange located a predetermined distance from the hemispherical dome. The device is designed to be fitted through a surgically enlarged ostium of the sphenoid sinus such that the dome resides within the sinus cavity and the flange abuts the bony wall surrounding the ostium. This stent serves maintain patency of the surgically altered ostium during the postoperative period and allows irrigation/suctioning through the lumen of the stent. This sphenoid sinus stent is also commercially available as the SP-82020 Sphenoid Sinus Stent (Micromedics, Inc., St. Paul, Minn.).

The above-described frontal and sphenoid sinus stents do not deliver therapeutic substances. Thus, they are frequently used concurrently with orally administered drugs (e.g., corticosteroids) and/or topical nasal sprays.

In some cases, in lieu of a stent, surgeons may place gel-like materials within the surgically altered ostium or outflow tract to prevent ingrowth of scar tissue during the post-surgical period. One example of such material is the MEROPACK™ Bioresorbable Nasal Dressing and Sinus Stent available from Medtronic ENT, Inc., Jacksonville, Fla.

The MEROPACK™ material consists of 80 percent esterified hyaluronic acid and 20 percent collagen. This material is inserted while in its dry state and, upon hydration, swells to 1.0 cm diameter in about six seconds. When in its hydrated state, this material is a biocompatible, mucoadhesive gel.

Local Drug Delivery in the Treatment of Sinus Disease

Various drug delivery implants have been proposed for use in or around the paranasal sinuses to treat sinusitis and/or to deter re-occlusion of surgically altered outflow tracts or ostia following surgery.

For example, United States Patent Application Publication No. 2005/0043706 (Eaton et al.), now U.S. Pat. No. 8,025,635, issued Sep. 27, 2011, describes biodegradable implants for treating sinusitis, such implants having a size, shape, density, viscosity, and/or mucoadhesiveness that prevents them from being substantially cleared by the mucociliary lining of the sinuses during the intended treatment period. These biodegradable implants deliver therapeutic agents such as antibiotics, steroids or both. These biodegradable implants may be in various forms such as rods, pellets, beads, strips, or microparticles, and may be delivered into a sinus in various pharmaceutically acceptable carriers.

Also, United States Patent Application Publication No. 2007/0005094 (Eaton et al.), issued as U.S. Pat. No. 8,025,635 on Sep. 27, 2011, describes implantable devices useable for the treatment of paranasal sinus conditions. The devices include cavity members that have a first collapsed configuration that permits the device to pass through a sinus ostium and a second expanded configuration after placement into the sinus cavity. In addition to a cavity member, the devices may include a nasal portion and an ostial member that is configured to reside within the sinus ostium. The cavity member is attached to the distal end of the ostial member. The nasal portion is attached to the proximal end of the ostial member and lies within the nasal passage. The active agent may be incorporated into all portions of the device or only included in the expandable cavity member, the ostial member, or nasal portion.

Some investigators have proposed adding drug delivery capability to frontal sinus stents to deliver controlled amounts of drug to the surgically altered outflow tract following frontal sinus surgery. For example, United States Patent Application Publication 2004/0116958A1 (Gopferich et al.), now U.S. Pat. No. 8,740,929, issued Jun. 3, 2014, describes a tubular sheath or "spacer" formed of biodegradable or non-biodegradable polymer that, prior to insertion in the frontal outflow tract, is loaded with a controlled amount of an active substance, such as a corticosteroid or anti-proliferative agent. After surgery to create a fenestration in a frontal sinus as been performed, the sheath (which has been preloaded with the active substance) is inserted into the surgically created fenestration where it a) deters closure of the surgically created fenestration, b) serves as a conduit to facilitate drainage from the sinus and c) delivers the active substance. In some embodiments, the sheath is formed of multiple layers of polymeric material, one or more of which is/are loaded with the active substance and one or more of which is/are free of the active substance. In other embodiments, the sheath has a "hollow body" which forms a reservoir system wherein the active substance is contained and a membrane which controls the release of the active substance from the reservoir. In some embodiments, the sheath may be anchored by causing the end of the sheath that extends into the sinus to swell or otherwise enlarge. Also, United States Patent Application Publication No. 2005/0245906 (Makower et al.), now U.S. Pat. No. 7,361,168, issued Apr. 22, 2008, describes a biodegradable polymeric device that comprises a spacer positionable within a sinus ostium. The spacer has a plurality of substance-eluting struts. The device may be implanted such that the struts are substantially parallel to the cilial flow of mucus along the sinus cavity walls so that normal mucociliary transport is not interrupted.

Additionally, various other types of implantable drug delivery devices have been proposed for use in the nose and/or paranasal sinuses. For example, U.S. Pat. No. 3,948,254 (Zaffaroni) describes implantable drug delivery reservoirs having microporous walls. The reservoir may be formed of a solid drug carrier that is permeable to passage of the drug and the rate of passage of the drug through the microporous wall may be slower than the rate at which the drug passes through the solid drug carrier that forms the reservoir. Zaffaroni also describes a number of applications for the implantable drug delivery devices including placement in a nasal passage. Specifically, Zaffaroni claims a nasal delivery device for dispensing a drug within a nasal passage at a controlled rate wherein the nasal device is comprised of (a) a wall defining the device dimensioned for insertion and placement within a nasal passage, with the wall formed of a nasal acceptable microporous material, (b) a reservoir surrounded by the wall and comprised of a solid carrier permeable to drug and containing drug in an amount sufficient for the device to meter it at a continuous and controlled rate for a prolonged period of time from the device, (c) a liquid medium permeable to the passage of drug by diffusion charged in the micropores, and (d) wherein the device releases drug when in a nasal environment by passage of drug from the carrier and through the liquid to the exterior of the device to produce a useful result. The entire disclosure of U.S. Pat. No. 3,948,254 (Zaffaroni) is expressly incorporated herein by reference.

Other publications have also reported that introduction of drugs directly into the paranasal sinuses is effective in the treatment of sinusitis. See, Tarasov, D. I., et al., Application of Drugs Based on Polymers in the Treatment of Acute and Chronic Maxillary Sinusitis, Vestn Otorinolaringol. Vol. 6, Pages 45-7 (1978). Also, R. Deutschmann, et al., A Contribution to the Topical Treatment of [Maxillary] Sinusitis Preliminary Communication, Stomat. DDR 26 (1976), 585-592 describes the placement of a resorbable drug delivery depot within the maxillary sinus for the purposes of eluting drugs, specifically Chloramphenicol. In this clinical series a water soluble gelatin was used as carrier and was mixed with the drug prior to application and introduced as a mass into the sinus. Since the substance had little mechanical integrity and dissolved in a relatively short timeframe, to achieve a therapeutic effect, the author suggested that it must be instilled every 2 to 3 days. An alternative to gelatin could be a sponge loaded with the therapeutic substance as suggested in U.S. Pat. No. 6,398,758 (Jacobsen, et al.). In this patent directed at delivering a sustained release device against the wall of a blood vessel, a hollow cylindrical sponge is loaded with drug and pressed against the wall. This allows the drug to contact the wall while sustaining blood flow within the center of the lumen. Further, a skin is provided to direct the drug into the walls of the blood vessel and prevent drug from flowing into the lumen. While sponges loaded with drug at the time of their application do permit some degree of sustained release, the time required to load them also correlates closely the time over which they will elute substance.

Thus, if delivery is required for a longer period of time additional mechanisms must be employed to regulate their release.

There are also several examples in the patent literature where various sustained release mechanisms have generally been proposed using systems with drugs pre-incorporated into matrices or polymers. These include U.S. Pat. No. 3,948,254 (Zaffaroni), US 2003/0185872A2 (Kochinke), now U.S. Pat. No. 7,074,426, issued Jul. 11, 2006, WO 92/15286 (Shikani), and U.S. Pat. No. 5,512,055 (Domb, et al.). In general, these references discuss various materials and structures that may be used to construct sustained drug delivery vehicles and provide a good overview of the state of sustained drug delivery art. While helpful in laying out certain materials and schemes for creating sustained release systems for drugs, these references do not, however, describe specific methods, means or structures which would permit them to be easily adapted for intended uses that are targeted in the present application.

Other examples of implantable drug delivery devices include those described in U.S. Pat. Nos. 3,993,073; 4,217,898; 5,304,123; 6,042,561; 6,183,461; 6,780,168 and 6,783,522, the entire disclosure of each such patent being expressly incorporated herein by reference.

Techniques for Treatment of Ethmoid Disease

To date, the use of stents and spacers in relation to nose and sinus surgery has been largely limited to placement in the frontal outflow tract or sphenoid sinus ostium following surgery wherein tissue and bone have been cut away or removed. However, as new devices and methods become available for the treatment of other types of nasal and sinus disorders, there will likely be a need for intranasal or sinus spacers and stents (with or without drug eluting capabilities) suitable for placement at various locations lot limited to the frontal outflow tract.

In the prior art, diseased ethmoid air cells have sometimes been treated by a procedure known as an ethmoidectomy wherein a man made passageway is formed between the interiors of the ethmoid air cells and the nasal cavity. Stenting and/or delivery of drugs or other therapeutic substances into these manmade ethmoidectomy passageways has been, in at least some cases, desirable. To accomplish this, strips of gauze soaked with medication may be pushed into the manmade opening and later extracted. Also, in this regard, U.S. Pat. No. 6,543,452 (Lavigne) describes a nasal intubation device that comprises a flexible tube having a flanged distal tip whereon the flanges generally from an arrow shape. The distal tip of this device is capable of penetrating through tissue (e.g., through the ethmoid bulla) to a desired position (e.g., within the ethmoid air cells). Openings are formed in a distal portion of the intubation device so that medication (e.g., a typical steroid) injected through the flexible tube will flow out of the tube into contact with the adjacent area (e.g., the diseased ethmoid air cells). In some cases, a cannula-trocar may be initially inserted and the nasal intubation device may then be advanced through that cannula-trocar. Also, European Patent Publication EP0624349 (Milewski) describes a balloon-tipped catheter having an anatomically shaped balloon which may be inserted through a surgically created opening into a body cavity (e.g., frontal sinus or ethmoid cell) and inflated to create a tamponade by being shaped to suit the anatomical shape of the cavity.

Techniques for Treating the Frontal Sinus

Various of the above challenges are also specifically relevant to the treatment of the frontal sinuses. Additionally, due to the unique anatomy of the frontal sinuses, there are additional challenges. That is, accessing the frontal sinuses can require specialized instrumentality. Moreover, it has been found that conventional FESS procedures on the frontal sinuses have a higher tendency of scarring. Such scarring can lead to a relapse of insufficient drainage and ventilation.

Although corticosteroids have been found to be effective in reducing reactive scarring in the frontal sinuses, there remains a number of key limitations. Nasal sprays and ointments generally do not reach critical areas around the frontal sinus outflow tract. Also, it can be difficult to deliver interventional devices deep within the frontal sinus cavity and there are challenges associated with the retention of interventional instruments in the frontal outflow tract.

Accordingly, there remains a need for the development of new devices and methods for delivering drugs and other therapeutic or diagnostic substances over a sustained period of time into paranasal sinuses, Eustachian tubes, middle ear and/or other locations within the body for the treatment of sinusitis, otitis or other diseases and disorders. In particular, there is a need for an approach to conveniently and effectively access and treat the sinuses such as the frontal sinus.

The present disclosure address these and other needs.

SUMMARY

The present invention provides substance delivering spacer devices and methods including expandable reservoirs that are implantable in paranasal sinuses and other cavities, openings and passageways of the body to maintain patency and/or to provide sustained local delivery of a therapeutic or diagnostic substance. Also provided are sinus penetrator devices, systems and methods for creating ethmoidotomy openings or other openings in the walls of paranasal sinuses or other anatomical structures.

In one particular approach, a system and method have been developed to specifically treat the frontal sinuses. The system can include an elongate shapeable tube or sheath adapted to navigate patient anatomy and to present structure for accessing the frontal sinuses. Various approaches to substance delivery spacers with retention structure have also been developed. In this way, compensations can be made for variations in patient anatomy. Also, in one aspect, the spacer device can additionally include an atraumatic tip such as that formed by a soft polymer.

One embodiment of a substance delivery spacer adapted to treat a frontal sinus includes a shaft and an expandable reservoir attached to a distal portion of the shaft. The reservoir can be introduced within a patient in a collapsed configuration, mounted to the frontal sinuses and then expanded. To expand the reservoir, a substance such as a drug or other therapeutic substance can be loaded within the reservoir. Additionally, the reservoir can embody openings through which the drug or therapeutic substance can elute to thereby treat the frontal sinuses. Moreover, the shaft can be cut to length as desired when leaving the spacer at the interventional site. The spacer can further include retention structure configured to facilitate securing the spacer at or within the frontal sinuses. In this regard, one or more retention wings extending along various portions of the reservoir are contemplated. Such wings can assume a compressed configuration for delivery to the interventional site and expanded configurations for securing the spacer within anatomy.

One embodiment of a device and method for treating ethmoid sinusitis involves a penetrator device that has a distal tip and a stopping mark or member located a spaced distance proximal to its distal tip. The distance between the stopping mark or member and the distal tip is less than the distance between the ethmoid bulla and the ipsalateral sphenoid sinus. An ethmoidotomy channel is formed by advancing the penetrator through the ethmoid bulla in a direction that is non-perpendicular to the skull base and generally directed toward the ipsalateral sphenoid sinus. Advancement of the penetrator is stopped when the stopping mark or member is approximately flush with the ethmoid bulla. Thereafter, the penetrator is removed. Optionally, a stent, spacer or substance delivering spacer device may then be placed in the ethmoidotomy channel for a period of time to maintain patency of the channel and/or to effect local delivery of a therapeutic substance.

According to one embodiment, a sinus penetrator device and method may be used to form an ethmoidotomy channel or other opening in a paranasal sinus wall or other body structure. Such device comprises an elongate penetrator member and a handle coupled with the penetrator member at or near its proximal end. A sighting member is disposed along the handle or the elongate member at a location to make it visible from an extracorporeal vantage point when the distal end of the elongate member is inserted into the patient. Such sighting member is useable by a user of the device to generally aim the distal end of the penetrator in a desired direction within the patient's body. In some embodiments, the sighting member may comprise a fin. The sighting member may extend in a plane that is substantially parallel to a plane in which the elongate the penetrator extends from the handle and, optionally may include another member (e.g., a cross member) that is substantially normal to the plane in which the elongate penetrator extends from the handle. In some embodiments, the elongate penetrator may have a curve formed therein and at least a portion of the sighting member may be parallel to the portion of the elongate penetrator that is distal to the curve, thereby providing an indication of the direction or trajectory on which the distal portion of the elongate penetrator is being advanced.

Still further in accordance with the invention, there is provided a substance delivering spacer device and method. In one embodiment, the substance delivering spacer device comprises a shaft and an expandable reservoir located on the shaft. The reservoir may be introduced into a body cavity or opening (e.g., a paranasal sinus, ethmoidotomy channel, frontal sinus outflow tract, or other body cavity, opening, passageway) while in a collapsed configuration. Thereafter, a therapeutic substance may be loaded into the reservoir, causing the reservoir to expand in situ. The shaft may be severed or cut at a desired location and the proximal portion of the shaft may be removed after the reservoir has been loaded. The reservoir is designed such that the substance will elute from the reservoir over a period of time. The reservoir may have a side wall and tapered ends, with openings being formed in the sidewall and tapered ends such that a therapeutic substance loaded into the reservoir will elute through the openings and out of the reservoir. In some embodiments, the device may be equipped with apparatus for holding the reservoir in a desired position within the body (e.g., retention wings, projections, suture loops, etc.) for holding the reservoir in a desired position within the body.

Still further in accordance with the invention, there is provided a method and system wherein a substance delivering spacer device of the above-described character is used in combination with a sinus penetrator (e.g., the ethmoidotomy device described above or any other penetrator) and a sheath. The sheath is initially disposed over the sinus penetrator and the penetrator/sheath combination is advanced through a wall of a paranasal sinus or air cell. The penetrator is then removed, leaving the sheath in place. The substance delivering spacer device is advanced into the sheath. The sheath is then removed, leaving the substance delivering spacer device in place within the sinus or air cell. A diagnostic or therapeutic substance is then loaded into the reservoir such that the substance will thereafter elute from the reservoir into the paranasal sinus or air cell.

Still further in accordance with the invention, there is provided an embodiment of a method for treating sinusitis where an implantable device having a substance eluting reservoir is positioned within a paranasal sinus or within the ostium or outflow tract of a paranasal sinus. Thereafter, a steroid is introduced into the substance eluting reservoir so that the steroid elutes from the reservoir in an amount that is effective to treat the sinusitis.

Still further aspects and details of the present invention will be understood upon reading of the detailed description and examples set forth below.

BRIEF DESCRIPTION OF THE DRAWINGS

FIG. 2 is a side view of one embodiment of a spacer device of the present invention.

FIG. 2A is an enlarged longitudinal sectional view of a distal portion of the device of Figure A.

FIG. 2B is an enlarged longitudinal sectional view of a distal portion of the device of Figure A during infusion of a substance into the reservoir portion of the device.

FIG. 2C is a longitudinal sectional view through the proximal hub of the device of FIG. 2.

FIG. 2D is a side view of the device of FIG. 2 with a constraining sheath in a retracted position.

FIG. 2E is a side view of the device of FIG. 2 with a constraining sheath in an advanced position.

FIG. 2F is a diagram of the expandable reservoir of the device of FIG. 2.

FIG. 2G is an enlarged view of region 2G of FIG. 2F.

FIG. 2H is a proximal end view of the expandable reservoir of FIG. 2F.

FIG. 3 is a side view of a distal portion of another embodiment of a spacer device of the present invention incorporating an alternative retention system.

FIGS. 10B-10E depict various views and details of a frontal paranasal sinus substance delivery device and constraining sheath for the device according to one embodiment of the present invention.

FIGS. 13A-13H show steps in a method for treating a frontal sinus.

FIGS. 14A-14D depict the implantation of various different spacer devices within the frontal sinus.

DETAILED DESCRIPTION

The following detailed description and the accompanying drawings are intended to describe some, but not necessarily all, examples or embodiments of the invention. The contents of this detailed description do not limit the scope of the invention in any way.

Figure 1:
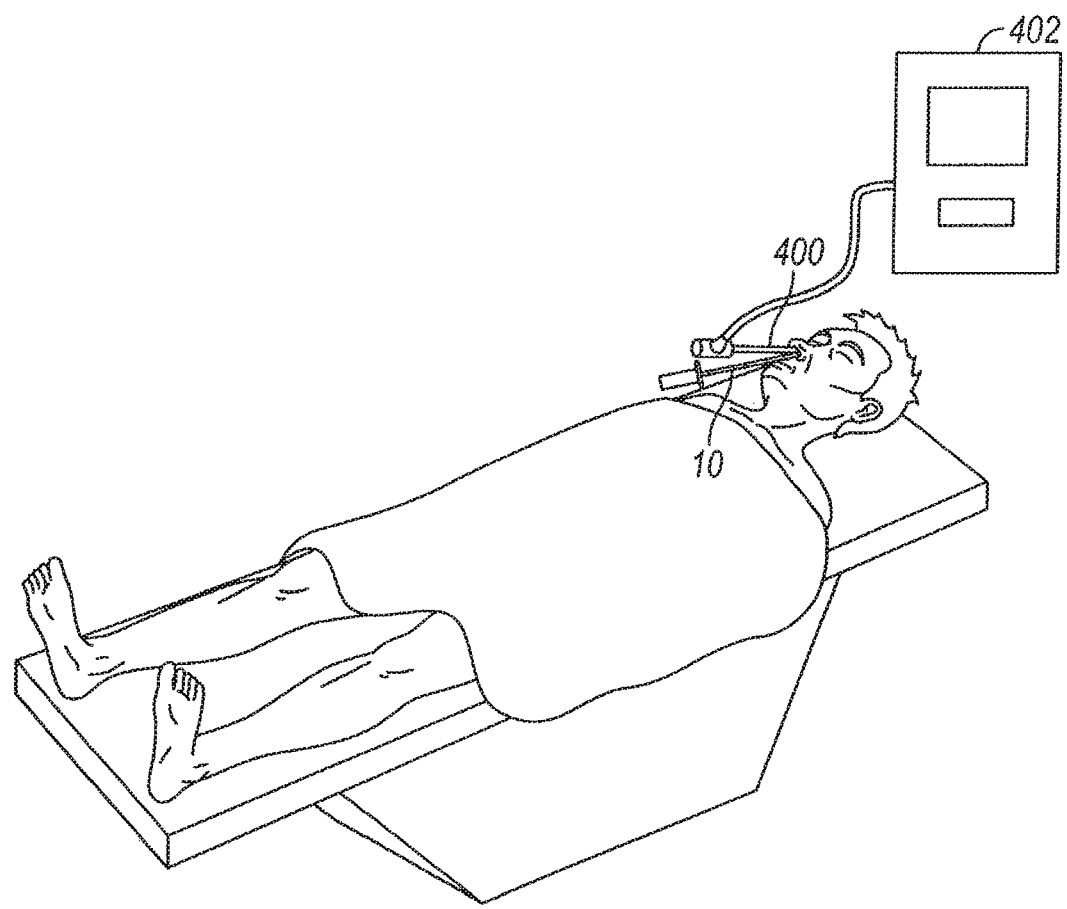
FIG. 1 shows a spacer device of the present invention being used in conjunction with an endoscope to treat a human subject.

FIGS. 1 through 2G show one embodiment of an implantable substance delivery device and/or spacer 10 of the present invention. This device 10 comprises an elongate flexible catheter shaft 12 having a proximal portion 12a and a distal portion 12b which may be severed from one another at separation marker 15. The proximal shaft portion 12a and distal shaft portion 12b may be formed of the same or different materials and may have the same or different dimensions (e.g., diameter, wall thickness, etc.). For example, in some embodiments intended for implantation in paranasal sinuses or other ear, nose or throat locations, the proximal shaft portion 12a may be made of a suitable biocompatible material of sufficient column strength (e.g., pushability) to enable a user to push the substance delivery device 10 into the paranasal anatomy. One such material is polyamide. In some embodiments, the distal shaft portion 12b may be made of a more flexible biocompatible material such as nylon or polyethylene teraphthalate (PET). A lumen 13 extends continuously through the shaft 12. The distal shaft portion 12a may be tapered or necked down to a smaller diameter than the proximal shaft portion to facilitate insertion of the device, as described below. A plug 23 is mounted in the distal end of lumen 13. The plug 23 may comprise any suitable closure member such as a wall of closed end on the tube, an end cap, a mass within the end of the lumen 13 or any other suitable flow blocking member. In the particular example shown in the drawings, the plug 23 comprises a biocompatible polymeric adhesive disposed within the distal end of lumen 13. In some embodiments the plug 23 may include a soft, atraumatic (e.g., bulbous or blunt) tip member that protrudes beyond the distal end of the distal shaft portion 12b.

An expandable reservoir 14 is mounted in a collapsed configuration on the distal shaft portion 12b near its distal end and expands to an expanded configuration as it is filled. Details of one embodiment of such reservoir 14 are seen in FIGS. 2A and 2B as well as 2F, 2G and 2H. In this embodiment, the reservoir 14 comprises a balloon that has a cylindrical side wall wherein openings 31 are formed. The reservoir 14 may be formed of any suitable biocompatible material and, in some embodiments, may comprise a balloon formed of non-compliant or semi-compliant material such as Nylon 12. In at least some embodiments, it is preferable that the material and wall thickness of the reservoir be such that the reservoir is flexible enough to a) allow the device to be extracted and removed from the body without causing significant trauma, b) not force all of the contents of the reservoir to come out at once and c) maintain substantially consistent size of the openings 31 as the reservoir expands. The number of reservoir(s) 14 (such as two or more), the size of the reservoir(s) and the number and size of the openings 31 may vary on the basis of the intended implantation location and/or the potency, viscosity, particle size (for suspensions) and/or other properties of the substance being delivered. For example, in an embodiment of the device 10 intended to be passed through an ethmoidotomy channel and positioned within an ethmoid air cell to treat ethmoid sinusitis, the reservoir 14 may have a length of from about 0.5 cm to about 3.5 cm and typically approximately 2 cm, a diameter when fully expanded of about 0.1 cm to about 0.5 cm and typically approximately 0.3 cm. Also, depending on the substance and the intended elution rate, there may be any suitable number of openings 31. Typically there will be between about 50 and about 5000 openings 31 sized in the range of from about 5 microns in diameter to about 80 microns in diameter.

As described in further below, this embodiment of the reservoir 14 may be inserted, in a collapsed configuration, into a body opening, passageway or cavity (such as, for example, a frontal sinus outflow tract, paranasal sinus ostium, antrostomy, ethmoidotomy opening, or other location within the ear, nose or throat of a subject) and, thereafter, the reservoir may be loaded with the desired substance, causing the reservoir to transition to an expanded state. For example, for applications intended to treat inflammation of a paranasal sinus using the particular reservoir 14 described above with the opening size/pattern seen in FIGS. 2F-2H, the reservoir 14 may be loaded with approximately 0.10 ml of an aqueous suspension containing 40 mg/ml of Triamcinolone Acetonide Injectable Suspension, USP (KENALOG® 40, Bristol-Myers Squibb, Somerville, N.J.). This will cause approximately 100 µg of Triamcinolone Acetonide to elute from the reservoir per day over a period of 14 days. When used for the treatment of fungal sinusitis or other fungal infections, this reservoir 14 may also be used to deliver an antifungal agent such as liposomal or non-liposomal Amphotericin B of 0.3 to 1.5 mg/kg available from Pfizer as AMPHOCIN® anti-fungal. Systemically administered Amphotericin typically has limited distribution from the bloodstream across the mucus membranes and vice versa. With this substance delivery device 10, Amphotericin may be released locally into the mucus membrane where the offending fungal organisms are present and therapeutic concentrations of the drug may remain in the mucus as it is distributed through the sinuses by ciliary action. However, substantial amounts of the Amphotericin will not be substantially absorbed through the sinus mucosa, thereby avoiding the potential for untoward systemic effects of the Amphotericin such as renal toxicity. Also, this reservoir 14 may be capable of delivering solutions as well as suspensions to the surrounding anatomy. This is especially useful for delivery of steroids since most steroids are available as suspensions.

Also, the reservoir 14 need not be used to deliver a therapeutic substance in all applications. It may, in fact, be used as a space occupying device (e.g., instead of a sinus stent). In such applications, the reservoir 14 may be loaded in situ with saline solution of other inert liquid causing the reservoir 14 to expand and frictionally engage or contact adjacent anatomical structure(s), thereby providing a degree of retention at the desired implantation location. This aspect of the reservoir 14 may be further facilitated by the provision of surface projections on the reservoir. In cases where it is intended for the reservoir 14 to function The reservoir 14 may be relatively small in diameter when in its collapsed configuration, thus allowing it to be introduced or removed easily. In embodiments where the reservoir 14 is formed of non-compliant or semi-compliant material, the reservoir 14 will not undergo substantial elastic deformation in the filling process and thus will not exert pressure on its contents in order to expel the desired substance through openings 31. Rather, the substance in the reservoir 14 will be carried out through the openings 31 by gravity or by being in contact with the mucus or blood that is continually moved along by the ciliary action in the sinuses. This non-pressurized delivery allows for the slow release of the desired substance over several days. In some other embodiments, the reservoir 14 may be formed of compliant or elastic material with small openings 31 such that the material of which the balloon 14 is formed will contract as substance passes out of the openings 31, thereby maintaining pressure within the balloon. In cases where the reservoir 14 is intended to be inserted into a sinus ostium, outflow tract, antrostomy opening or ethmoidectomy/ethmoidotomy opening and used to deliver an aqueous suspension containing 40 mg/ml of Triamcinolone Acetonide Injectable Suspension, USP (KENALOG®-40, Bristol-Myers Squibb, Somerville, N.J.) or another substance of similar consistency, the reservoir 14 may have approximately 2200 laser cut openings 31 approximately 20 to 40 microns in diameter formed in the sidewall of the reservoir 14. As seen in FIGS. 2F-2H, the openings 31 may be aligned in longitudinal rows and the positioning of the individual openings 31 may be staggered one row to the next. In this particular example, the longitudinal distance D1 between individual openings is 0.30+/−0.03 mm and the distance D2 between rows is 0.68+/−0.1 mm. Also, in this example, the reservoir has a cylindrical side wall 14a which defines the working length of the reservoir, a distal taper 14b which transitions from the cylindrical side wall 14a to the distal shaft 12b (distal to the reservoir) and a proximal taper 14c that transitions from the cylindrical side wall 14a to the distal shaft 12b (proximal to the reservoir) and the openings 31 extend onto the proximal and distal tapers 14b, 14c, as shown. Also in this example, the reservoir 14 has an overall length of about 16 mm and a working length (i.e., the length of the cylindrical side wall 14c) of about 13 mm and is expandable to a fully expanded diameter of 3.0 to 3.5 mm. Approximately 768 laser cut openings 31 are formed in the side wall 14a of the reservoir 14. The diameter of each laser cut opening 31 is 40 microns. This particular reservoir design, when loaded with 0.31 to 0.35 ml of 40 mg/ml Triamcinolone Acetonide Injectable Suspension, USP (KENALOG®-40, Bristol-Myers Squibb, Somerville, N.J.) will deliver a dose of approximately 100 µg Triamcinolone Acetonide per day for a period of 28 days.

In the particular example shown, the distal shaft portion 12b may be made of Nylon 12 and may have an outer diameter of 0.028 inches, an inner diameter of 0.020 inches and length of 17 mm. An aperture 28 as seen in FIGS. 1B-1C is formed in the catheter shaft 12 to facilitate filling of the reservoir 14. A valve 26 allows the substance (or component (s) of the substance) to flow from the lumen 13 of the catheter shaft 12 into the reservoir 14 (see FIG. 1C) but does not allow substantial backflow from the reservoir 14 into the lumen 13 (see FIG. 1B). The valve 26 may comprise any suitable type of one way valve. In the particular embodiment shown, the valve 28 comprises an elastomeric sleeve valve made of a segment of C-FLEX® thermoplastic elastomer tubing (Consolidated Polymer Technologies, Inc., Clearwater, Fla.).

Optionally, a distal radiopaque marker 24 and proximal radiopaque marker 22 may be provided to facilitate the desired positioning of the reservoir 14 within a subject's body. Each of these markers 22, 24 may be made of a ring of radiopaque material and may be mounted on the shaft 12 in alignment with each end of the reservoir's cylindrical sidewall 14a. In this particular example each marker 22, 24 comprises a band of Platinum-Iridium alloy having outer diameter 0.034 inches and inner diameter 0.030 inches. These markers are visible under various imaging techniques including fluoroscopy and CT scanning.

In the example shown, the proximal shaft portion 12a may be made of polyimide tubing of outer diameter 0.0618 inches and inner diameter 0.052 inches and length 20 cm. A hub 16 comprising a female Luer connector made of clear polycarbonate (Part No. 41519, Qosina, Edgewood, N.Y.) is attached to the proximal end of shaft 12. As seen in FIG. 2C, this hub 16 has a proximal bore 100 that gradually narrows to a distal bore 102, thereby facilitating infusion of suspensions and viscous liquids. The distal bore 102 is approximately the same diameter as, and is continuous with, the shaft lumen 13.

Additionally, in the example shown, the device incorporates two types of position retaining apparatus, namely a suture loop 20 as well as a pair of projections in the nature of retention wings 18. The retention wings 18 are located at diametrically opposed locations on the shaft 12, proximal to the reservoir 14 to help retain the reservoir 14 at a desired position within the body, as will be explained in substantial detail below. In this example, each retention wing 18 comprises a preformed loop of nickel-titanium (nitinol) wire of diameter 0.0086 inches. Each retention wing 18 may be flexed or compressed to a collapsed position where it lies substantially flat against the outer surface of the shaft 12. However, these retention wings 18 are biased to a preformed configuration such that, when unconstrained, each retention wing 18 will resiliently spring outwardly to an extended position wherein it extends at an angle of from about 65 to 90 degrees relative to the longitudinal axis of the shaft 12. Such pre-forming of these wings 18 may be accomplished by heat treating the nitinol wire loop at 520° C. for 20 minutes to produce an austenite finish temperature (Af) of 20° C. Various alternatives to these retention wings 18 may be used. For example, FIG. 3 shows an alternative retaining member 88 comprising proximal and distal resilient elastomeric flanges 90, 92 which are at spaced apart locations so as to rest against and engage opposite sides of an anatomical wall or structure. In FIG. 3, the anatomical wall or structure comprises a bulla or sinus wall formed of bone B covered by mucosal tissue M. The distal flange 88 is sufficiently resilient and flexible to collapse while passing through the small opening in the anatomical wall and to thereafter resume its expanded shape as seen in FIG. 3.

The suture loop 20 (e.g., an eyelet or ring) may be formed of supple, flexible, resilient, elastic or superelastic material such as suture thread or nickel-titanium alloy (Nitinol) wire. In the particular embodiment shown, the suture loop is formed of black monofilament Nylon non-absorbable surgical suture material having a diameter of 0.0075 inches. The suture loop 20 may be collapsed against the outer surface of shaft 12. The suture loop 20 may be affixed to the outer surface of shaft 12 by winding the wire or other material around the shaft and securing the wire to the shaft using a suitable adhesive such as cyanoacrylate, epoxy or UV curable adhesive and/or by mounting a polymeric sleeve or heat shrinkable member about the portions of wire that are wound around the shaft 12. In some embodiments, the suture loop may be colored so as to be visually distinguishable from blood and the red-pink color of the intra-nasal mucosa. For example, the suture loop 20 may be black, bright blue or green in color so as to be easily locatable by the surgeon. This suture loop 20 may be sutured to the adjacent tissue to anchor the distal portion of the device 10 in place.

As seen in FIGS. 2D and 2E, a tubular constraining sheath 30 may be positioned over the shaft 12. In the particular example shown, this constraining sheath 30 comprises a 10 cm length of plastic tubing having an outer diameter of 0.084 inches and an inner diameter of 0.075 inches. This constraining sheath 30 is moveable back and forth between a retracted position (seen in FIG. 2D) and an extended position (seen in FIG. 2E). When in the extended position, the constraining sheath extends over the retention wings 18, suture loop 20 and the collapsed reservoir 14, thereby holding the retention wings 18 in their collapsed positions and forming a smooth protective covering over the retention wings 18, suture loop 20 and collapsed reservoir 14. Also, when in the extended position, the constraining sheath 30 will add column strength to the over all device and will deter kinking of the shaft 12 as it is pushed through relatively narrow and/or tortuous anatomical passages. After the device 10 has been inserted to the desired position, the constraining sheath 12 may be withdrawn to its retracted position, thereby allowing the suture loop 20 to be accessible, the retention wings 18 to spring outwardly to their extended positions and the reservoir 14 to undergo expansion when it is subsequently loaded with the desired substance.

Figure 19:
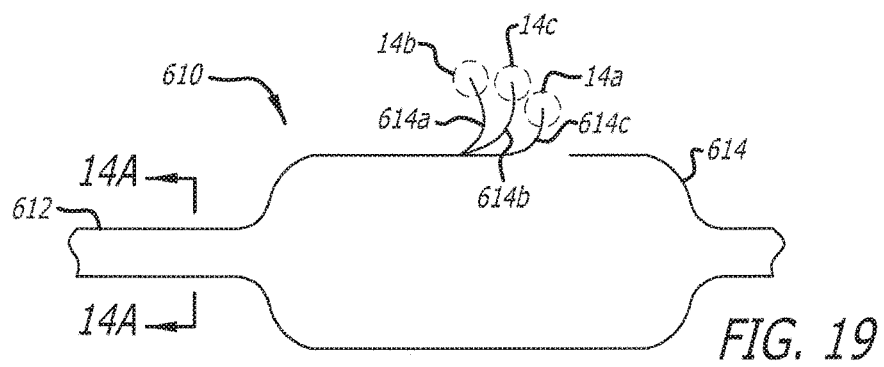
FIGS. 19 and 19A-19D are various views of another embodiment of a substance delivering spacer device of the present invention incorporating a multi-layer expandable reservoir.
Figure 19A:
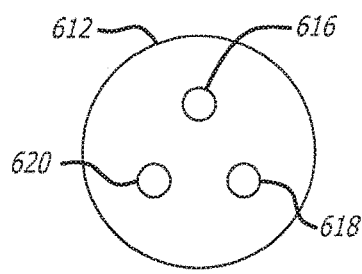
Figure 19B:
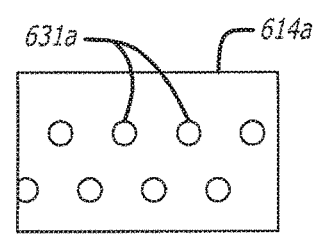
Figure 19C:
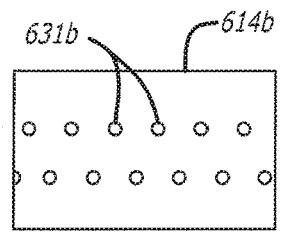
Figure 19D:
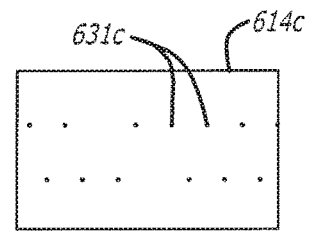

Although the particular examples of the spacer device 10 described above include a reservoir 14 formed of a single layer balloon, in some embodiments, the reservoir may comprise a balloon having multiple layers with different sized openings in each layer. The substance may then be selectively introduced between the particular layers that will facilitate the desired delivery of that particular substance at the desired rate. In this regard, by way of example, FIGS. 19 through 19D show another embodiment of a substance delivering spacer device 610 having a shaft 612 and a multi-layered reservoir balloon 614. The shaft 612 may be constructed and equipped in the same manner as the shaft 12 of the device 10 described above. However, in the embodiment three lumens 616, 618 and 620 extend through the shaft 612 and the reservoir 614 comprises a balloon having three layers 614a, 614b and 614c. The outermost layer 614a has openings 631a of a first size. The middle layer 614b has openings 631b of a second size that is smaller than the size of the openings 631a formed in the outer layer 614a. The inner-most layer 614c has openings 631c of a third size that is smaller than the size of the openings 631b formed in the middle layer 614b. First lumen 616 opens into the space within the innermost layer 614c. Second lumen 618 opens into the space between the inner-most layer 614c and the middle layer 614b. Third lumen 620 opens into the space between the middle layer 614b and the outer-most layer 614a. In this manner, the operator may select the particular space into which a particular substance is to be infused so that the substance will be required to pass through either: a) only the openings 631a in the outer-most layer 614a; b) the openings 631b in the middle layer 614b as well as the openings 631a in the outer layer 614a; or c) all of the openings 631a, 631b, 631c in all three layers 614a, 614b and 614c. In this manner, the rate of elution of the substance may be optimized.

As will be described in more detail below, the substance delivering spacer device 10, 610 may be implanted in any suitable part or location of the body of a human or animal subject to perform a spacing function (e.g., to prevent tissue ingrowth, scarring, fibrosis, adhesion formation, etc.) and/or to deliver any desired therapeutic substance. For example, in ear, nose and throat applications the device 10, 610 may be implanted in a natural ostium or man-made opening formed in any paranasal sinus or air cell or in any other natural, surgically modified or surgically created opening or passageway, such as the outflow tract of a frontal sinus, the inferior, superior or medial meatus, etc.

Figure 4:
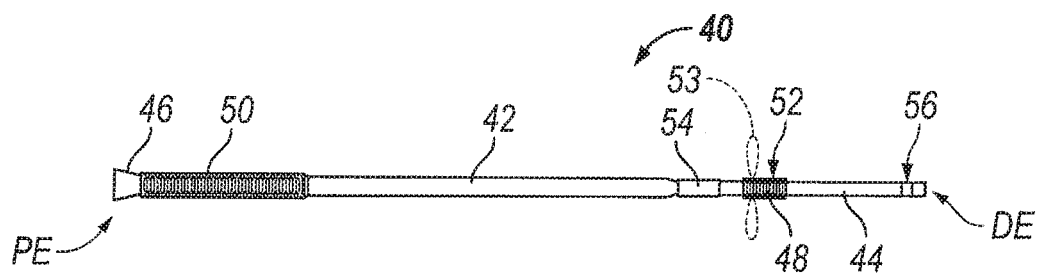
FIG. 4 is a side view of one embodiment of a sheath that is useable in conjunction with an ethmoidotomy needle of the present invention.
Figure 5:
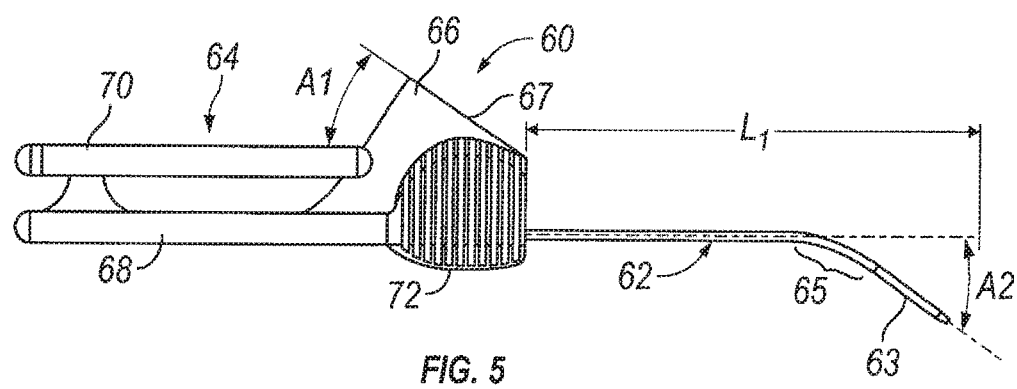
FIG. 5 is a side view of one embodiment of an ethmoidotomy needle device of the present invention.
Figure 6:
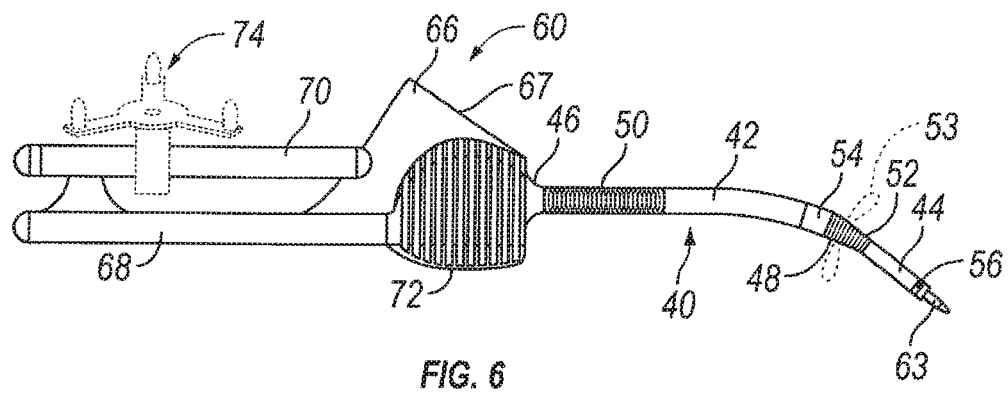
FIG. 6 is a side view of the ethmoidotomy needle device of FIG. 5 with the sheath of FIG. 4 positioned thereon.
Figure 5A:
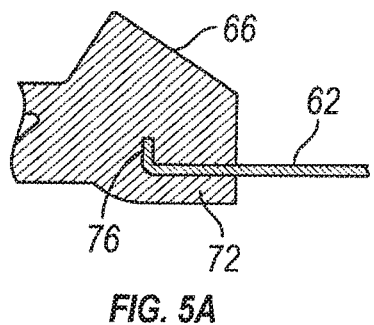
FIG. 5A is a longitudinal sectional view through a distal portion of the handpiece of the ethmoidotomy needle device of FIG. 5.
Figure 5B:
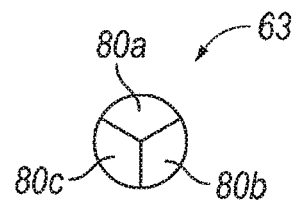
FIG. 5B is a distal end view of the ethmoidotomy needle device of FIG. 5.
Figure 5C:
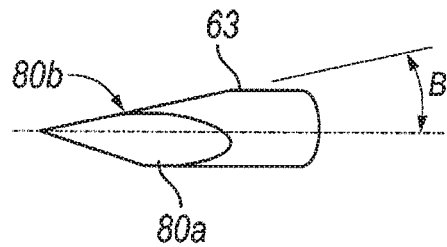
FIG. 5C is a side view of the distal tip of the ethmoidotomy needle device of FIG. 5.
Figure 5D:
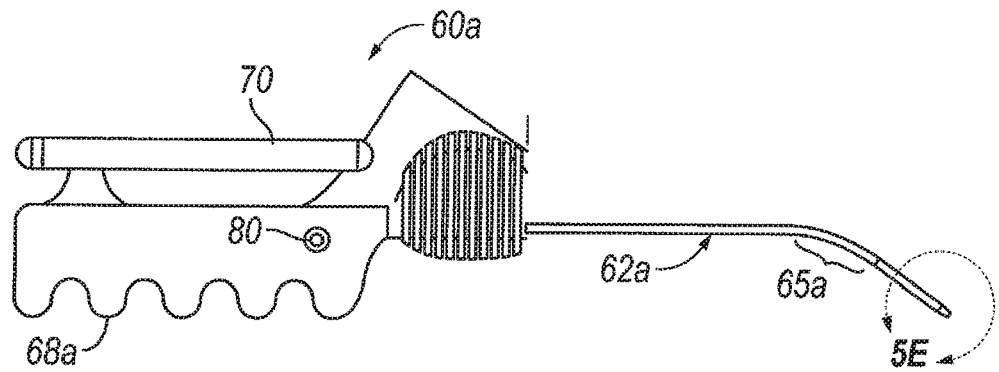
FIG. 5D is a side view of another embodiment of an ethmoidotomy device of the present invention incorporating a rotating burr tip.
Figure 5E:
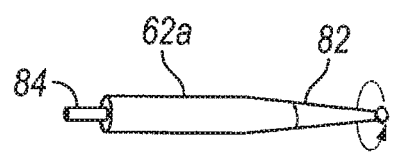
FIG. 5E is an enlarged side view of the rotating burr tip of the ethmoidotomy device of FIG. 5D.

FIGS. 4-5E show an example of an ethmoidotomy system that may be used separately or in conjunction with a substance delivering spacer device 10, 610 of the type described above. This ethmoidotomy system comprises a sheath 40 seen in FIG. 5 and a sinus needle 60 seen in FIG. 6. The sheath 40 and sinus needle 60 may be used separately or in combination. The combination of the sheath 40 and sinus needle 60 is shown in FIG. 6.

The sheath 40 may be formed of a biocompatible polymer such as PEBAX and comprises a proximal sheath body 42 of a first diameter, a distal sheath body 44 of a second diameter (smaller than the first diameter) and a tapered step-down segment 54 between the proximal sheath body 42 and the distal sheath body 44. A flared region 46 is located at the proximal end PE of the sheath 40. A visual marker band 50 is optionally provided on the proximal sheath body 42 near its proximal end PE. A second visual marker band 48 is optionally located on the distal shaft portion 44 approximately 17 mm from the distal end DE. Also optionally, radiopaque markers 52, 56 may be provided at spaced apart locations on the distal sheath body 44. In the particular example shown, the distal radiopaque marker 56 is located approximately 1.5 mm from the distal end and the proximal radiopaque marker 52 is located approximately 17 mm from the distal end DE and beneath the distal edge of visual marker 48. Additionally, in some embodiments, optional wing members 53 may extend laterally from the distal sheath body 44 in the region of visual marker 48. These optional wing members 53 may be constructed in substantially the same manner as the retention wings 18 of the substance delivering spacer device 10 described above and, when extended, each wing member 53 may have a length of about 2 cm. These optional wing members 53 will abut against adjacent an adjacent anatomical structure to limit the distance through which the sheath 40 may be advanced through an opening or channel within the body. This sheath 40 may be used to facilitate insertion of the above-described substance delivering spacer device 10 or this sheath 40 may be used alone to facilitate suctioning of matter or for delivery of therapeutic or diagnostic substances.

In the embodiment shown in FIG. 5, the sinus needle 60 comprises an elongate, curved needle body 62 having a sharp trocar tip 63. The proximal end of the needle body 62 is firmly, non-rotatably anchored to handpiece 64. As seen in FIG. 5A, this may be accomplished by forming a 90 degree bend in the proximal end of the needle body 62 and molding it in place within the handpiece 64 thereby providing a strong connection and preventing the needle body 62 from rotating relative to the handpiece 64. In the embodiment shown in the drawings, the needle body 48 is formed of solid stainless steel wire having an outer diameter of approximately 0.07 inches. A curve 65 is formed in the needle body 62. The needle body 62 is about 102 mm in length and the center of the curve 65 is located about 31 mm from the distal tip 63 of the needle body 62. The curve 65 forms an angle A2 of approximately 33 degrees. This particular embodiment of the sinus needle 60 is particularly suited for a needle ethmoidotomy as described below and the curve 52 allows the distal portion of the needle body 62 to be advanced through the ethmoid bulla and into the ethmoid air cells with decreased potential for inadvertent penetration through the adjacent skull base which protects the subject's brain. Also, as indicated in the enlarged views of FIGS. 5B and 5C, in this example the trocar tip 63 has three bevelled edges arranged symmetrically around the central axis of needle shaft with each bevelled edge being disposed at an angle B of about 20 degrees relative to the longitudinal axis of the needle body 62. This design enables sinus needle device 60 to be used for penetration through soft tissue (e.g., mucosa) as well as thin bone (e.g., the ethmoid bulla and other bones separating individual ethmoid air cells.

The handpiece 64 comprises a sighting member such as a fin 66, a top elongate member 70 and a bottom elongate member 68 that is attached to and substantially parallel to the top elongate member. The handpiece may also comprise a distal grip portion 72. All or part of the handpiece 64 may be coated with an elastomeric material and/or may be provided with grooves, ridges or surface configurations that facilitate firm grasping of the handpiece 64 by the operator.

The sighting fin 66 extends from the handpiece in a plane that is parallel to the plane of the needle curve 65, thereby providing to the operator a visual indication of the lateral direction in which the distal portion of the needle body 62 is advancing even when the distal end of the needle body 62 is within the subject's body and out of direct sight of the operator. Additionally, the top edge 67 of the vertical sighting fin 66 is parallel to and in substantial alignment with the distal portion of the needle body 62, thereby providing to the operator a visual indication of the vertical tilt or trajectory on which the needle tip 63 is advancing even when the distal end of the needle body 62 is within the subject's body and out of direct sight of the operator.

FIG. 6 shows the needle sheath 40 positioned on the sinus needle body 62. As shown, the length of the needle sheath 40 is such that when the sheath 40 is fully advanced onto the needle body 62, the flared region 46 located at the proximal end PE of the sheath 40 will abut against the distal surface of the handpiece 64 and the distal tip 63 of the needle body 62 will protrude out of and beyond the distal end DE of the sheath 40. The sheath 40 is flexible enough to conform to the curve 65 of sinus needle body 62, as shown. Optionally, for some applications, an optical or electrical image guidance component 74 (e.g., sensors, reflectors, light sources, etc.) may be attached to the upper elongate member 70 of the handpiece 64, as seen in FIG. 6, thereby allowing an optical or electromagnetic image guidance system to be used, in accordance with techniques well known in the art of ear, nose and throat surgery, to determine and/or guide the positioning of the needle tip 63 within the body of human or animal subject.

U.S. Pat. No. 5,314,417 entitled "Safety Trocar" and U.S. Pat. No. 5,267,965 entitled "Safety Trocar", the entire disclosures of which are incorporated herein by reference, disclose safety mechanisms that may optionally be used in combination with the sinus needle device 60 and sheath 40.

As an alternative to a needle body 63 having a sharp tip such as a trocar tip 63, the sinus needle may comprise any other suitable tissue penetrating apparatus capable of forming the desired penetration through the intended tissue (e.g., for ethmoid applications, through mucosal tissue and bone). These other suitable tissue penetrating apparatus include but are not limited to rotating drills, burs, bipolar or monopolar radiofrequency or electrocautery probes, laser probes, etc. FIGS. 5D and 5E show one example of an alternative sinus penetrator 60a which is similar in construction to the sinus needle 60 described above except that the bottom elongate member 68 of the handpiece is replaced by a housing 68a having an electric motor (not shown) positioned therewithin and an on-off button. Also, in this device, the needle body 62 is replaced by a rotating bur assembly which comprises an elongate curved tube 62a having a flexible rotating drive shaft 84 extending therethrough and a rotating burr tip 82 attached to the distal end of the drive shaft 84, as shown in FIG. 5E. Because the drive shaft 84 is flexible, it is capable of rotating even though it extends through the curve 65a of the tubular body 62a. The rotating burr tip may be a 0.6 mm, 0.7 mm or 0.8 mm diamond bur tip and the motor, drive shaft 84 and bur tip 82 may be substantially the same as used in the ULTRABUR™ Fixed Tip Drill (Invotec International, Inc., Jacksonville, Fla.).

In other alternative embodiments where the needle 62 is replaced by a laser probe, a fiber optic laser waveguide may extend through the probe and a suitable type of laser light may be delivered through the wave guide and out of the distal end of the probe to penetrate through the desired anatomical structure. For penetration through the ethmoid bulla or other soft tissue or bony paranasal structures one suitable type of laser is a holmium:YAG laser. See, Metson, Ralph; Holmium:YAG Laser Endoscopic Sinus Surgery: A Randomized, Controlled Study; Laryngoscope; 106(1) Supplement 77:1-18 (January 1996).

Treatment of Ethmoid Sinusitis by Needle Ethmoidotomy and Implantation of Substance Delivering Spacer Device with Sustained Corticosteroid Delivery FIGS. 7A-7K show one example of a method by which the above-described sinus needle device 60, sheath 40 and substance delivery device 10 may be used to perform a needle ethmoidotomy, to effectively "stent" the ethmoidotomy channel and to deliver a therapeutic substance (e.g., a corticosteroid) into the diseased ethmoid sinuses for a period of time postoperatively.

Figure 7A:
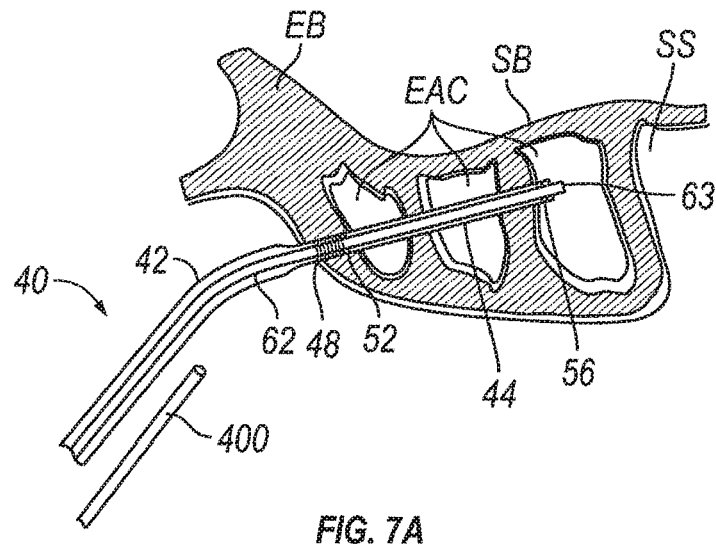
FIGS. 7A-7K show steps in a method for performing an ethmoidotomy and implanting a substance delivering spacer device in accordance with the ethmoidotomy channel in accordance with the present invention.

Initially, as seen in FIG. 7A, the needle sheath 40 is placed on the needle body 62 as shown in FIG. 6. In this embodiment, the inner diameter of the proximal sheath portion 42 is large enough to allow the constraining sheath 30 of the substance delivery device (shown in FIGS. 1D and 1E) to pass therethrough, whereas the internal diameter of the distal sheath portion 44 is the same or smaller than the outer diameter of the moveable sheath 30 but still sufficiently large in diameter to allow the collapsed reservoir 14 and non-deployed retention wings 18 to pass thereinto.

Figure 18:
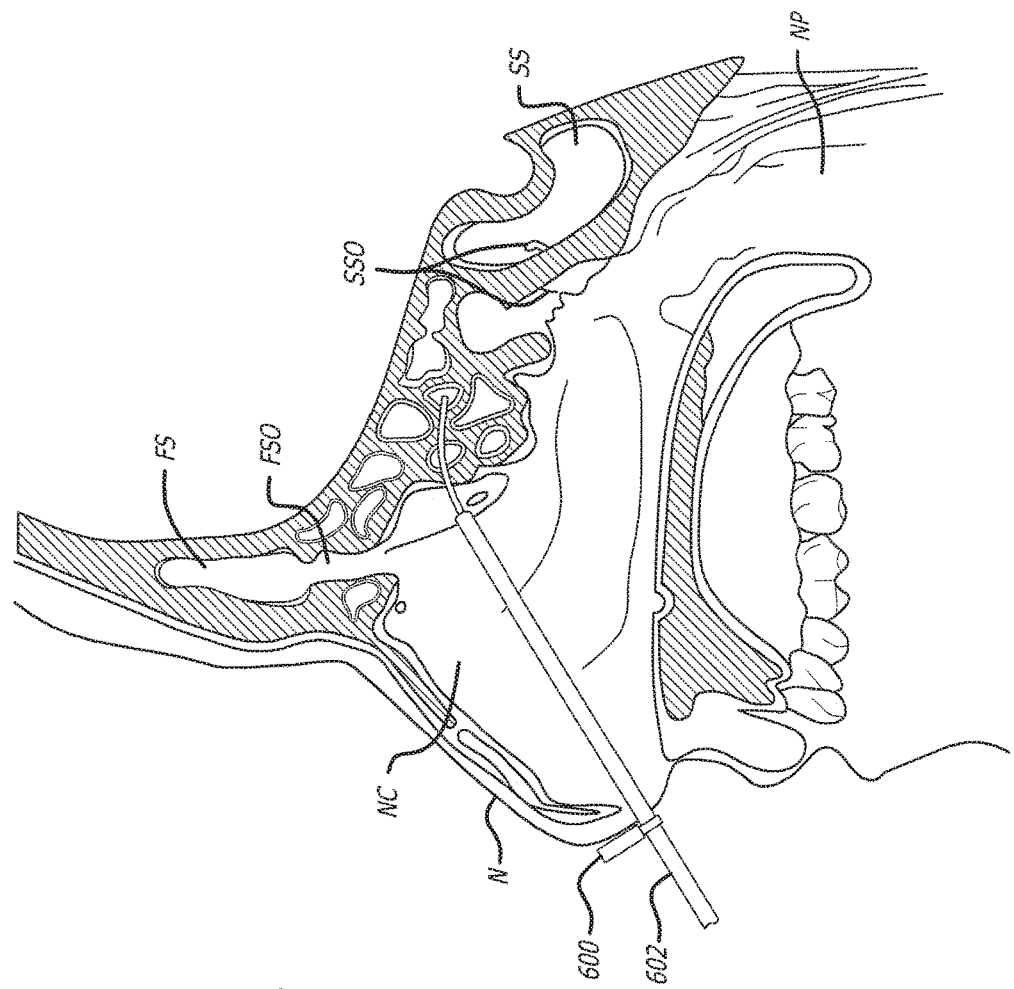
FIG. 18 is a partial left/right sagittal section of a human head showing an ethmoidotomy needle having a depth controlling stop member inserted through the subject's nostril and advanced into the ethmoid sinuses until the stop member has abutted against the subject's nose, thereby preventing further advancement of the needle.

The subject is anesthetized or appropriate analgesia/sedation is administered. As shown in FIG. 7A, the needle body 62 having the sheath 40 mounted thereon is inserted through the subject's nostril along with an endoscope 400 such as a STORZ HOPKINS™ II, 0 degree, autoclavable 4 mm.times.18 mm telescope with a STORZ XENON 300™ or XENON NOVA™ light source (Karl Storz GmbH & Co., Tuttlingen, Germany). Also, in this example, a C-arm fluoroscope system may optionally be used to provide fluoroscopic images during portions of the procedure. One example of a commercially available C arm fluoroscope system that is suitable for this purpose is the OEC 9800 PLUS™ Digital Mobile Imaging System (G.E. OEC Medical Systems, Inc., Salt Lake City, Utah). The operator may verify that the distal portion of the needle body 62 is in the proper vertical tilt and lateral direction by viewing the sighting fin 66 and its leading edge 67. Under endoscopic guidance, the needle tip 50 is pushed through the ethmoid bulla EB and into one or more ethmoid air cells EAC. The approximately thirty-three degree angle 65 formed in this embodiment of the sinus needle body 62 allows the distal tip 63 to be advanced on a trajectory that is substantially parallel to (or in some cases even divergent from) the adjacent skull base SB. In this regard, when the procedure is performed on an adult human, the curve 65 of the ethmoidotomy needle body 62 may have a radius of about 0.75 inch and may form an angle A of about 33 degrees. The distal portion of the needle body 62 (i.e., the portion extending from the curve 62 to its distal tip 63) has a length of about 24 mm, thereby allowing for ease of maneuvering the needle/sheath assembly and allowing it to be inserted along side an endoscope 400 with the endoscope 400 being above or below the needle/sheath assembly. The ethmoidotomy needle body 62 is formed of a 0.073" diameter 304 stainless steel wire having a measured tensile strength (ASTM A313-03) in the range of about 253852 to 258665 psi. In cases where an image guidance component 74 is attached to the handpiece 64 of the sinus needle device 60, the operator may additionally use known techniques and apparatus for optical or electromagnetic image guidance of the advancement of the sinus needle body 62 relative to the skull base SB and other critical anatomical structures. Also, the depth of penetration must be carefully controlled so as not to penetrate all the way though the sphenoid wall and into the sphenoid sinus SS. To ensure that the sphenoid wall is not breached, the surgeon may choose a sheath 40 wherein the distance from the distal end DE of the sheath 40 to the proximal edge of visual marker 48 is less than the distance from the anterior surface of the ethmoid bulla EB to the wall of the sphenoid sinus SS. The distal visual marker 48 on the sheath 40 may then be visualized via the endoscope to gage the depth of penetration into the ethmoid air cells. The advancement may be stopped when the proximal end of visual marker 48 is seen to be flush with the ethmoid bulla EB, thereby ensuring that the sphenoid wall has not been breached. Also, if the sheath 40 incorporates the optional wing members 53, the device may be advanced until those wing members 53 abut against the anterior surface of the ethmoid bulla EB. Additionally, as seen in FIG. 18, an optional external stop member 600 may be attached by any suitable means, such as a clip 602, grasper, adhesive, frictional engagement or any other means, to the sheath 40 at a location which will cause the stop member 600 to abut against the subjects nose, thereby preventing the needle 62 and sheath 40 from being advanced beyond a safe distance into the ethmoids. The distance between the proximal and distal radiographic markers 52, 56 is substantially the same as the length of the reservoir 14 and such markers 44 may be viewed by fluoroscopy. The surgeon can use such fluoroscopic image to position the markers 52, 56 such that they demarcate the locations where the proximal and distal ends of the reservoir 14 are intended to reside.

Figure 7B:
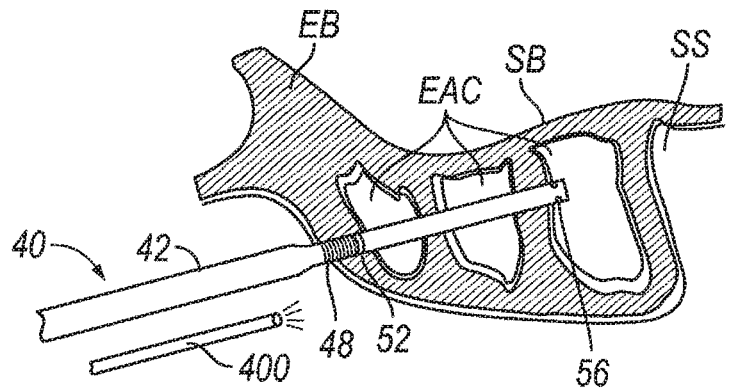

As shown in FIG. 7B, after the sheath 40 has been placed in the desired position, the needle 49 is withdrawn leaving the sheath 40 in place, with the proximal end of the sheath 40 extending out of the subject's nostril.

Figure 7C:
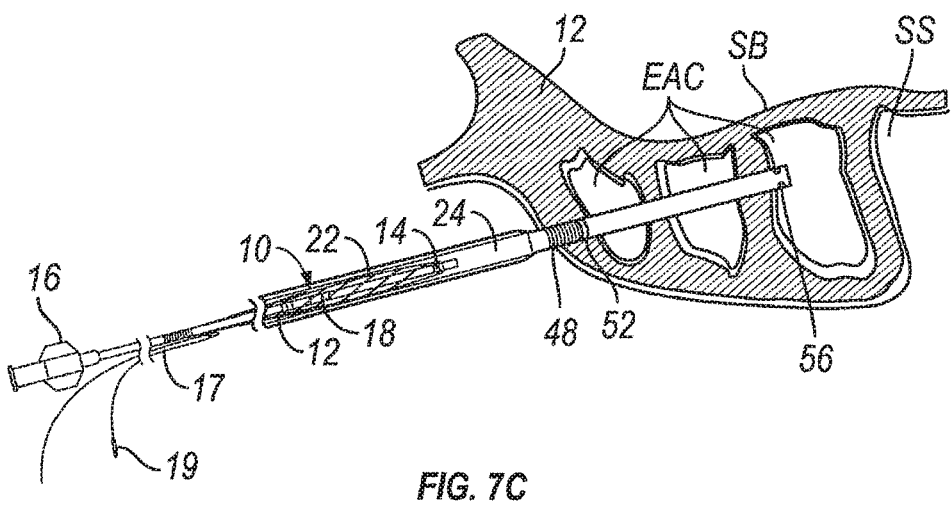

Prior to insertion of the substance delivering spacer device 10, the physician may optionally retract the constraining sheath 30 to expose suture loop 20, and a length of 2-O or 3-O suture material 17 having a straight or curved needle 19 may be passed through suture loop and doubled over. The constraining sheath 30 may then be moved to its advanced position, and the opposite ends of the doubled over suture 17 will be caused to protrude out of the proximal end of the constraining sheath 30 as shown in FIG. 7C. The substance delivery device 10 with its reservoir in a collapsed state and the constraining sheath 30 in its advanced position (as shown in FIG. 2E) is then inserted into the proximal end of the needle sheath 40 as seen in FIG. 7C.

Figure 7D:
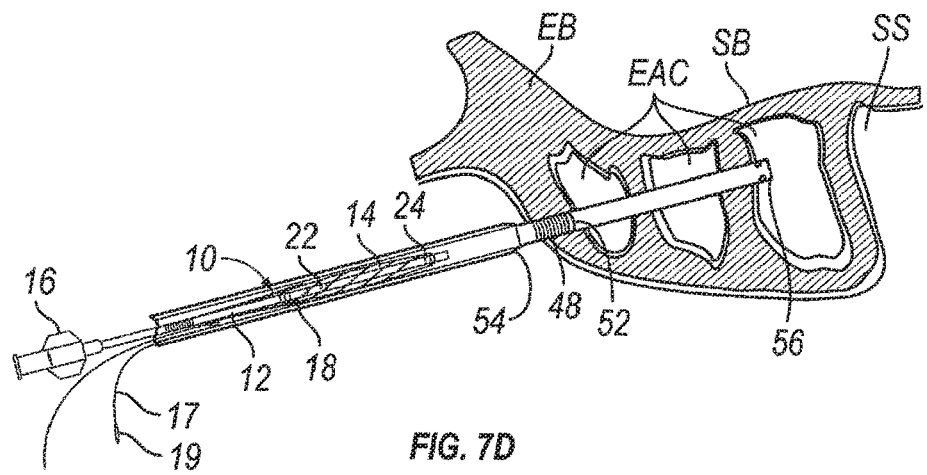

Thereafter, as seen in FIG. 7D, the substance delivery device 10 with the constraining sheath 30 in its advanced position is advanced through the sheath 40 to a position where slight resistance to further advancement is felt due to abutment of the distal end of the constraining sheath 30 with the narrowed wall of the internal surface of the tapered segment 54.

Figure 7E:
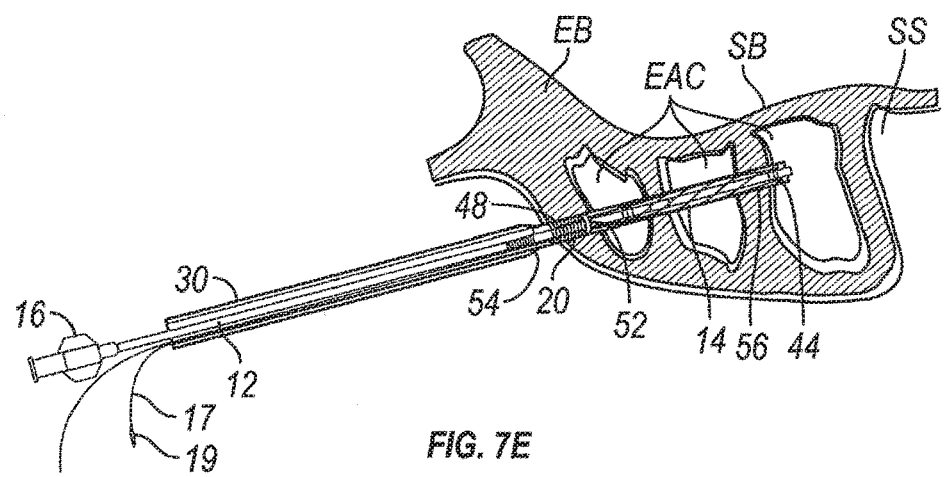

Thereafter, as shown in FIG. 7E, the surgeon will apply sufficient force to overcome the resistance to advancement, causing the constraining sheath 30 to move proximally to its retracted position (shown in FIG. 2D) as the distal portion of the substance delivering spacer device 10, including the collapsed reservoir 14, advances into the distal sheath portion 42. The positioning of the reservoir 14 within the distal sheath portion 42 may then be verified fluoroscopically by viewing the positions of the radiographic marker 24 on the device 10 relative to the positions of the radiographic markers 44 on the distal sheath portion 42. Also, using these markers, the actual positioning of the reservoir 14 relative to the surrounding anatomy may be checked.

Figure 7F:
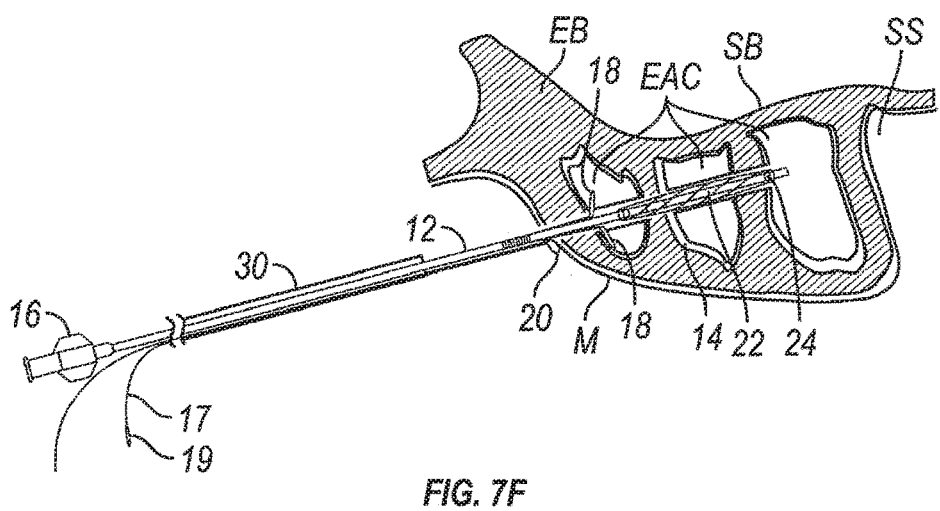

Thereafter, as shown in FIG. 7F, the sheath 40 with the constraining sheath 30 contained therein may be withdrawn proximally. This allows the retention wings 18 to spring outwardly and engage the adjacent septal walls between ethmoid air cells EAC or alternatively the internal wall surface of the ethmoid bulla EB. The deployment and engagement of the retention wings 18 may be verified fluoroscopically. This also allows the suture loop 20 to be exposed within the nasal cavity adjacent to the ethmoid bulla EB. Because the suture loop is colored differently from blood and the surrounding mucosa, the exposure of the suture loop may also be verified endoscopically.

Figure 7G:
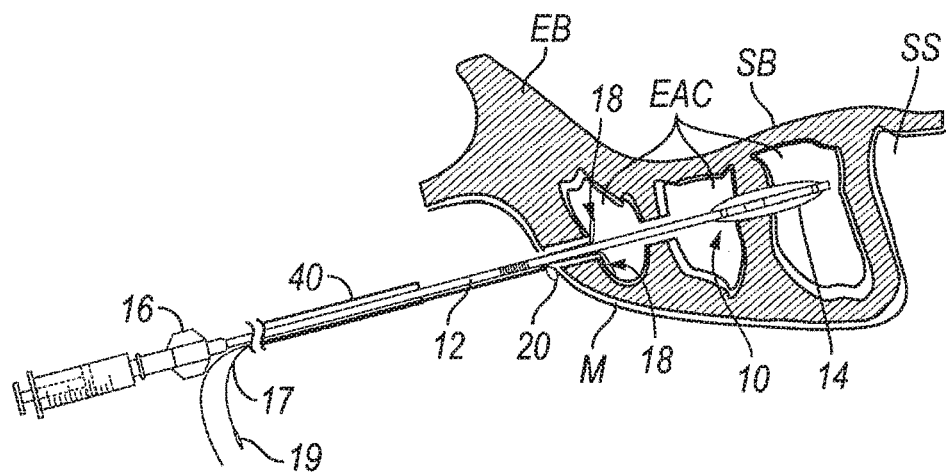

Thereafter, as seen in FIG. 7G, a syringe containing 0.31 cc to 0.35 cc of Triamcinolone Acetonide injectable suspension (KENALOG® 40, Brystol-Myers Squibb Company, Princeton, N.J.) is attached to the proximal Luer connector 16 of the substance delivering spacer device 10 and the Triamcinolone Acetonide injectable suspension is injected, thereby causing the reservoir 14 to expand. In some embodiments, the shaft 12 of the substance delivering spacer device 10 may be transparent so that the delivery of the substance through lumen 13 may be viewed through the endoscope 400.

Figure 7H:
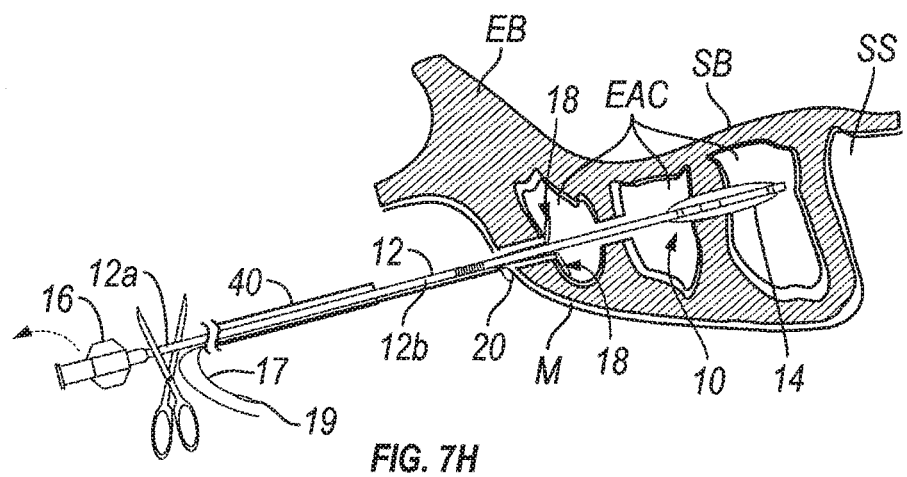

Thereafter, as shown in FIG. 7H, the shaft 12 adjacent to proximal Luer connector 16 is cut thereby removing the Luer hub 16. This allows the sinus needle sheath 42 with the constraining sheath 30 contained therein to be removed, thereby freeing the suture 17 and needle 19 for suturing to an anatomical structure adjacent to the suture loop 20. Alternatively, in some embodiments, the sheath 40 can be provided with a longitudinal perforation or weakened region which will allow the sheath to be peeled away and removed.

Figure 7I:
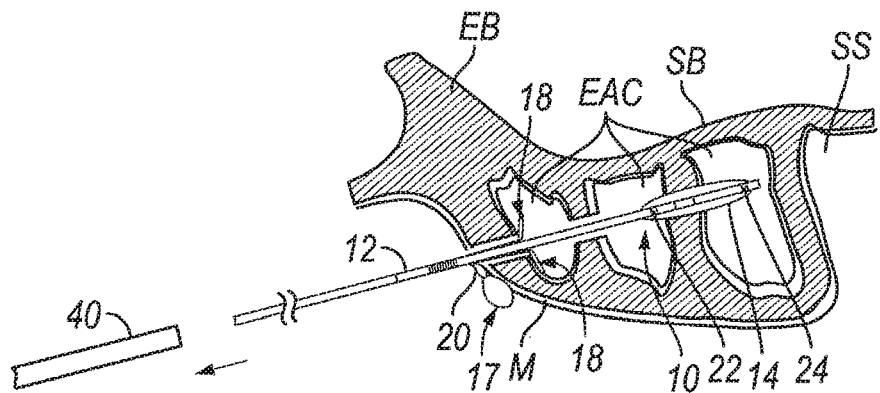

As seen in FIG. 7I, the sinus needle sheath 40 with the constraining sheath contained therein is removed and the suture 17 is used to attach suture loop 20 to adjacent tissue, such as the mucosa M of the intranasal septum or that covering the nasal surface of the ethmoid bulla EB.

Figure 7J:
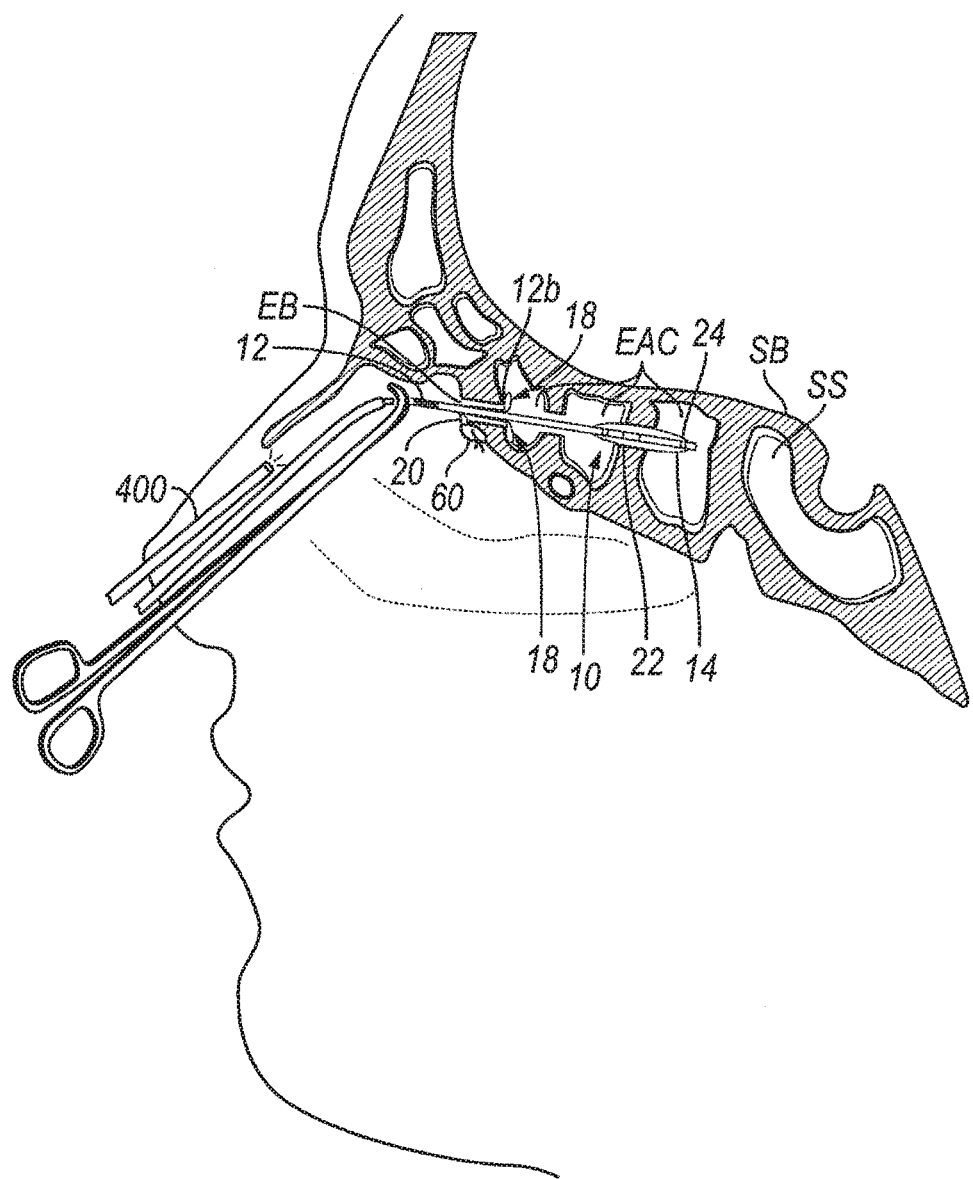

Thereafter, as seen in FIG. 7J, the shaft 12 is cut at or distal to separation mark 15, and the proximal shaft 12a is removed.

Figure 7K:
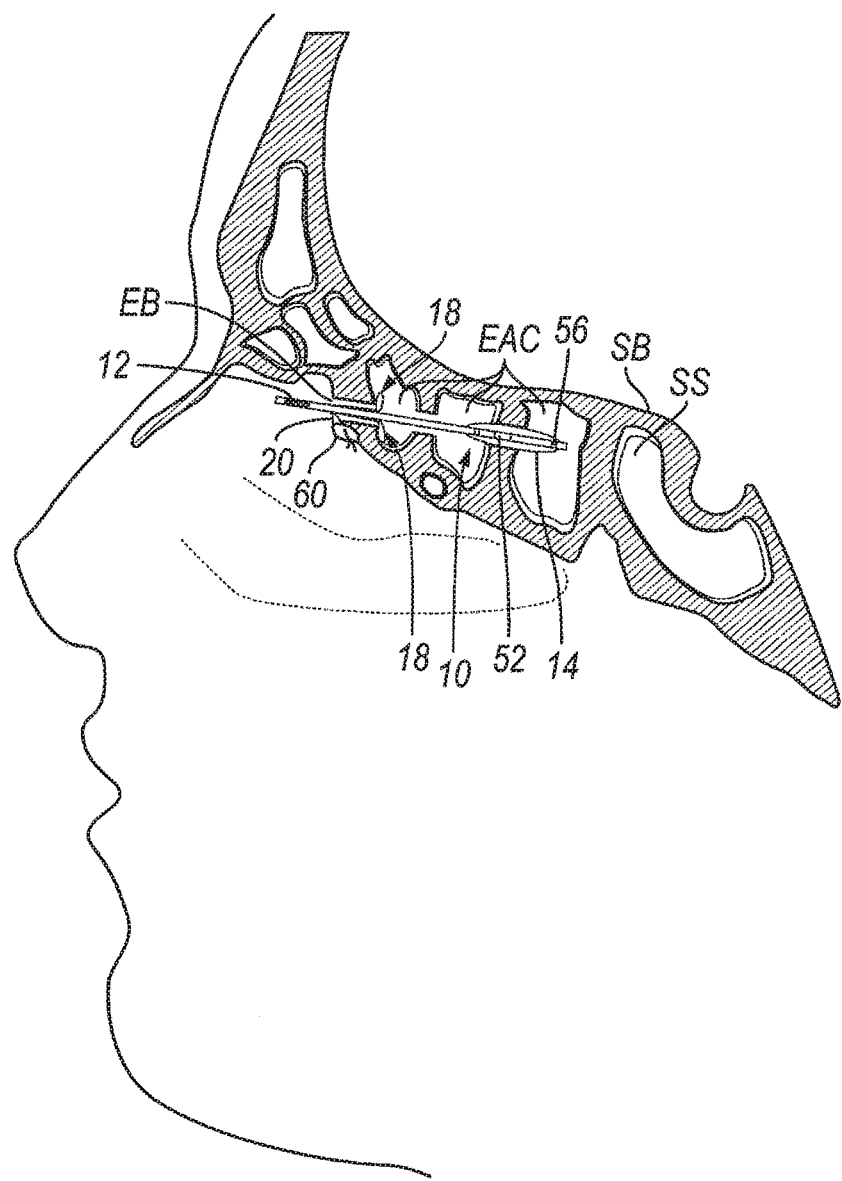

As seen in FIG. 7K, this procedure results in an ethmoidotomy channel or opening extending into one or more ethmoid air cell(s) EAC with the substance eluting reservoir 14 and distal shaft 12b remaining in place for a period of time (e.g., between 1 hour to 90 days, preferably between 7 to 29 days, most preferably about 14 days and in some cases about 7 days) following the performance of the needle ethmoidotomy procedure. Additionally, a small amount of the substance will remain in the distal shaft 12b distal to the location at which it is cut. This remaining substance may slowly leak out of the cut end of the distal shaft 12b thereby providing medication to adjacent turbinate or other nearby anatomical structures within the nasal antrum.

In this ethmoid example, the sinus needle sheath 40 has a distal shaft portion 44 made of Nylon having an outer diameter of 0.087 inches and inner diameter of 0.075 inches and length of 25 mm. Intermediate tapered region 54 is about 5 mm in length and is tapered from an outer diameter of 0.104 inches and an inner diameter of 0.088 inches at its proximal end, to an outer diameter of 0.092 inches and an inner diameter of 0.075 inches at its distal end. Proximal shaft portion 42 is made of Nylon 12 and has an outer diameter of 0.102 inches and inner diameter of 0.088 inches and length of 3.5 inches. Distal and proximal sheath markers 44 are made of rings of a Pt—Ir alloy with an outer diameter of 0.087 inches and an inner diameter of 0.085 inches. The distal shaft marker 44 is located 1 mm from the distal end DE of needle sheath 134. Proximal shaft marker 148 is located 18 mm from the distal end of needle sheath 40. The total length of needle sheath 40 is 115 mm.

Although the example of FIGS. 7A-7K is specific to treatment of ethmoid disease, the system of devices shown in the example of FIGS. 3A-3L may also be used to form penetration tracts or openings (e.g., antrostomy openings, etc.) in various paranasal sinuses and other anatomical structures and to position the substance delivering spacer device 10 within such penetration tracts or openings. Additionally, the substance delivering spacer device 10 may be used separately from the sinus needle device 60 in various ostia, openings, incisions and passageways of the body to act simply as a spacer and/or to deliver a desired diagnostic or therapeutic substance. In the treatment of sinus disease, steroids such as KENALOG® 40 (Triamcinolone Acetonide Injectable Suspension, USP) are delivered to a paranasal region such as the ethmoid sinuses with device 10.

The implantable device 10 can be used to preferably deliver fluids or suspensions with a low surface tension. Fluids with low surface tension easily spread across a surface. This is especially useful to deliver substances over a large surface area, especially in anatomical regions such as ethmoid sinuses that have complicated 3-D geometries. In one embodiment, the low surface tension fluid comprises a surfactant. In one method embodiment, a low surface tension irrigating fluid containing one or more substances is delivered to the ethmoid sinuses. In some embodiments, a substantially inert fluid such as saline solution may be delivered to moisten the surrounding tissues and the device may perform a spacing and/or drainage/ventilation function. In other embodiments, an active substance such as a therapeutic or diagnostic substance may be delivered in addition to the spacing and/or drainage/ventilation function of the implanted device 10.

In some applications, the substance delivering spacer device 10 may be implanted within openings (e.g., natural ostia, surgically altered ostia, other man-made openings) of paranasal sinuses to facilitate the treatment of a disease or disorder affecting the paranasal sinus. In such applications, the opening of the paranasal sinus may be enlarged (e.g., dilated) before or after placement of a device 10, 104 of the present invention within such opening. One such procedure is balloon dilation of sinus cavity ostia. In such procedure, a guide catheter having a substantially fixed shape is inserted through the nose and advanced to a position where the distal end of the guide catheter is adjacent to the ostium of a paranasal sinus. A guidewire is then advanced through the guide catheter (e.g., RELIEVA™ Guide Catheter, Acclarent, Inc., Menlo Park, Calif.) and into the paranasal sinus. Thereafter, a balloon catheter (e.g., RELIEVA™ Balloon Catheter, Acclarent, Inc., Menlo Park, Calif.) is advanced over the guidewire and is used to dilate the ostium of the paranasal sinus, thereby improving drainage from and/or ventilation of that paranasal sinus. Examples of such devices and procedures for balloon dilation of a paranasal sinus ostium are described in U.S. patent application Nos.: Ser. No. 10/829,917, now U.S. Pat. No. 7,654,997, issued Feb. 2, 2010, entitled "Devices, Systems and Methods for Diagnosing and Treating Sinusitis and Other Disorders of the Ears, Nose and/or Throat;" Ser. No. 10/944,270, published as U.S. Pub. No. 2006/0004323 on Jan. 5, 2006, entitled "Apparatus and Methods for Dilating and Modifying Ostia of Paranasal Sinuses and Other Intranasal or Paranasal Structures", now abandoned; Ser. No. 11/116,118, now U.S. Pat. No. 7,720, 521, issued May 18, 2010, entitled "Methods and Devices for Performing Procedures Within the Ear, Nose, Throat and Paranasal Sinuses;" Ser. No. 11/150,847, now U.S. Pat. No. 7,803,150, issued Sep. 28, 2010, entitled "Devices, Systems And Methods Useable For Treating Sinusitus" and Ser. No. 11/234,395, now U.S. Pat. No. 7,410,480, issued Aug. 12, 2008, entitled "Devices and Methods for Delivering Therapeutic Substances for the Treatment of Sinusitis and Other Disorders," the entire disclosure of each such patent application being expressly incorporated herein by reference.

Treatment of Frontal Sinusitis by Balloon Dilation of Frontal Outflow Tract and Implantation of Spacer Device with Sustained Corticosteroid Delivery FIGS. 8A through 8G show an example of one method by which the substance delivering spacer device 10 may be placed in the frontal sinus outflow tract FSO to perform a stenting and substance delivery function following balloon dilation of the frontal sinus outflow tract FSO.

In this procedure, the endoscope 400 is inserted and, optionally, a C-arm fluoroscope (not shown) may also be positioned to provide fluoroscopic images of the procedure when desired. Although, for clarity and visual simplicity, the endoscope 400 is shown only in FIGS. 8A and 8B, such endoscope 400 may remain in place throughout all or any part of this procedure and may be used for real time visualization of the movement and operation of the devices, as described in this example.

Under endoscopic visualization, a frontal sinus guide catheter 500 (e.g., the RELIEVA® Degree Sinus Guide Catheter; Acclarent, Inc., Menlo Park, Calif.) is inserted through the nostril and advanced to a position where its distal end is within or aligned with the frontal sinus ostium FSO. Such positioning of the guide catheter 500 may be verified by endoscopic visualization and/or fluoroscopy.

Figure 8A:
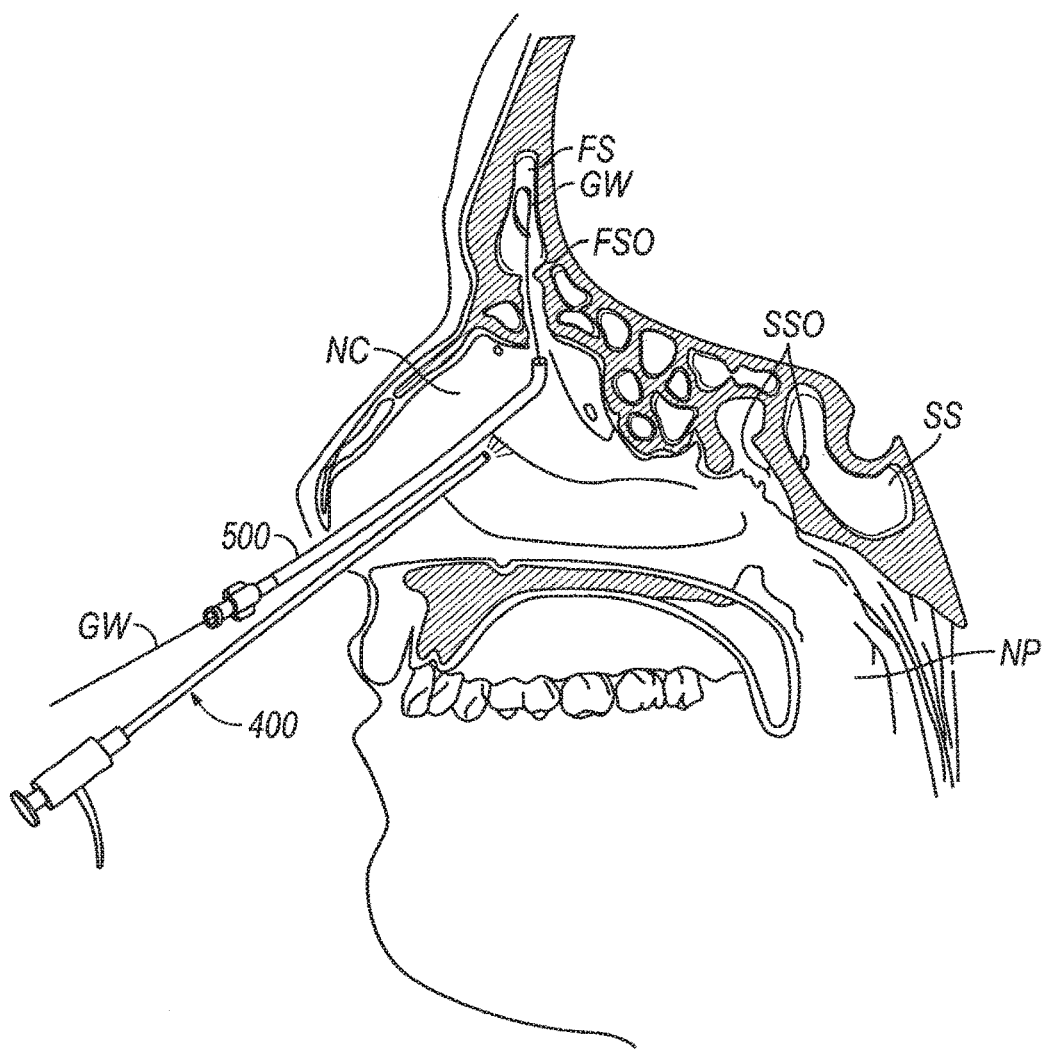
FIGS. 8A-8G show steps in a method for using a guide catheter for implantation of the substance delivering spacer device of FIG. 2 within the outflow tract of the frontal sinus of a human subject in accordance with the present invention.

Thereafter, a guidewire GW (RELIEVA® Sinus Guidewire; Acclarent, Inc., Menlo park, Calif.) is advanced through the guide catheter 500 and into the frontal sinus FS, as shown in FIG. 8A. The fluoroscope 404 may be used to verify that the guidewire GW has become coiled within the frontal sinus FS.

Figure 8B:
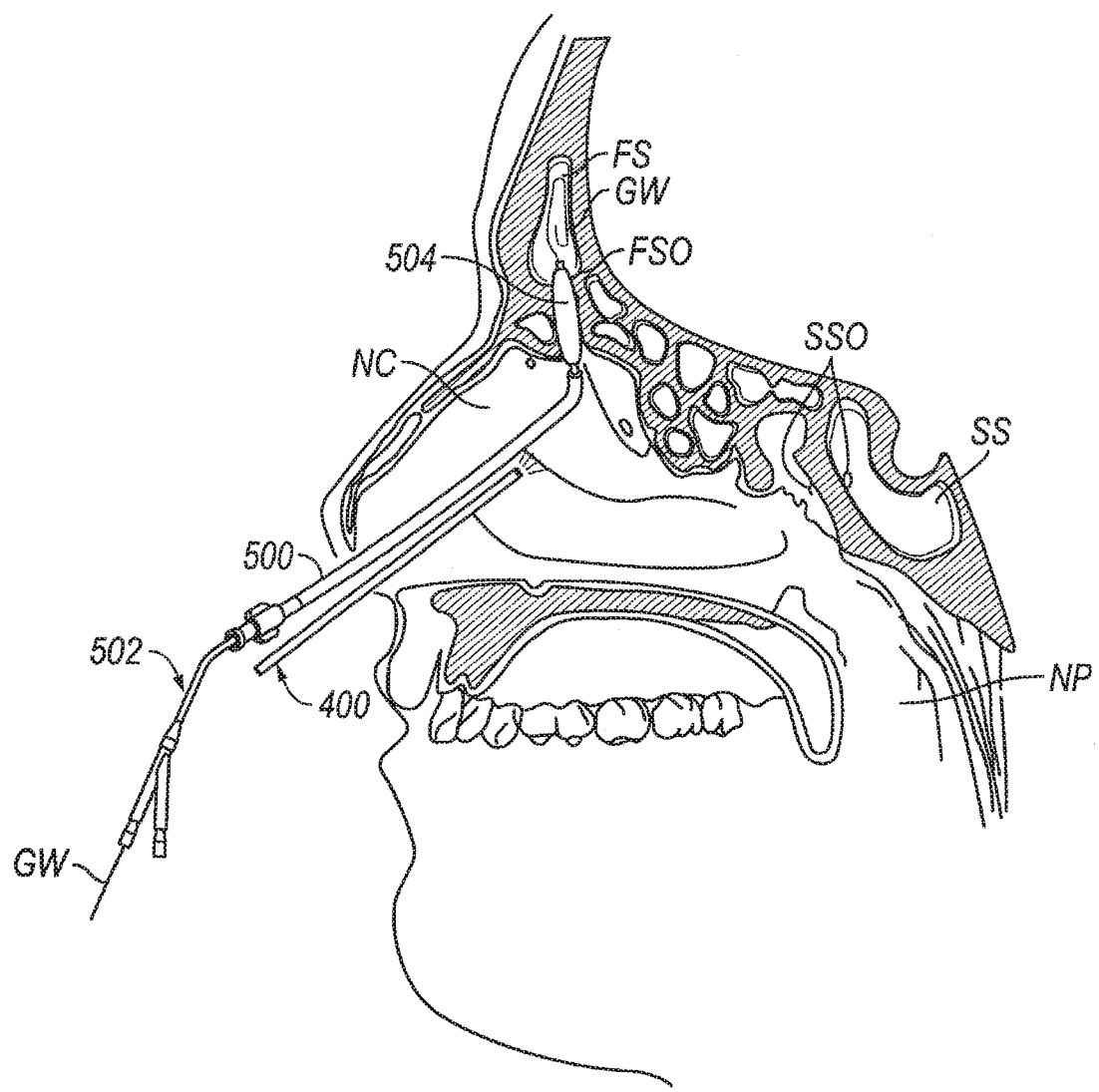

Thereafter, as shown in FIG. 8B, a dilation catheter 502 (e.g., the RELIEVA® or RELIEVA XL Sinus Balloon Catheter, Acclarent, Inc., Menlo Park, Calif.) is advanced over the guidewire GW and through the guide catheter 500 to a position where its dilator balloon 504 is positioned within the frontal sinus ostium FSO. The fluoroscope 400 may be used to verify that the guidewire GW has become coiled within the frontal sinus FS. With the dilator 504 so positioned, the dilator balloon 504 is expanded to cause dilation of the frontal sinus ostium FSO or other frontal sinus outflow tract. This procedure is described in detail in copending U.S. patent application Ser. No. 11/355,512, now U.S. Pat. No. 8,894,614, issued Nov. 25, 2014, the entire disclosure of which is expressly incorporated herein by reference. After the dilation has been completed, the dilator balloon 504 is again collapsed and the dilation catheter 502 is removed, leaving the guidewire 504 in place. Although this example includes this step of dilating the frontal sinus ostium FSO, this dilation step is optional. In some patients, the sinus ostium may have already been dilated or altered in a previous surgery or the physician may determine that dilation of the ostium is not needed prior to introduction of the spacer device 10.

Figure 8C:
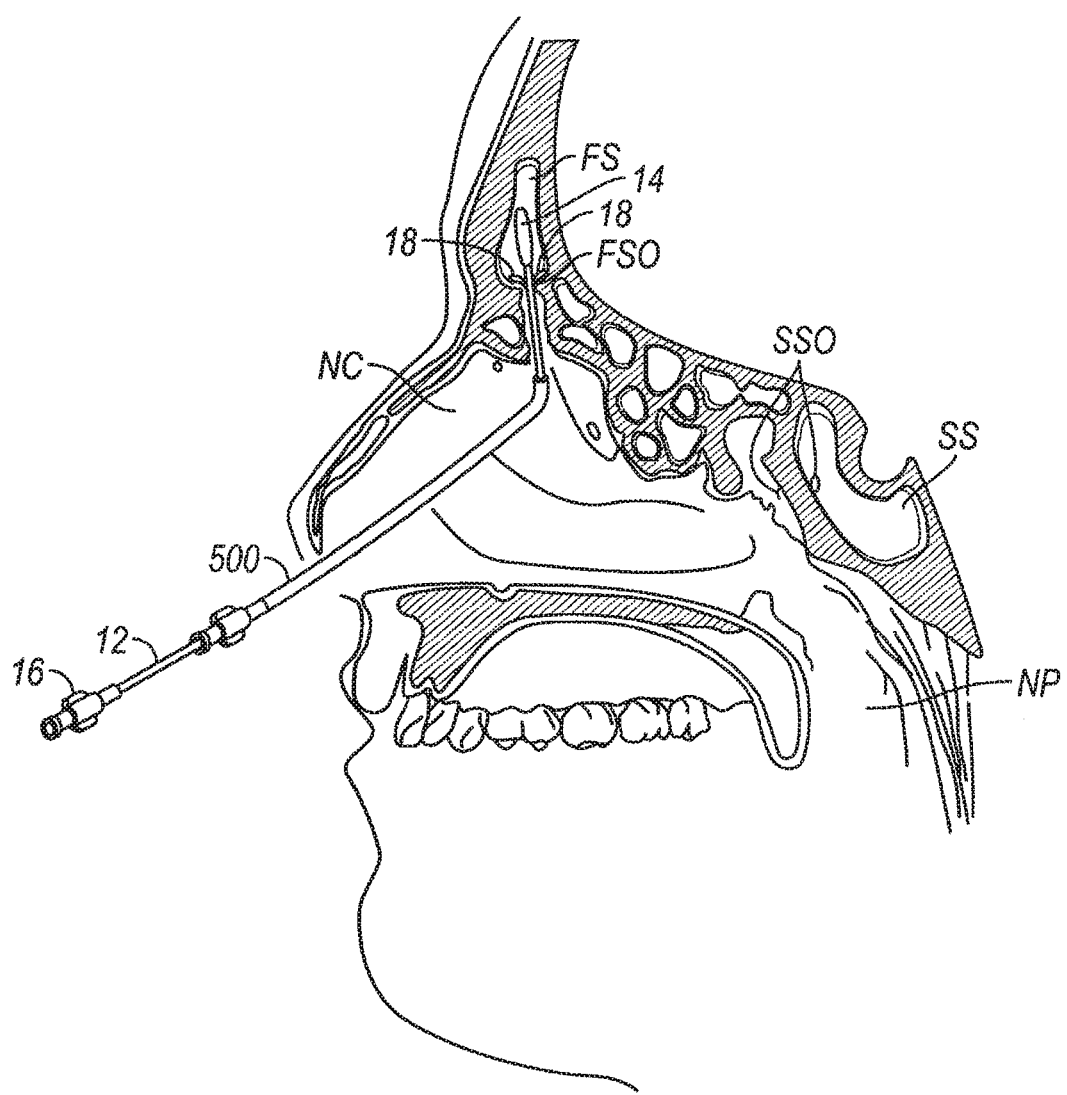

Thereafter, the substance delivering spacer device 10 is prepared and advanced through the guide catheter 500 and into the frontal sinus FS. Prior to insertion of the device 10 into the guide catheter 500, the constraining tube 42 may be removed and the retention wings 18 may be manually folded forward (i.e., in the distal direction) using finger pressure as the spacer device 10 is inserted into the proximal end of the guide catheter 500. As the distal end of the spacer device emerges out of the distal end of the guide catheter 500, the retention wings 18 will spring outwardly and will engage the frontal sinus ostium FSO as shown in FIG. 8C. Positioning of the reservoir 14 within the frontal sinus and successful deployment of the retention wings 18 may be verified fluoroscopically.

Figure 8D:
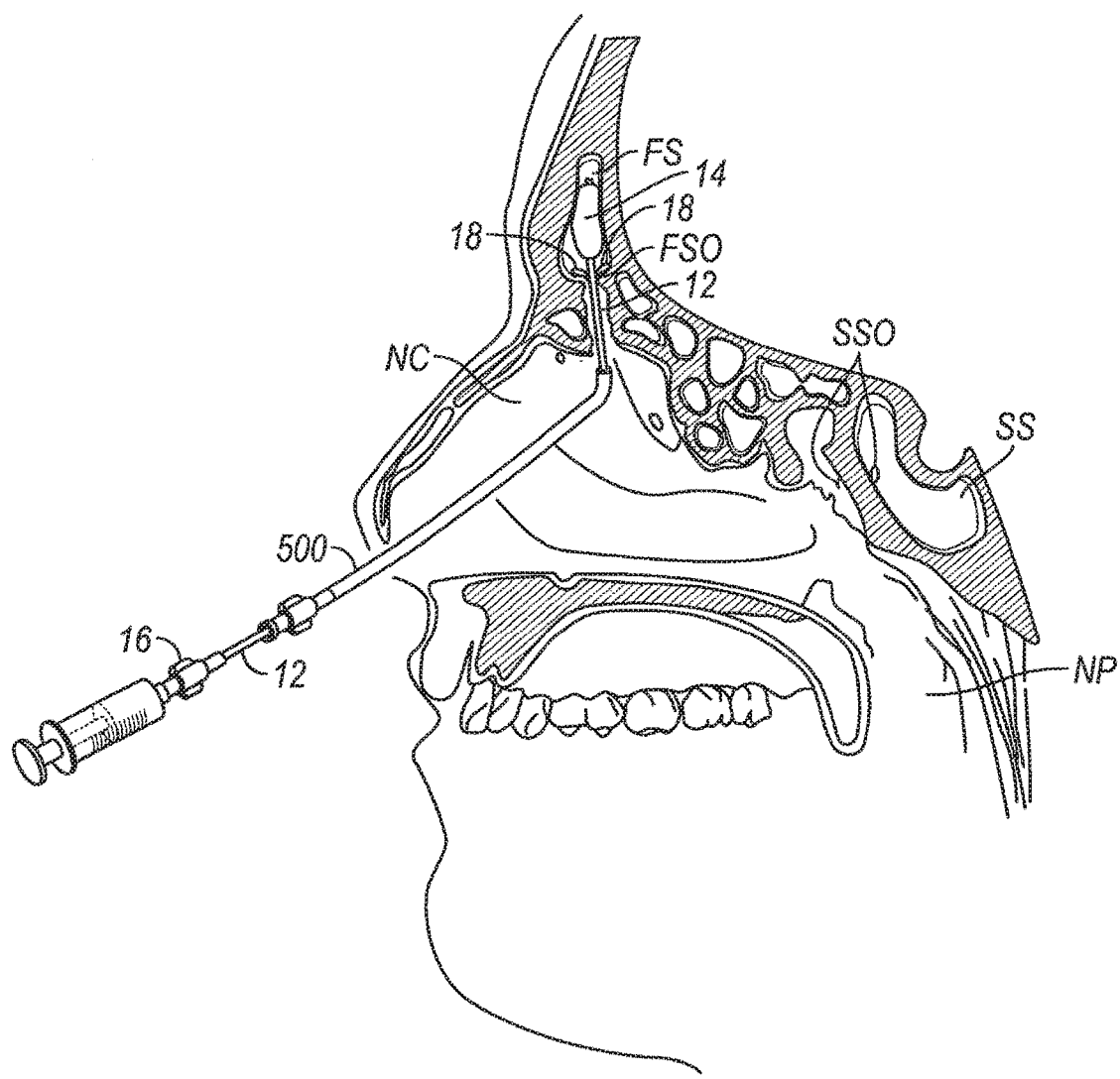

Thereafter, as shown in FIG. 8D, a syringe containing 0.31 cc to 0.35 cc of Triamcinolone Acetonide injectable suspension (KENALOG® 40, Brystol-Myers Squibb Company, Princeton, N.J.) is attached to the proximal Luer connector of the sinus spacer device 10 and the Triamcinolone Acetonide injectable suspension is injected, thereby causing the reservoir 14 to expand. Successful expansion of the reservoir 14a may be verified by CT.

Figure 8E:
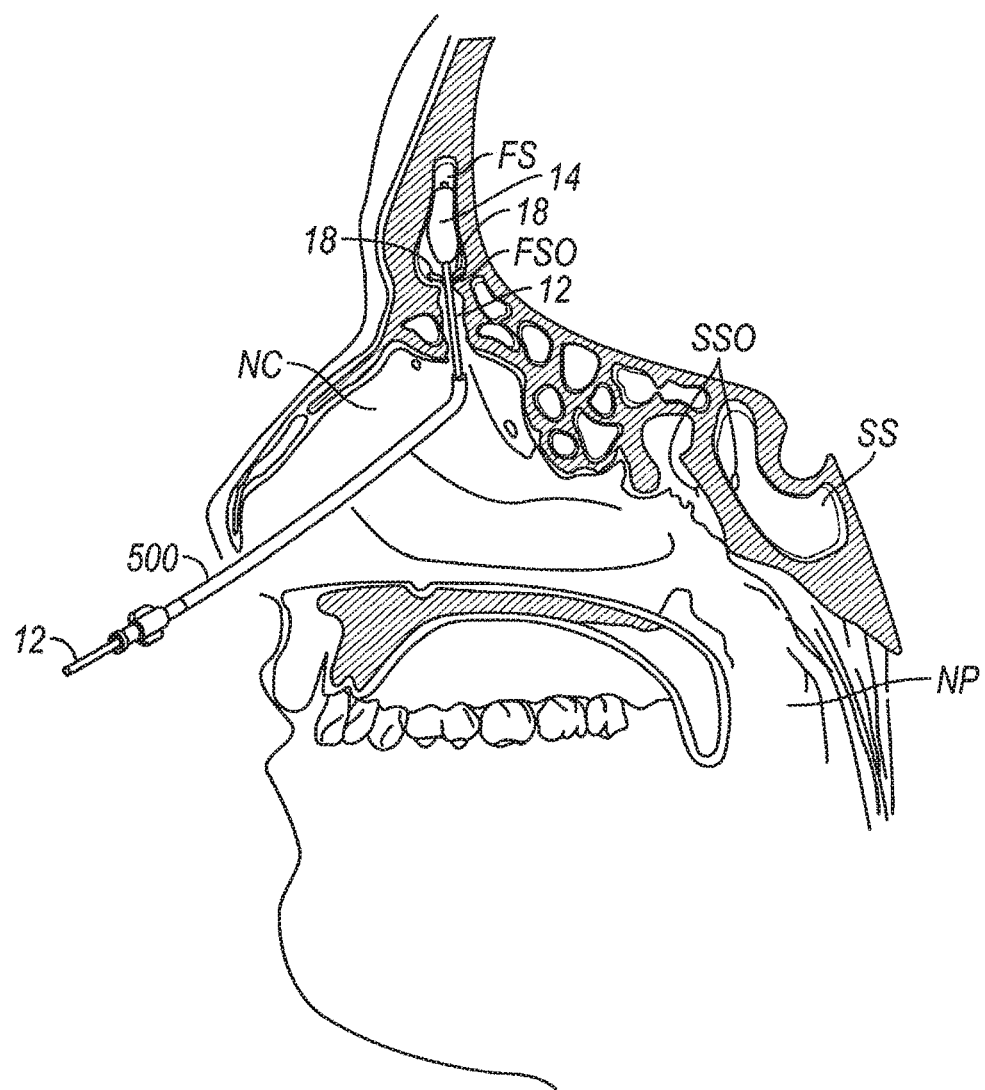
Figure 8F:
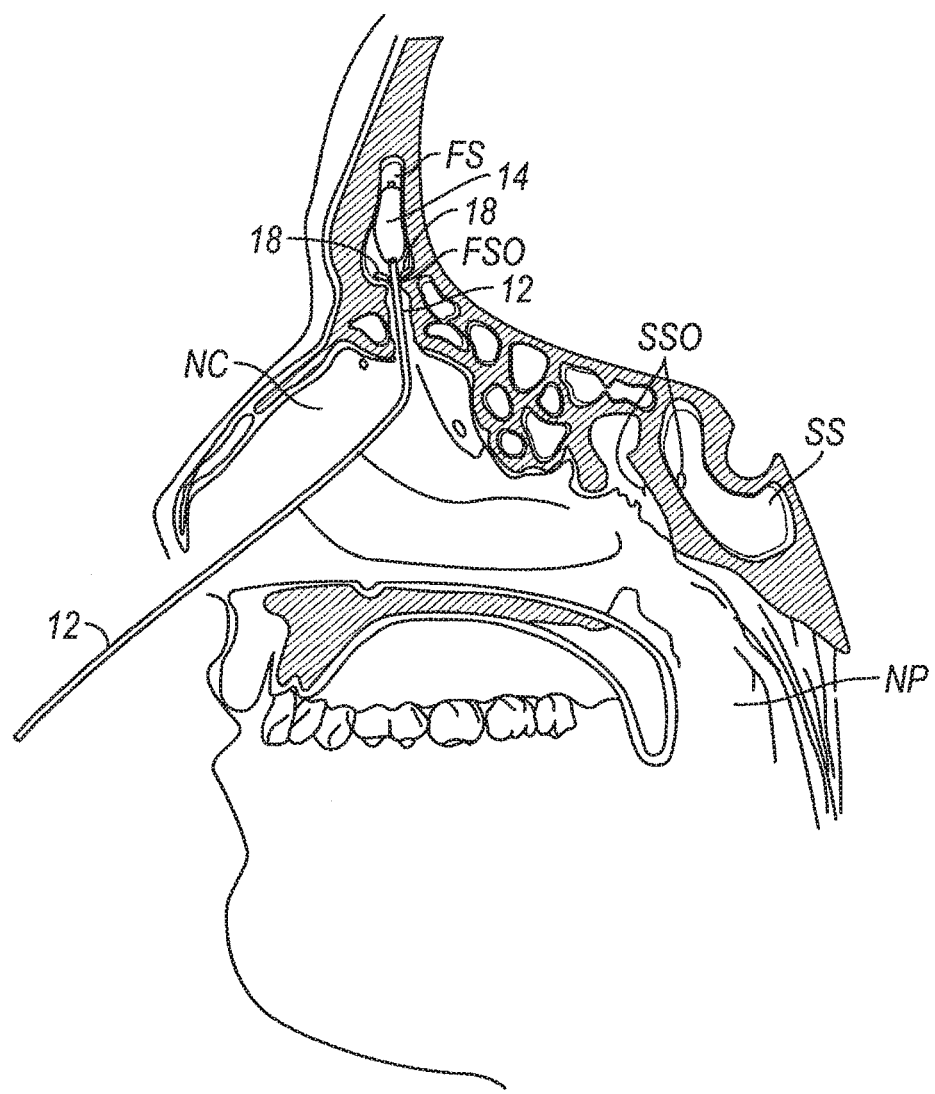
Figure 8G:
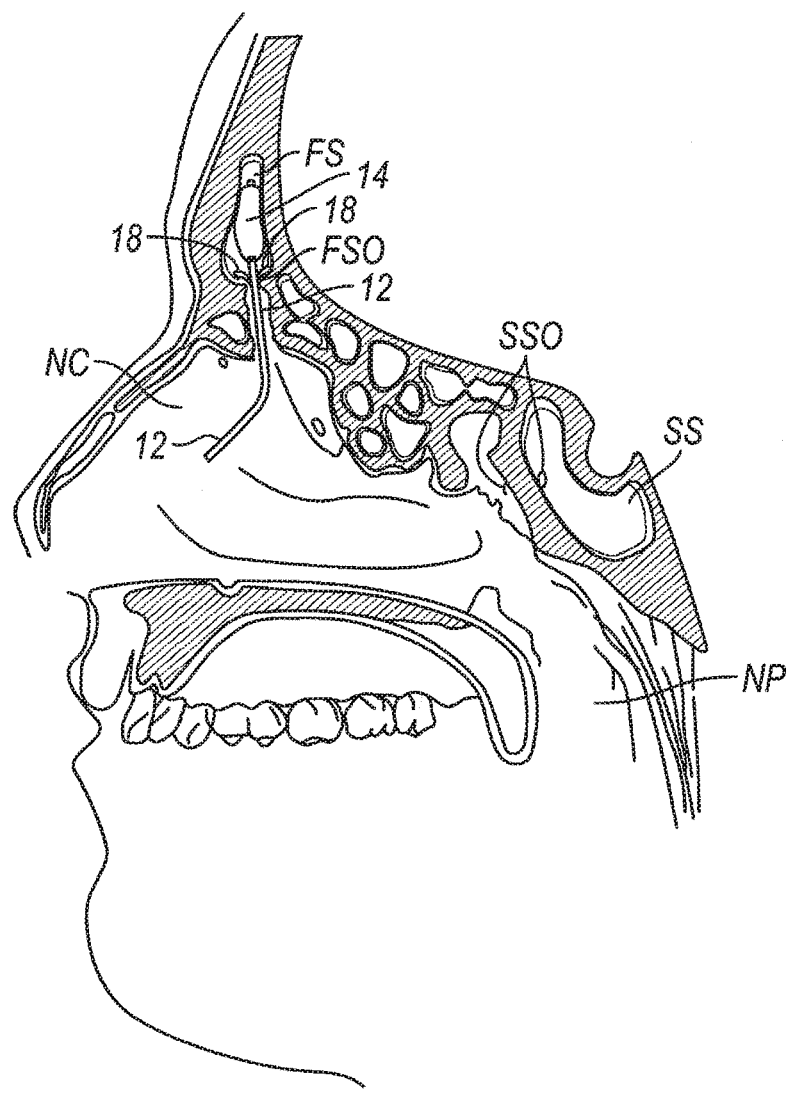

Thereafter, as shown in FIGS. 8E and 8F, the proximal end of the sinus spacer device 10 is cut off and the guide catheter is retracted proximally and removed. The operator may grasp the shaft 12 of the spacer device distal to the distal end of the guide catheter 500 as the guide catheter is removed to stabilize the spacer device 10 and to prevent it from being inadvertently dislodged from the frontal sinus FS during removal of the guide catheter 500.

Thereafter, a proximal portion of the shaft 12 of spacer device 10 may be cut away, leaving a short length of the shaft 12 hanging within the nose. The suture 17 with straight needle 19 is used to suture the suture tab 20 of the spacer device 10 to tissue within the nose, thereby helping to retain the implanted portion of the spacer device 10 in its desired position for a desired time period following the procedure. Some of the substance will remain in the remaining segment of shaft 12 distal to the cut and may leak into the nasal cavity subsequent to the procedure, thereby providing medication to other structures within the nasal cavity as well.

Treatment of Frontal Sinusitis by Implantation of Spacer Device with Sustained Corticosteroid Delivery In this example, FIGS. 9A-9D show steps in another method in which frontal sinusitis is treated in an adult human subject. The frontal sinus ostium FSO may or may not have been previously surgically altered or dilated as described above. Under endoscopic visualization, a frontal sinus guide catheter 500 (e.g., the RELIEVA® Degree Sinus Guide Catheter; Acclarent, Inc., Menlo Park, Calif.) is inserted through the nostril and advanced to a position where its distal end is within or aligned with the frontal sinus ostium FSO. Such positioning of the guide catheter 500 may be verified by endoscopic visualization and/or fluoroscopy.

Figure 9A:
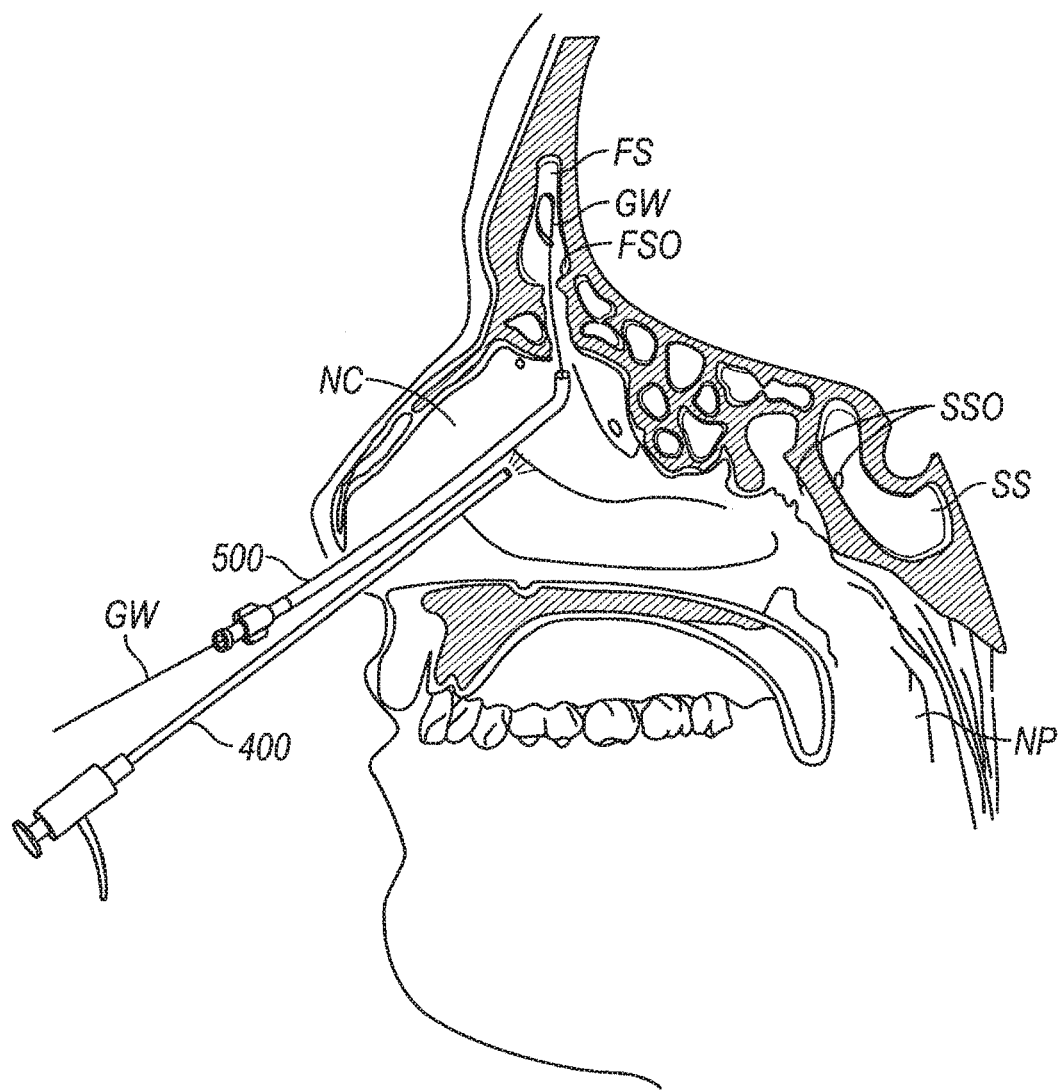
FIGS. 9A-9D show steps in a method for using the sheath of FIG. 4 and an optional dilator for implantation of the substance delivering spacer device of FIG. 2 within the outflow tract of the frontal sinus of a human subject in accordance with the present invention.

Thereafter, a guidewire GW (RELIEVA® Sinus Guidewire; Acclarent, Inc., Menlo park, Calif.) is advanced through the guide catheter 500 and into the frontal sinus FS, as shown in FIG. 9A. The fluoroscope 404 may be used to verify that the guidewire GW has become coiled within the frontal sinus FS.

Figure 9B:
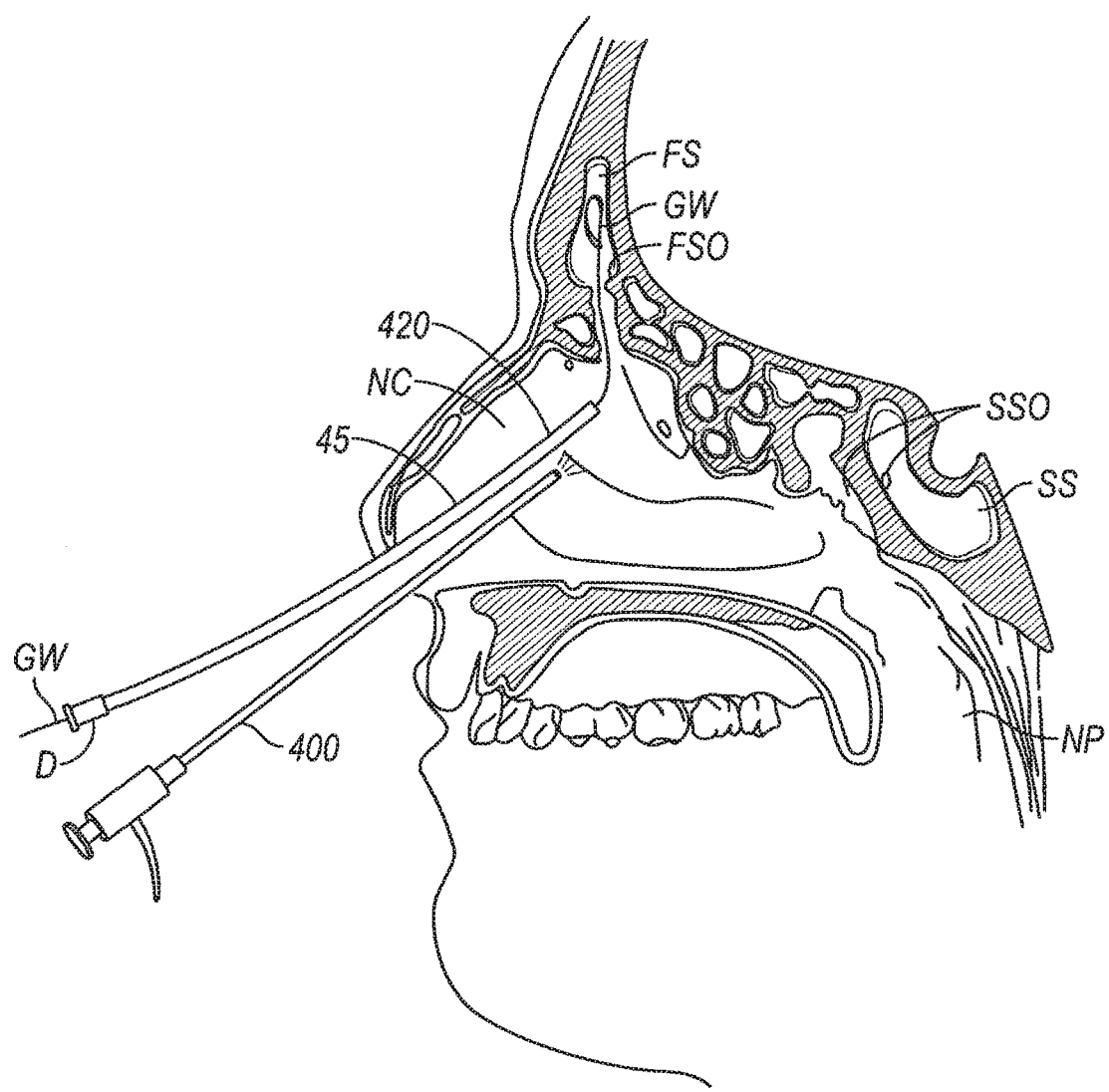
Figure 9C:
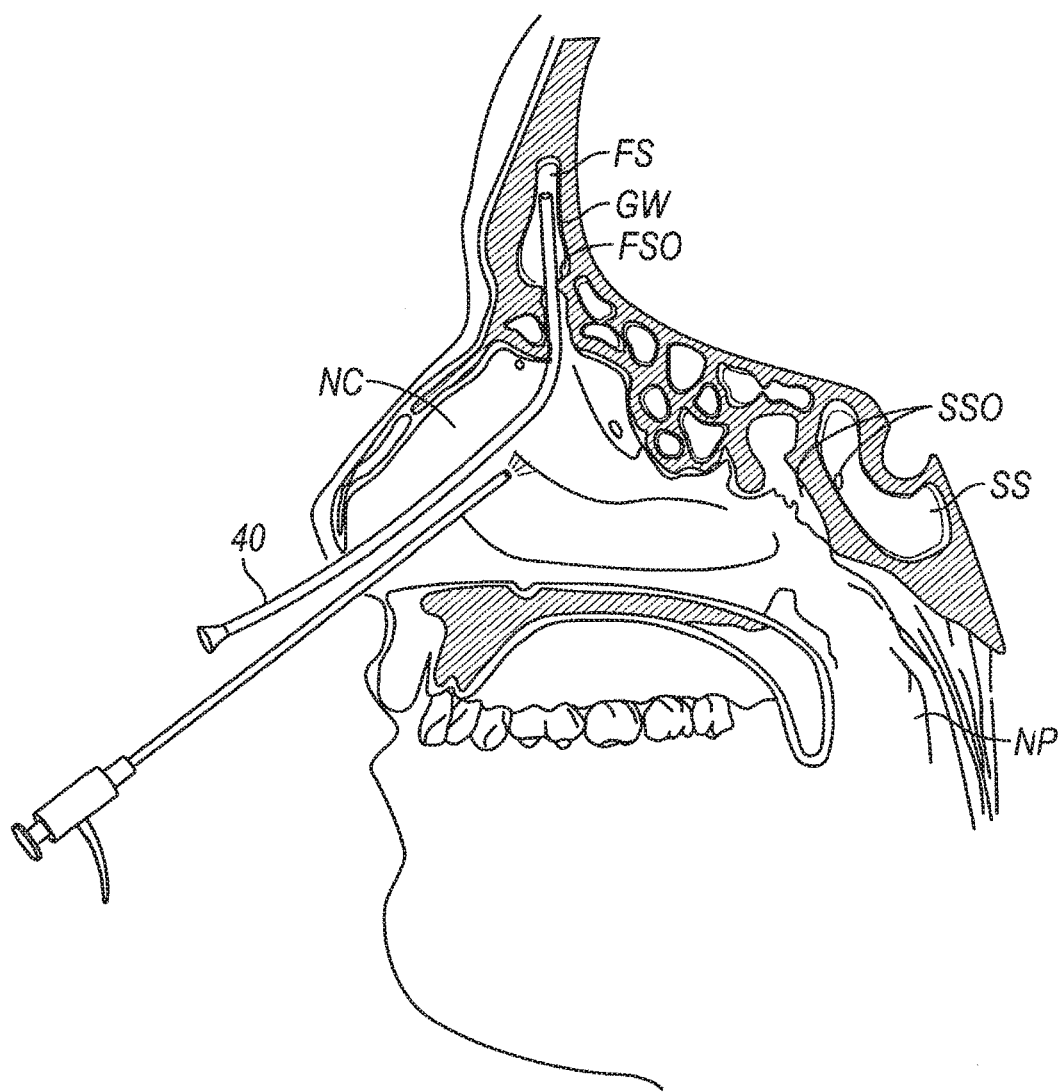

With reference to FIG. 9B, after the guidewire GW has been inserted into the frontal sinus, the frontal sinus guide catheter 500 is removed, leaving the guidewire GW in place. A 5 French vascular dilator 420 (e.g., 5 F vessel dilator (inner diameter of 0.038 in.), Merritt Medical Systems, Inc., South Jordan, Utah). The sheath/dilator combination is then advanced over the guidewire GW. The C-arm fluoroscope and/or the endoscope 400 may be used to observe the advancement of the sheath/dilator combination to a position where the proximal radiographic marker 52 of the sheath 40 is distal to the frontal recess (i.e., within the cavity of the frontal sinus). Once the sinus sheath 40 has been advanced to such location while within the lumen of the dilator, the 5F dilator 420 and the guidewire GW are removed leaving the sheath 40 in place, as shown in FIG. 9C.

Thereafter, the substance spacer device 10 is prepared as described above and the constraining tube 30 is placed in its advanced position so as to constrain and cover the suture loop 20, retention wings 18 and reservoir 14 in their collapsed positions. The device 10 is advanced into the previously inserted sheath 40 in substantially the same manner as described above and shown in FIGS. 8C-8E.

Thereafter, the sheath 40 and constraining tube 30 are retracted and a syringe containing 0.31 cc to 0.35 cc of Triamcinolone Acetonide injectable suspension (KENALOG® 40, Brystol-Myers Squibb Company, Princeton, N.J.) is attached to the proximal Luer connector of the sinus spacer device 10 and the Triamcinolone Acetonide injectable suspension is injected, thereby causing the reservoir 14 to expand within the frontal sinus FS, as previously described above. Successful expansion of the reservoir 14a may be verified by CT scan if desired.

Thereafter, the proximal end of the sinus spacer device 10 is cut off, and the sheath 40 and constraining tube 30 are retracted proximally and removed in the same manner as described above and shown in FIGS. 8H-8I.

Figure 9D:
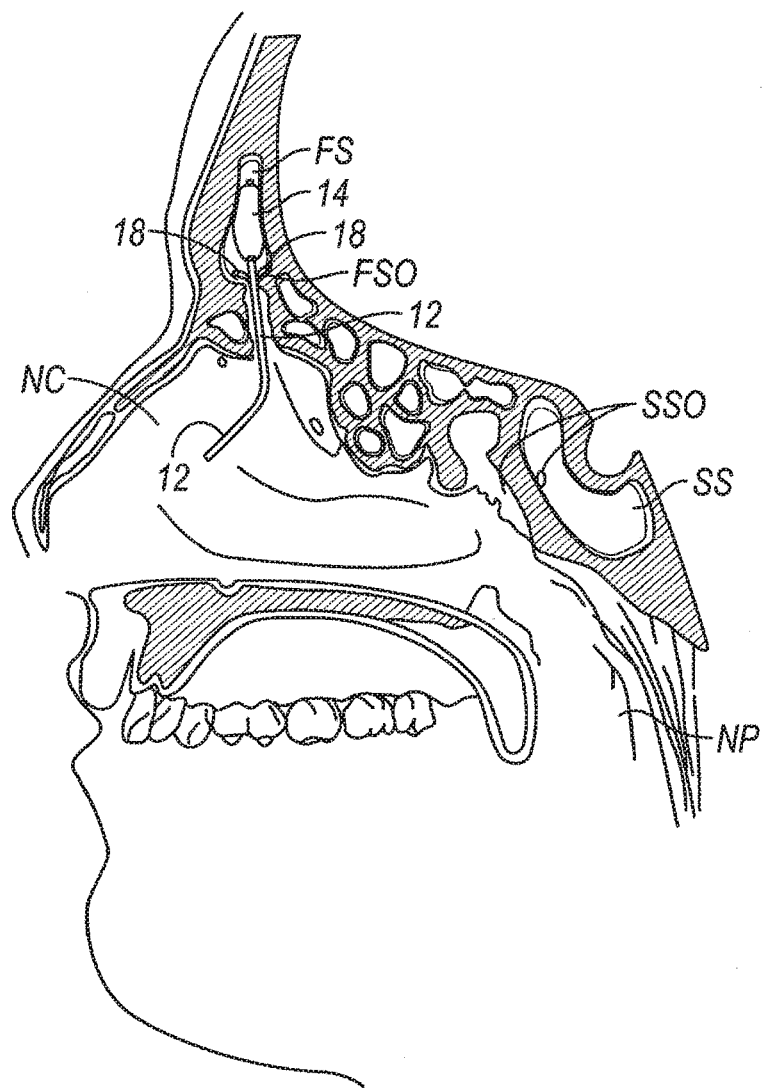

Thereafter, a proximal portion of the shaft 12 of spacer device 10 may be cut away, leaving a short length of the shaft 12 hanging within the nose. The suture 17 with straight needle 19 is used to suture the suture tab 20 of the spacer device 10 to tissue within the nose, thereby helping to retain the implanted portion of the spacer device 10 in its desired position for a desired time period following the procedure as seen in FIG. 9D. As described above, Triamcinolone Acetonide suspension that remains in the short segment of shaft 12 distal to the cut may subsequently leak into the nasal cavity NC, providing some additional therapeutic benefit to tissues in that area.

Alternative Approach to Frontal Sinusitis Treatment

Figure 10A:
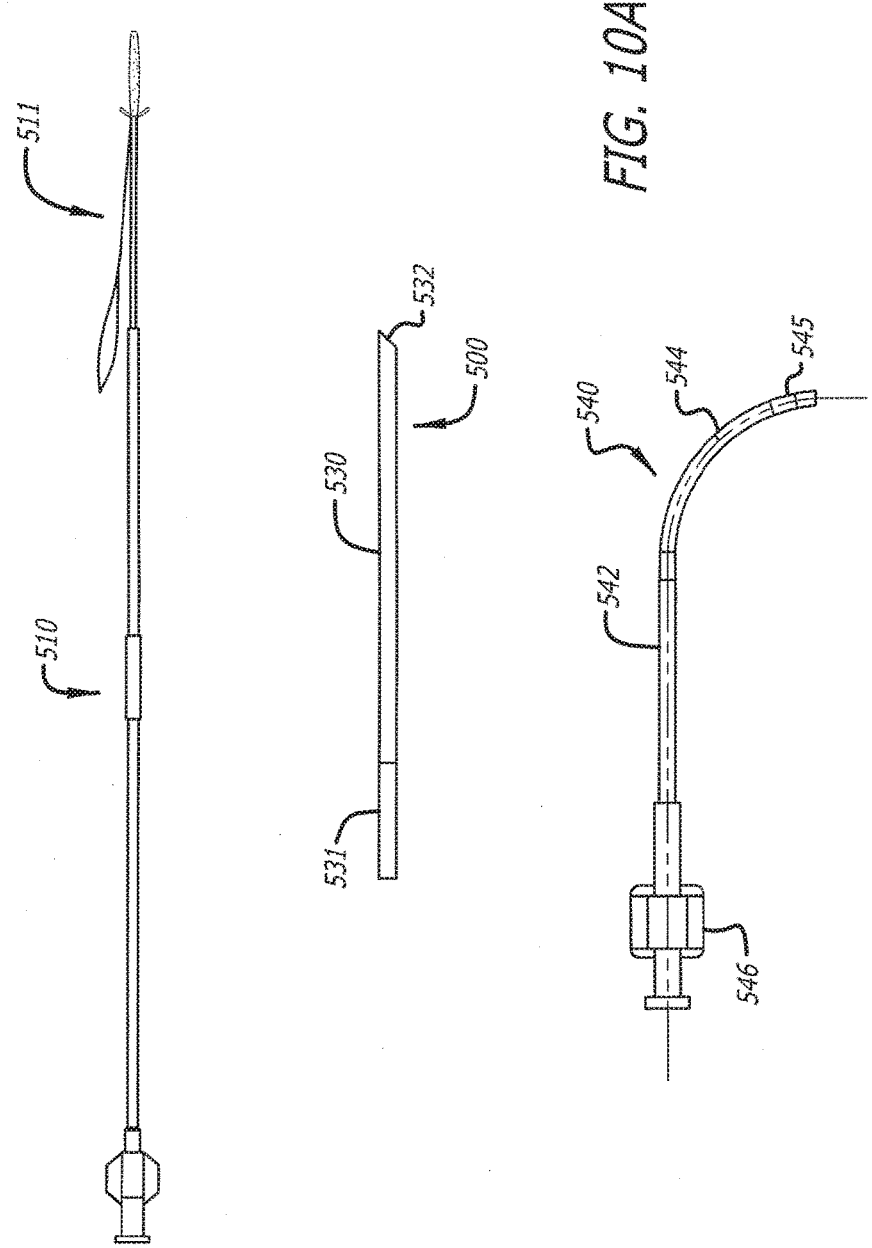
FIG. 10A shows a frontal paranasal sinus substance delivery system according to one embodiment of the present invention.
Figure 10B:
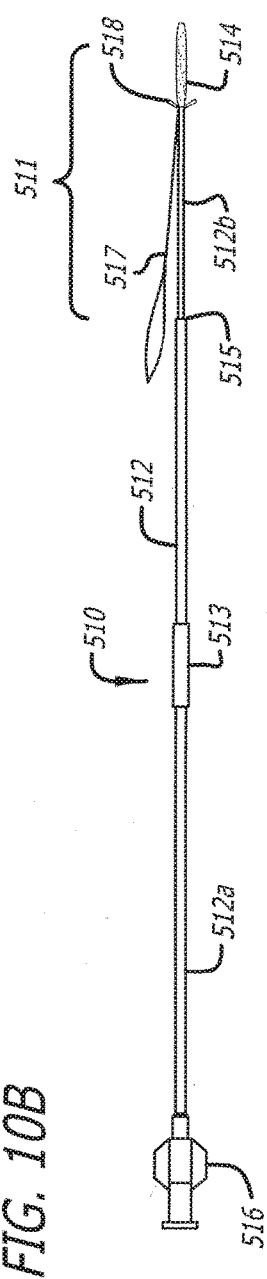
Figure 10C:
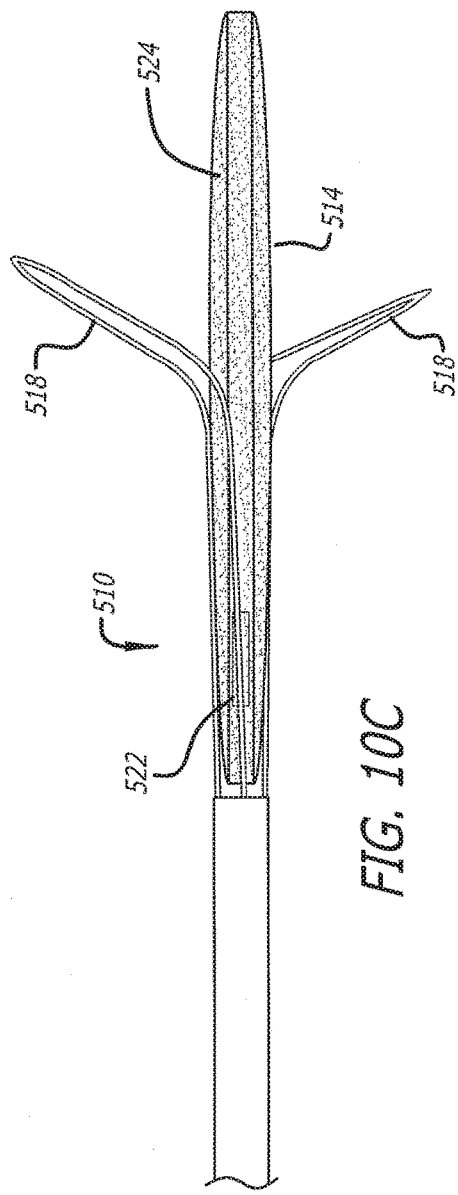

FIG. 10A shows an embodiment of a substance delivery system 500 configured for delivering substances to frontal paranasal sinuses. In one embodiment, the system 500 may include a substance delivery device 510 including a sinus spacer 511, a sheath 530 for covering the sinus spacer 530 before and during part of the delivery process, and a guide device 540 through which the spacer 511 is guided into a frontal paranasal sinus. Each of these devices will be described in greater detail below. In some embodiments, the system 500 may also include a syringe (not shown) or other substance/fluid injecting device for coupling with the proximal end of the substance delivery device 510 and injecting substance/fluid through the device 510 and into the spacer 511. Some embodiments may further include an amount of preloaded substance in the syringe, including but not limited to any of the substances listed herein. Optionally, some embodiments may also include a handle (not shown) for coupling with the guide device 540 to facilitate handling and advancement of the guide device 540 into a nostril of a patient. Any suitable handle may be used, in alternative embodiments, for example the RELIEVA SIDEKICK™ Sinus Guide Catheter Handle (Acclarent, Inc., Menlo Park, Calif.) may be used in one embodiment.

FIGS. 10B through 10E depict in further detail the substance delivery device 510 and implantable sinus spacer 511 shown in FIG. 10A. The device 510 includes an elongate flexible catheter shaft 512 having a proximal portion 512a and a distal portion 512b, where the distal portion 512b is considered part of the sinus spacer 511. As with previously described embodiments, the proximal and distal portions 512a, 512b may be severed from one another, such as by cutting, at or near a junction 515. In the embodiment shown, proximal shaft portion 512a is opaque and distal shaft portion 512b is relatively translucent or clear, so that during a procedure, junction 515 may be viewed with an endoscope. Further, the proximal shaft portion 512a and distal shaft portion 512b may be formed of the same or different materials and may have the same or different dimensions (e.g., diameter, wall thickness, etc.). For example, one such material is polyamide. In some embodiments, the distal shaft portion 512b may be made of a more flexible biocompatible material such as nylon or polyethylene teraphthalate (PET). A lumen extends continuously through the shaft 512. Moreover, the distal shaft portion 512a may be tapered or necked down to a smaller diameter than the proximal shaft portion to facilitate insertion of the device. A plug can be mounted in the distal end of the lumen. The plug may comprise any suitable closure member such as a wall of closed end on the tube, an end cap, a mass within the end of the lumen or any other suitable flow blocking member.

The sinus spacer 511 generally includes the distal shaft portion 512b, an expandable reservoir 514 mounted on the distal shaft portion 512b near its distal end, collapsible retention members 518 for retaining the spacer 511 in the sinus, and a suture loop 517 allowing a physician the option of attaching the spacer 511 to mucosal tissue to further ensure that the spacer 511 stays in a desired, implanted location. In general, the sinus spacer 511 may have any suitable dimensions, features, number of reservoir holes/apertures, sizes and shapes and numbers of retention members 518 and the like. Many of these features and details have been described above and thus will not be repeated here. Several differences between the frontal sinus spacer 511 and the spacers described above for ethmoid sinuses are as follows. The wing span of the retention members 518, measured from tip to tip in the expanded configuration, is approximately 13-16 mm for the frontal spacer device 511, versus approximately 9-12 mm for the ethmoid spacers. Each retention member 518 has an angle, in its expanded configuration and relative to the shaft 512, of about 70 degrees, versus about 80 degrees in the ethmoid spacers. Additionally, the overall length of the frontal sinus spacer 511 (i.e., the clear distal shaft portion 512b) is approximately 65 mm+/−3 mm, versus approximately 50 mm+/−3 mm in the ethmoid spacers. Of course, these features describe but one embodiment of the frontal sinus spacer 511, and various alternative embodiments may have different dimensions.

The reservoir 514 assumes an expanded configuration as it is filled. Here, the reservoir 514 may be formed of any suitable biocompatible material and, in some embodiments, may comprise a balloon formed of non-compliant or semi-compliant material such as Nylon 12. The reservoir can include a plurality of openings and can be configured as shown in FIGS. 2A and 2B. Moreover, as before, it is preferable that the material and wall thickness of the reservoir be such that the reservoir is flexible enough to a) allow the device to be extracted and removed from the body without causing significant trauma, b) not force all of the contents of the reservoir to come out at once and c) maintain substantially consistent size of openings 531 formed therein as the reservoir expands.

As described below, the reservoir 514 may be inserted in a collapsed configuration into a frontal sinus ostia or outflow tract and, thereafter, the reservoir may be loaded with the desired substance, causing the reservoir to transition to an expanded state.

In some embodiments, the reservoir 514 need not be used to deliver a therapeutic substance. It may, in fact, be used as a space occupying device. In such applications, the reservoir 514 may be loaded in situ with saline solution or other inert liquid, causing the reservoir 514 to expand and frictionally engage or contact adjacent anatomical structure(s), thereby providing a degree of retention at the desired implantation location. This aspect of the reservoir 514 may be further facilitated by the provision of surface projections on the reservoir.

The reservoir 514 may be relatively small in diameter when in its collapsed configuration, thus allowing it to be introduced or removed easily. In embodiments where the reservoir 514 is formed of non-compliant or semi-compliant material, the reservoir 514 will not undergo substantial elastic deformation in the filling process and thus will not exert pressure on its contents in order to expel the desired substance through openings 531. Rather, the substance in the reservoir 514 will elute through the openings 531 by gravity and/or by the passage of mucus through the sinus via ciliary action. This non-pressurized delivery allows for the slow release of the desired substance over several days. In some other embodiments, the reservoir 514 may be formed of compliant or elastic material with small openings 531 such that the material of which the balloon 514 is formed will contract as substance passes out of the openings 531, thereby maintaining pressure within the balloon. Also, in this example, the reservoir has a cylindrical side wall 514*a* which defines the working length of the reservoir, a distal taper 514*b* which transitions from the cylindrical side wall 514*a* to the distal shaft 512*b* (distal to the reservoir) and a proximal taper 514*c* that transitions from the cylindrical side wall 514*a* to the distal shaft 512*b* (proximal to the reservoir), and the openings 531 extend onto the proximal and distal tapers 514*b*, 514*c*, as shown. The reservoir 514 may have dimensions, openings, and overall configuration as described previously with reference to other embodiments.

The distal shaft portion 512*b* may be made of Nylon 12 in one embodiment. As mentioned above, in one embodiment the full length of sinus spacer 511, from the distal tip to the proximal end of the distal shaft portion 512*b*, may be about 65 mm+/.+−.3 mm. An aperture is formed in the catheter shaft 512 to facilitate filling of the reservoir 514. A valve can also be provided to allow the substance (or component(s) of the substance) to flow from the lumen of the catheter shaft 12 into the reservoir 514 and prevent substantial backflow from the reservoir 514 into the lumen 513. The valve may comprise any suitable type of one way valve.

Also, a distal radiopaque marker 524 and proximal radiopaque marker 522 may be provided to facilitate the desired positioning of the reservoir 514 within a subject's body. Each of these markers 522, 524 may be made of a ring of radiopaque material and may be mounted on the shaft 512 in alignment with each end of the reservoir's cylindrical sidewall 514*a*. For example, each marker 522, 524 can embody a band of Platinum-Iridium alloy. These markers are visible under various imaging techniques including fluoroscopy and CT scanning.

The proximal shaft portion 512*a* may be made of polyimide tubing in one embodiment. A hub 516 comprising a female Luer connector made of clear polycarbonate can be attached to the proximal end of shaft 512. Proximal shaft portion 512*a* and distal shaft portion 512*b* may, in general, have any of the dimensions, features, materials and the like of similar catheter shafts described in reference to other embodiments above. In one embodiment, the proximal shaft portion 512*a* may include a shaft marker 513. The shaft marker 513 may be positioned along the shaft 512 such that when a distal end of the shaft marker 513 reaches a proximal end of the stop member 531 on the sheath 530 during advancement (described in greater detail below), then the distal end of the sinus spacer 511 is adjacent the distal end of the guide device 540. When the proximal end of the shaft marker 513 reaches the proximal end of the stop member 531, then the sinus spacer 511 has been advanced out of the distal end of the guide 540. Use of the shaft marker during a sinus spacer placement procedure is described more fully below in reference to FIGS. 13A-13H.

Additionally, the implantable substance delivery device or spacer 510 can include a pair of retention wings 518. It is to be recognized that the spacer 510 can alternatively include three or four or more such wings. The retention wings 518 are located at diametrically opposed locations on the shaft 512, and extend distally about the reservoir 514. Each retention wing 518 can embody a preformed loop of nickel-titanium (nitinol) wire. Each retention wing 518 may be flexed or compressed to a collapsed position where it lies substantially flat against the outer surface of the reservoir 514. However, the retention wings 518 are biased to a preformed configuration such that, when unconstrained, each retention wing 518 will resiliently spring outwardly to an extended position wherein it extends at an angle of from about 20 degrees to about 90 degrees relative to the longitudinal axis of the shaft 512, and more ideally from about 50 degrees to about 80 degrees, and in one embodiment about 70 degrees. In various embodiments, the wings 518 may define a wing span of about 9 mm to about 20 mm or more, and more ideally from about 13 mm to about 16 mm, and in one embodiment about 15 mm. In one embodiment, the distal end of the spacer device 511 may be provided with an atraumatic tip formed from a soft polymer. Further, in some embodiments, the geometry and positioning of the wings 518 may be selected so that drug housed in the reservoir 514 can elute out of openings 531 both proximal and distal to the wings 518. In an alternative embodiment, wings 518 may be positioned along the shaft 512 such that all of the openings 531 are disposed distal to the wings 518.

As seen in FIGS. 10D and 10E, a tubular constraining sheath may be positioned over the shaft 512 of the implantable substance delivery device 510. In one embodiment, for example, this constraining sheath 530 may be configured as a length of plastic tubing having a length of about 75 mm+/−2 mm (although other lengths may be used in alternative embodiments). The constraining sheath 530 is moveable back and forth between a retracted position (seen in FIG. 10D) and an extended position (seen in FIG. 10E). When in the extended position, the constraining sheath extends over the retention wings 518, and the collapsed reservoir 514, thereby holding the retention wings 518 in their collapsed positions and forming a smooth protective covering. When in the extended position, the constraining sheath 530 will add column strength to the overall device 510 and will minimize kinking of the shaft 512 as it is pushed through relatively narrow and/or tortuous anatomical passages. After the device 510 has been inserted to the desired position, the constraining sheath 512 may be withdrawn to its retracted position, thereby allowing the retention wings 518 to spring outwardly to their extended positions and the reservoir 514 to undergo expansion when it is subsequently loaded with the desired substance.

In one embodiment, the sheath 530 includes a proximal stop member 541. The stop member 541 is configured to abut a proximal luer on the guide device 540 as the sheath 530 and the substance delivery device 510 are advanced into the guide 540. Thus, as the sheath 530 and substance delivery device 510 are advanced, the stop member 541 stops advancement of the sheath 530, and the substance delivery device 510 continues to be advanced, so that the sinus spacer exits out of the distal end of the guide 540. In other words, the sheath 530 with stop member 541 allows the wings 518 of the sinus spacer 511 to be constrained before and during advancement into the patient, until the spacer 511 is advanced out of the distal end of the guide 540.

The sheath 530 may also include a slanted or bevelled distal tip 532. This slanted distal tip 532 shape may facilitate pulling the sinus spacer 511 back into the sheath 530 if that is necessary during a procedure. The tip 532 may also facilitate advancement of the sheath 530 through the guide 540.

Figure 11A:
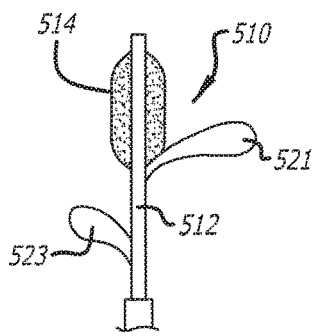
FIGS. 11A-11D depict various alternative embodiments of frontal sinus spacer devices.
Figure 11B:
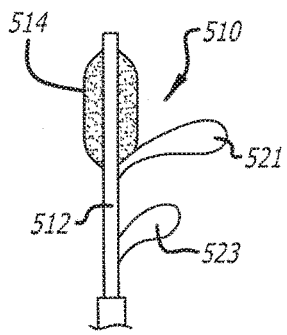
Figure 11C:
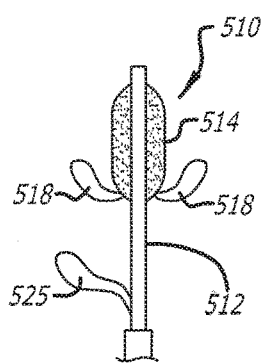
Figure 11D:
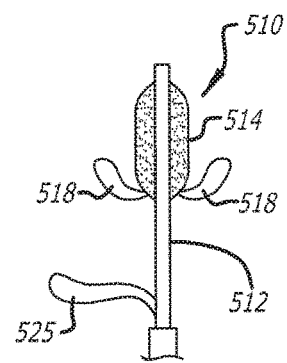

Further alternative embodiments of an implantable substance delivery device are shown in FIGS. 11A-11D. In one approach, as shown in FIG. 11A, the implantable device 510 can include a pair of retention wings 521, 523 forming loops and being located at staggered locations along the device. For example, one wing 521 can be attached to a first side of the device adjacent the junction between the reservoir 514 and the shaft 512 and a second wing 523 can be attached to the shaft 512 proximal to the first wing 518. With this wing placement, the bottom wing 523 may push against a wall of a frontal recess (the passageway leading to and just proximal to the frontal sinus), thereby helping maintain a desired position of the top wing 521 within the frontal sinus. In another approach (See FIG. 11B), the wings 521, 523 can be similarly staggered but configured to project from a common side of the implantable substance delivery device 510. In yet another approach (See FIGS. 11C and 11D), in addition to embodying diametrically opposed wings 518 extendable along a periphery of the reservoir 514, the implantable device 510 can include a bottom wing 525 having various configurations, such as that forming an overall L-shape (FIG. 11D) or an S-shape (FIG. 11C). Further, the bottom wing 525 can have a strength and geometry suited for resting on a frontal recess and for pushing the shaft 512 of the device laterally. The multiple offset wings also facilitate enhanced anchoring of the substance delivery device 510 in the frontal recess/frontal sinus anatomy.

Turning now to FIGS. 12A-D, various embodiments of a sheath or guide 540 are shown. Guides 540 are configured for advancing an implantable device such as those described above into a frontal recess and/or frontal paranasal sinus, as shown, for example, in FIGS. 13A-13E. Generally, the guide 540 may include a proximal straight portion 542, a distal curved portion 544 having a radiopaque distal tip 545, and a proximal luer connector 546. In one embodiment the guide 540 may be made of a polymer shaped as tube and curved to form the distal portion 544, with a straight hypotube disposed over the proximal portion 542. In one embodiment, the curved distal portion 544 may be relatively flexible, so that it has sufficient pushability to be advanced through the nasal cavity but sufficient flexibility to prevent damage to the nasal cavity walls and structures. The overall length, curvature angle and configuration of the guide 540 may be designed so that the proximal luer connector 546 remains outside a patient's nose while the guide 540 extends through a nostril and nasal cavity such that the distal end 545 is positioned in or near a frontal paranasal sinus ostium.

Figure 12A:
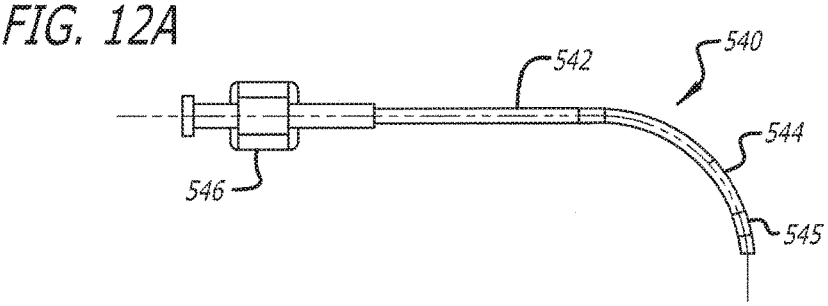
FIG. 12A shows a guide device for guiding a substance delivery device into a frontal paranasal sinus according to one embodiment of the present invention.
Figure 12B:
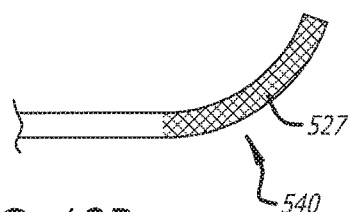
FIGS. 12B-12E depict various views and embodiments of a distal end of a guide devices similar to the device of FIG. 12A.
Figure 12C:
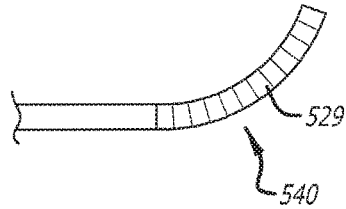
Figure 12D:
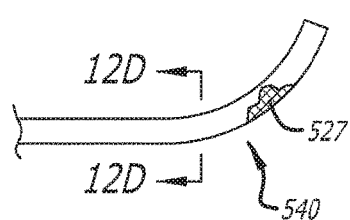
Figure 12E:

In some embodiments, the sheath or guide 540 may have a shapeable (bendable, malleable, etc.) distal portion or tip that can be adjusted to fit a patient's anatomy. The tip may be preshaped with a given curve but may be adjusted by the user as necessary. The material of such a tip may be a bendable or malleable tubing that may retain its shape and may also be repeatedly shaped as needed. For example, in one embodiment, the material may be a type of plastic with braided wires 527 (See FIG. 12B) or a spring 529 (See FIG. 12C). Moreover, such structure can be encapsulated by the plastic (See FIGS. 12D-E) or the structure can surround the plastic (FIGS. 12B-C). The material may also be made of a malleable metal. Accordingly, if the preshaped tip of the sheath or guide does not work, the tip may be shaped in order to navigate through the frontal recess and into the frontal sinus.

With reference now to FIGS. 13A-H, another method for treating a frontal sinus is depicted. For clarity, this method embodiment is shown without use of a handle coupled with the guide 540, however, in alternative embodiments a handle (as described above) may be coupled with the guide 540 before the initial advancement step.

In some embodiments, the substance delivery device 510 may be prepared as described above, and the constraining sheath 530 may be placed in its advanced position to constrain and cover the retention wings 518 and reservoir 514 in their collapsed positions. In alternative embodiments, the sheath 530 and substance delivery device 510 may be provided in a configuration ready to be used.

As shown in FIG. 13A, under endoscopic visualization, a frontal sinus guide catheter 540 is inserted through the nostril and advanced to a position where its distal end is proximal to, within or aligned with the frontal sinus ostium FSO. Such positioning of the guide 540 may be verified by visualization with an endoscope 400 and/or via fluoroscopy (for example, visualizing the radiopaque distal tip of the guide relative to the frontal sinus ostium). As mentioned previously, because the frontal sinus has a relatively long outflow tract (the frontal recess), it may be desirable to position the spacer device 510 at least partially within the outflow tract, and the guide or sheath 540 may be positioned to accomplish this.

Figure 13B:
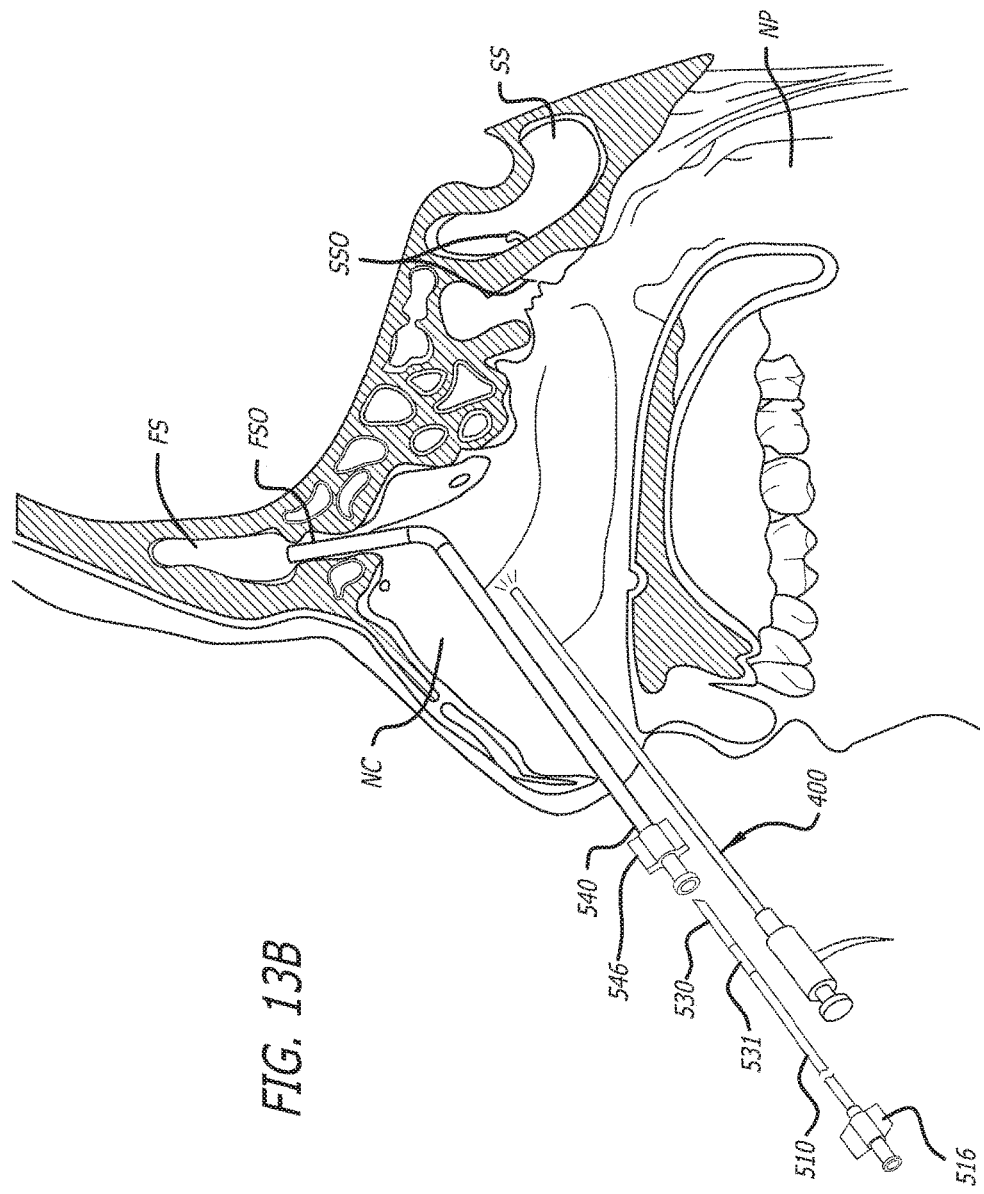
Figure 13C:
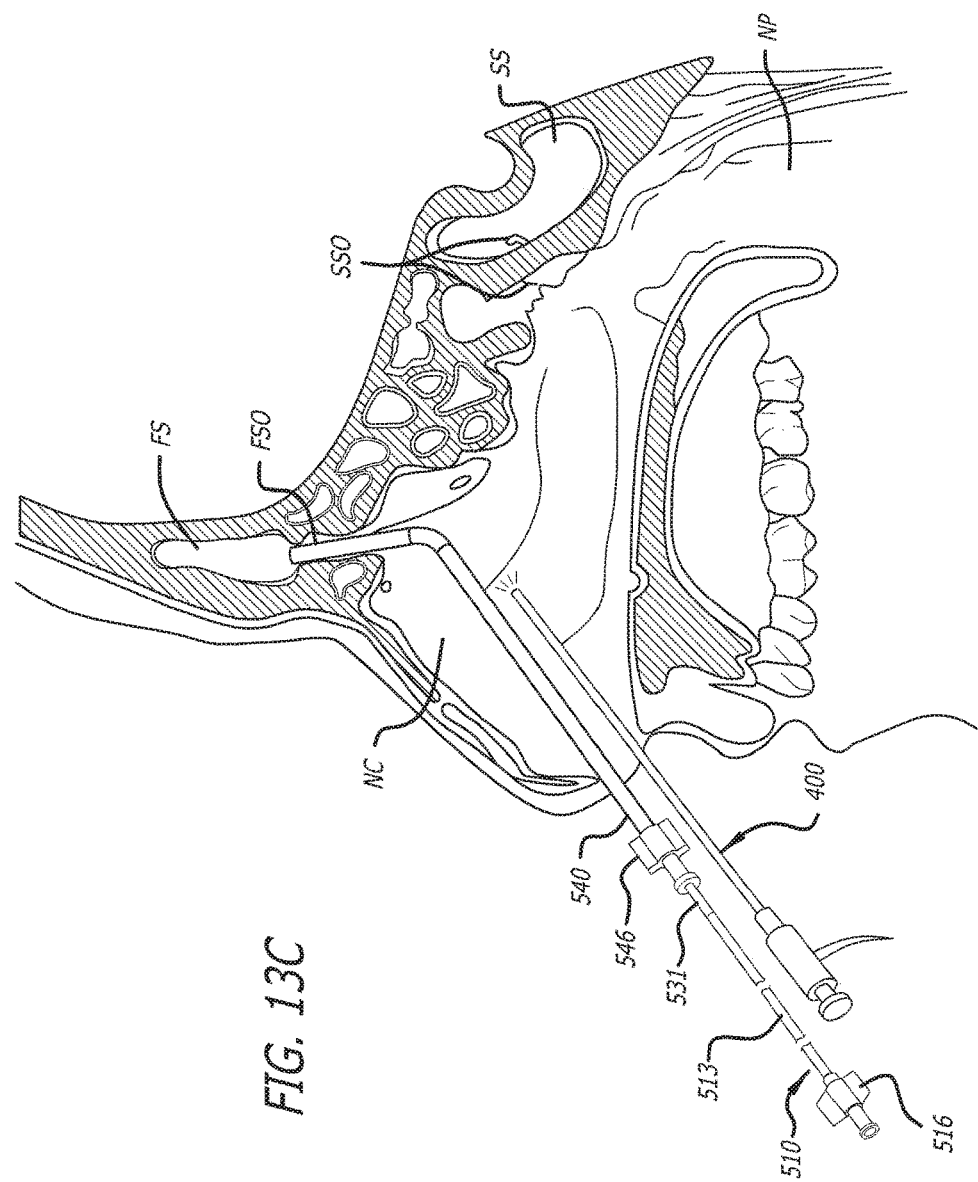
Figure 13D:
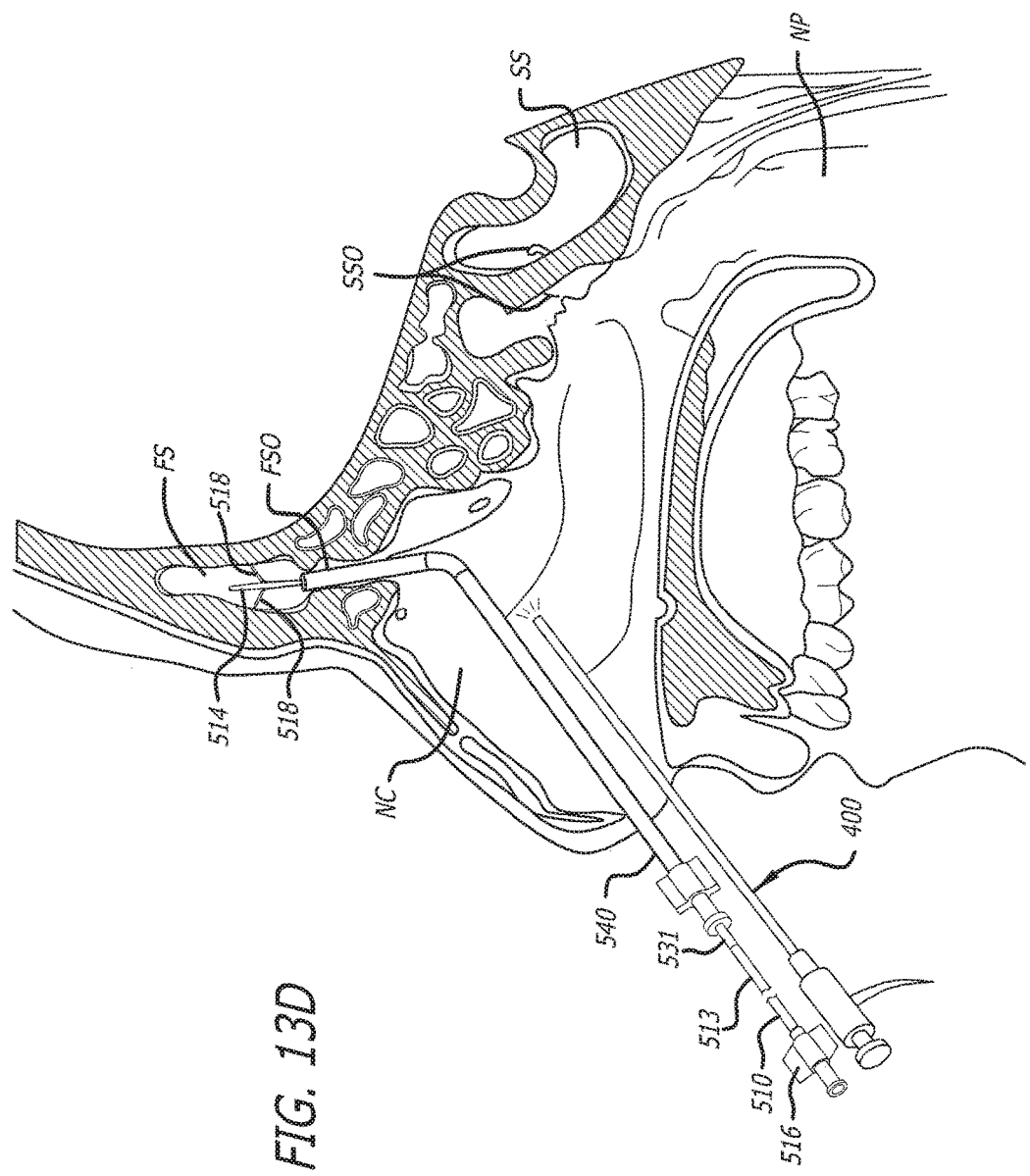

As shown in FIG. 13B, as a next step, the substance delivery device 510, with the constraining sheath 530 disposed over the sinus spacer 511, may be advanced into and through the guide catheter 540. Next, as shown in FIG. 13C, the substance delivery device 510 and sheath 530 are further advanced through the guide 540 until the stop member 541 on the sheath abuts the luer connector 546 on the guide 540. The substance delivery device 510 is further advanced through the guide 540 and the stopped sheath 530, until the distal end of the shaft marker 513 reaches the proximal end of the stop member 541, thus indicating that the distal end of the sinus spacer 511 is adjacent the distal end of the guide device 540. As shown in FIG. 13D, as the substance delivery device 510 is further advanced through the guide 540 and the stopped sheath 530, when the proximal end of the shaft marker 513 reaches the proximal end of the stop member 541, then the sinus spacer 511 has been advanced out of the distal end of the guide 540, thus deploying the retention wings 518 within the frontal sinus.

Figure 13E:
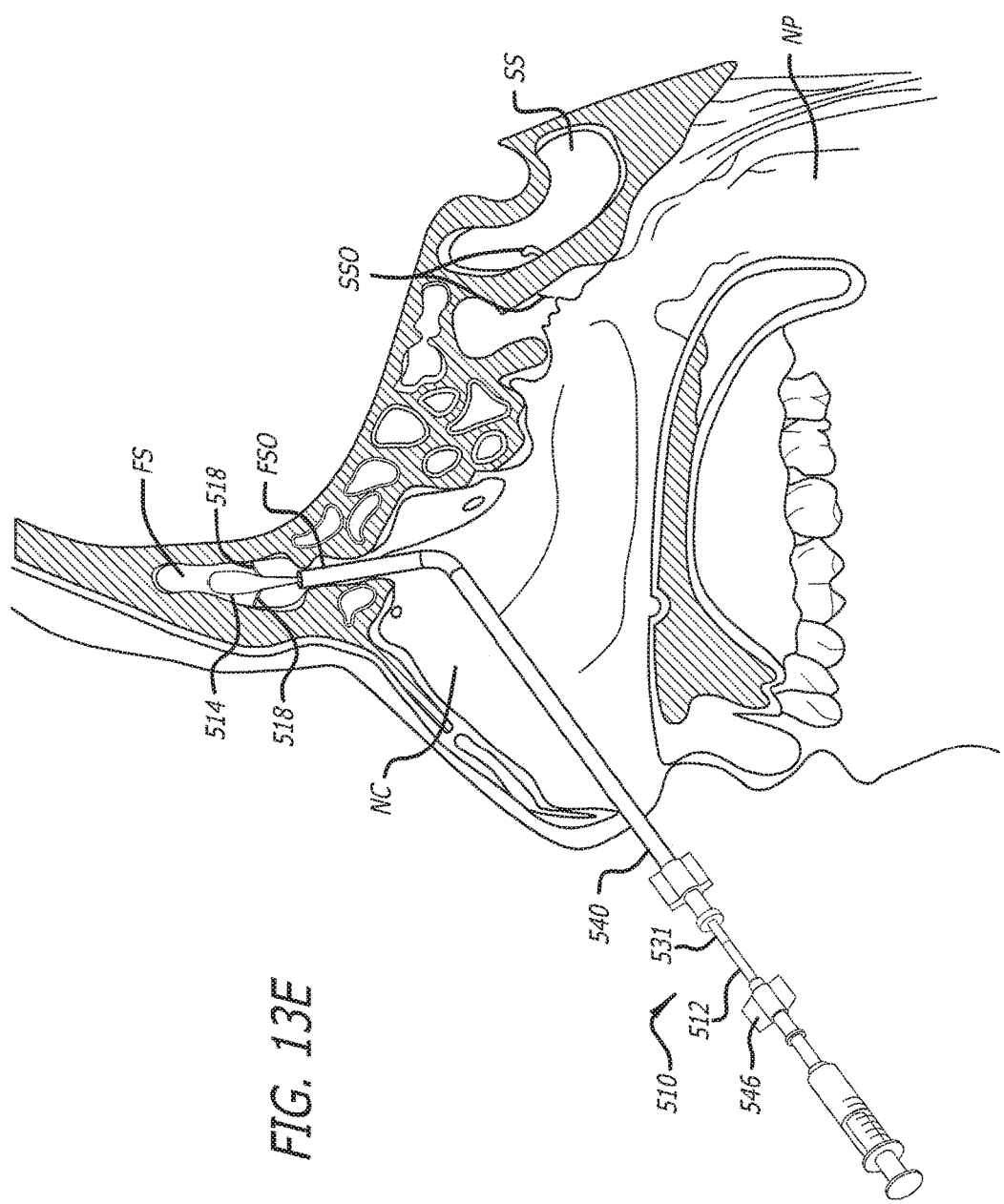

Thereafter, as shown in FIG. 13E, a substance is injected through the catheter shaft 512 into the expandable reservoir 514 of the sinus spacer 511 to expand the reservoir 514 and to allow the substance to elute out of holes in the reservoir 514. In one embodiment, a syringe containing a substance, for example a corticosteroid suspension such as but not limited to triamcinolone acetonide, an antibiotic, an antifungal, a nonsteroidal anti-inflammatory and/or the like, is attached to the proximal luer connector 516 of the substance delivery device 510. The injectable composition is then injected, thereby causing the reservoir 514 to expand. In some embodiments, the injected substance and/or the reservoir 514 may be radiopaque, so that successful expansion of the reservoir 514*a* may be verified by fluoroscopy or other suitable radiographic technique.

Figure 13H:
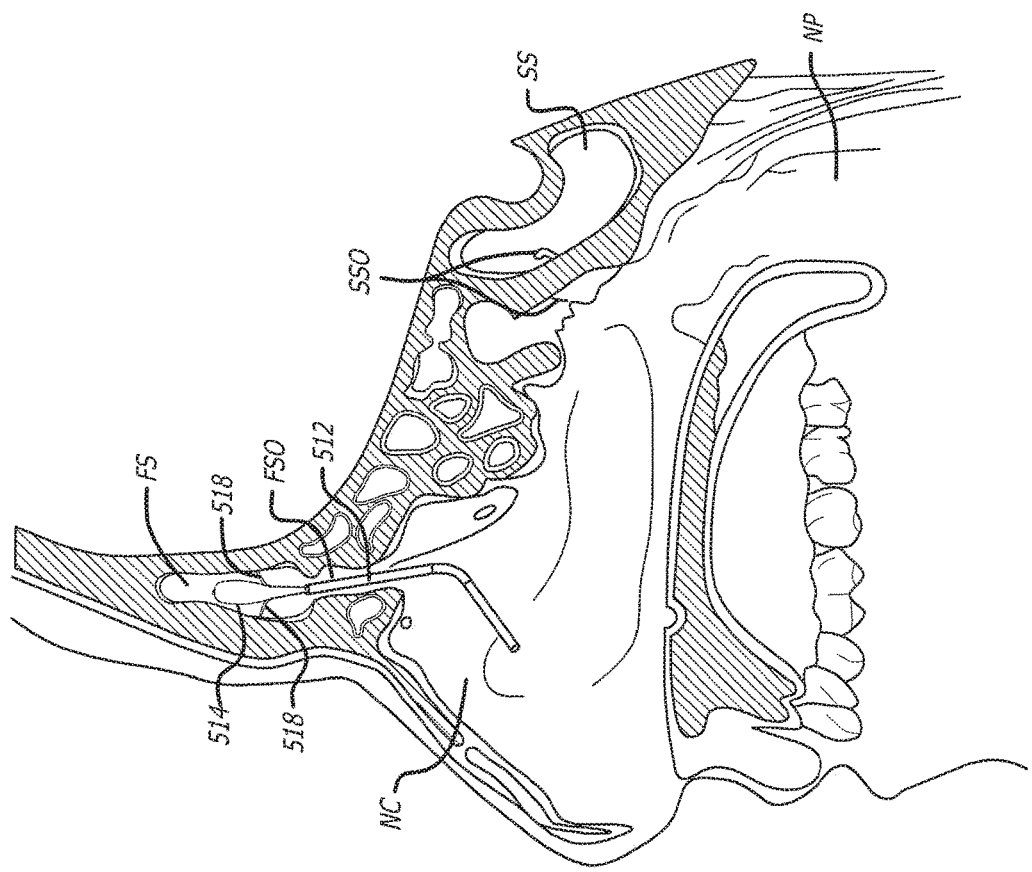

Next, as shown in FIG. 13F, the luer connector 516 on the proximal end of the substance delivery device 510 is cut off or otherwise removed. As in FIG. 13G, the guide 540 may then be slid proximally over the substance delivery device 510 to remove the guide 540 from the nostril. As shown in FIG. 13H, the sinus spacer device 511 is then separated from the proximal catheter shaft portion 512a, such as by inserting scissors into the nostril and cutting at or near the junction of the proximal portion 512a and the distal portion 512b. The proximal shaft portion 512a may then be removed from the patient, leaving the sinus spacer 511 in place within the frontal sinus and extending into the frontal outflow tract/ frontal recess. In some embodiments, the physician may wish to further secure the sinus spacer 511 by attaching the eyelet of the suture loop 517 to the mucosal within the nasal cavity. However, this is not a required step, and the retention wings 518 will typically secure the sinus spacer 511 within the frontal sinus.

The sinus spacer 511 may contain any suitable substance or combination of substances, such as but not limited to any of the substances listed in the present application. The sinus spacer 511 may be left in the frontal sinus for any length of time, such as from one day to one year, and more ideally from about 7 days to about 90 days, and even more ideally from about 14 days to about one month. In some embodiments, substance may only be delivered to a frontal paranasal sinus using the frontal sinus spacer 511. Alternatively, substance may be delivered to the frontal sinus and the frontal recess or outflow tract and in some cases even farther proximally within the nasal cavity. Oftentimes, the delivered substance will be chosen to have a beneficial effect not only within a sinus but in any other location in the nasal cavity to which it might be delivered.

As with the embodiments described above, the method just described may be performed after the frontal sinus ostium and/or frontal outflow tract is expanded using a BALLOON SINUPLASTY™ sinus dilation procedure. Alternatively, the method may be performed on a "native," non-operated frontal paranasal sinus. Whether a prior BALLOON SINUPLASTY™ sinus dilation procedure is performed may sometimes depend on how wide the frontal sinus ostium and/or the frontal outflow tract are.

Figure 14A:
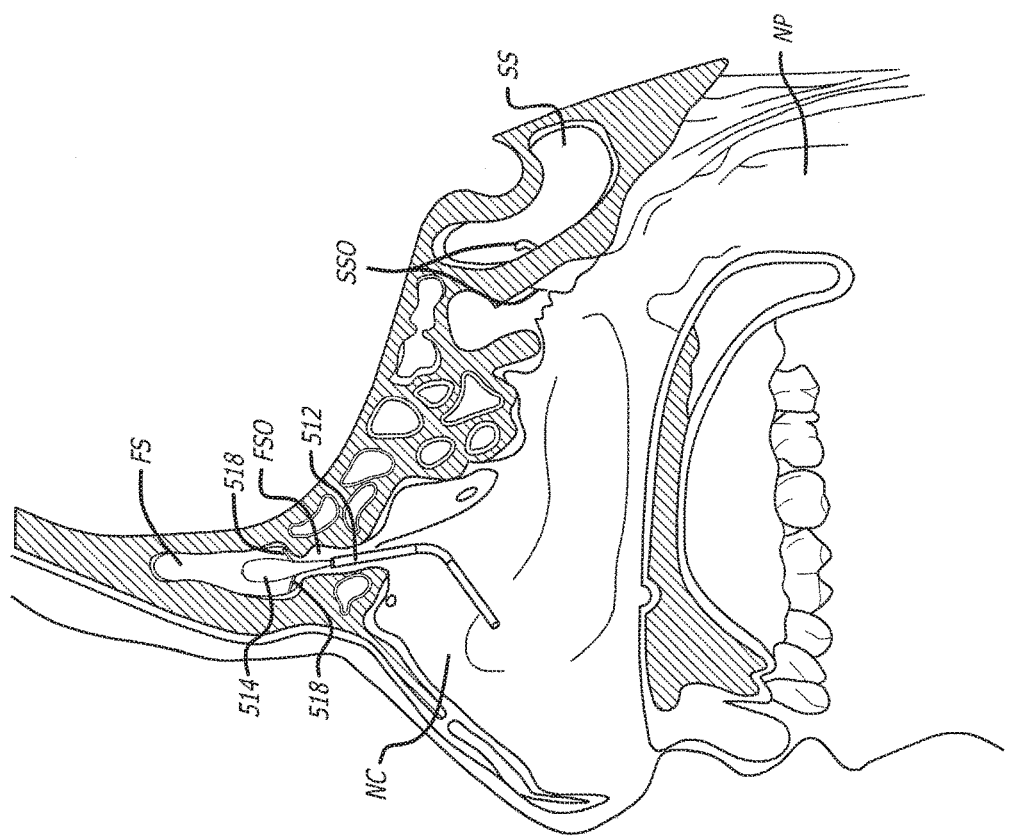

Referring now to FIGS. 14A-D, alternative embodiments of the spacer device 510 are shown implanted in the frontal sinus. In one alternate approach, the membrane or reservoir 514 of a spacer 510 has a relatively longer profile such that a portion of its length extends proximally within the frontal sinus recess. Additionally, embodiments of a spacer device 510 can include differently positioned, staggered retention wings 521, 523 are shown in FIGS. 14B and 14C, where the proximally located wing 523 is placed in apposition with a frontal sinus recess such that desired orientation of spacer device 510 is achieved. Also, a spacer device 510 including a bottom wing 525 can be implanted such that the bottom wing 525 aids in both securing and orienting the spacer at the interventional site (See FIG. 14D).

Although the accompanying drawings and above-described examples have specifically shown techniques for implanting the substance delivering spacer device 510 in the frontal sinus, similar techniques may be employed to implant the device in other sinuses. Of course, various other approaches and delivery equipment may be required to accomplish the same.

Stability of Triamcinolone Acetonide within Spacer Device Following Implantation A study was performed to confirm that the Triamcinolone Acetonide injectable suspension (KENALOG® 40, Brystol-Myers Squibb Company, Princeton, N.J.), when loaded into the reservoir 14 of the substance delivering spacer device 10, remains intact and capable of pharmacologic activity for at least 30 days following implantation of the device. In this study, the reservoir 14 of one device 10 was loaded by injecting 0.31 cc of the Triamcinolone Acetonide injectable suspension as described above (hereinafter referred to as "Triamcinolone Acetonide loaded reservoir"). The reservoir 14 of a second device 10 was loaded with saline (hereinafter referred to as "placebo loaded reservoir") and the reservoir of a third device remained empty (hereinafter referred to as "blank reservoir") All three devices were maintained under ICH stability conditions (40°±2° C./75% RH±5% RH) in Caron Model 6030 Environmental Stability Chamber. High Performance Liquid Chromatography (HPLC) was performed on aliquots of the contents of each reservoir at day 0 and day 30. The results of this study are summarized in Table 1 below:

| Attributes | Results at Each Time Point, % | |
|---|---|---|
| | 0-Day | 30-Day |
| Assay: | 93.5% | 85.4% |
| Individual Impurity: | | |
| RRT = 0.31 | 0.05 | 0.05 |
| RRT = 0.47 | 0.10 | 0.11 |
| RRT = 0.77 | 0.03 | 0.03 |
| RRT = 0.87 | 0.03 | 0.03 |
| RRT = 1.19 | 0.05 | 0.04 |
| RRT = 1.28 | 0.02 | 0.00 |
| RRT = 1.37 | 0.02 | 0.03 |
| RRT = 1.62 | 0.00 | 0.06 |
| Total Impurities: | 0.3 | 0.34 |

RRT = RT of peak/RT of TA (RRT = Relative Retention Time, RT = Retention Time)
% Individual impurity = (Peak area of imp/Total peak area of K-40 sinus spacer) × 100
Total average peak area of K-40 sinus spacer at 0-day = 5869075
Total average peak area of K-40 sinus spacer at 30-day = 5233043
% Total impurities = (Total peak area of imp/Total peak area of K-40 sinus spacer) × 100
Only those impurity peaks ≥0.02% are considered significant impurities The Triamcinolone Acetonide potency of samples obtained from the Triamcinolone Acetonide loaded reservoir at days 0 and day 30, respectively, was confirmed by HPLC. In this study, the levels of impurities rose within acceptable ranges and the potency of Triamcinolone Acetonide present in the Triamcinolone Acetonide reservoir remained sufficient to cause the intended local anti-inflammatory effect for at least 30 days.

Efficacy of Triamcinolone Acetonide Delivered Using Substance Delivering Spacer Device 10

Use of topical corticosteroid therapy to treat chronic sinus inflammatory conditions is based on the rationale that more effective drug concentrations can be achieved at local receptor sites in the nasal mucosa, with minimal risk of systemic adverse effects. Triamcinolone Acetonide (TA) is a second generation synthetic corticosteroid of which there are currently six compounds approved for intranasal use. All six corticosteroids appear to be relatively equal with regard to potency and effectiveness. TA was chosen for use in the Ethmoid Sinus Spacer as the compound with the longest safety record and for its availability in a concentrated solution suitable for use in this device. Specifically, KENALOG-40 was used as it is one of the approved and marketed formulations of Triamcinolone Acetonide.

It has been established that intranasal and/or inhaled doses of Triamcinolone Acetonide do not cause hypothalamo-pituitary-adrenal (HPA) suppression even when drug is delivered for up to three years. See, Klossek J M et al., Local Safety Of Intranasal Triamcinolone Acetonide: Clinical And Histological Aspects Of Nasal Mucosa In The Long-Term Treatment Of Perennial Allergic Rhinitis, Rhinology, 39(1): 17-22 (2001); Lund, V J., Maximal Medical Therapy for Chronic Rhinosinusitis, Otolaryngol Clin N Am 38, 1301-1310 (2005) and Laliberte F et al., Clinical And Pathologic Methods To Assess The Long-Term Safety Or Nasal Corticosteroids, Allergy 55(8): 718-722 (2000).

Locally administered TA has been demonstrated to provide a reduction in the severity of both early and late phase reaction to allergens, reduced sensitivity of local nasal irritant receptors and reduced local inflammation and a decreased likelihood for secondary rhinovirus infections. Even long term local delivery of TA to the nasal sinus does not appear to damage nasal mucosa.

The volume of vehicle in the substance delivering spacer device 10 used in this study has a reservoir 14 that will hold 0.1 ml. when loaded to maximum capacity. If loaded to maximum capacity with the KENALOG-40, the reservoir will contain 4 mg of TA. This amount of TA is roughly equivalent in potency to the 35-40 mg of cortisol produced daily by normal human adrenal glands. Thus, a total 4 mg TA, even if released all at once, would not be expected to adversely affect adrenal corticoid activity.

As explained above, the openings 31 in the reservoir 14 of the substance delivering spacer device 10 may be designed to limit diffusion of TA from the reservoir so that only a small daily dose of drug is delivered over the course of two weeks. In this manner, the dose delivered locally into the ethmoids or other paranasal sinuses may be less than the recommended dose of TA delivered with commercially available nasal inhalers (e.g., NASACORT® Inhaler, Sanofi-Aventis, Bridgewater, N.J.).

Thirteen human subjects suffering from ethmoid sinusitis were treated by performance of a needle ethmoidotomy with post operative delivery of TA by implantation of a substance delivering spacer device 10 substantially as described above and shown in FIGS. 7A through 8J. Nine of these subjects were treated bilaterally and the remaining four unilaterally. Thus, twenty-two ethmoid sinuses were treated in total. A fourteenth patient suffering from frontal sinusitis was treated by a balloon dilation of the frontal outflow tract and with post operative delivery of TA by implantation of a substance delivering spacer device 10 substantially as described above and shown in FIGS. 8A through 8G.

Post-Operative Follow-Up and Data Collection
Subject Nos. 1-10:

Blood levels of TA were determined in subjects 1-10 prior to the administration of anesthesia and at 1, 2 and 4 hours following implantation and loading of the substance delivering spacer device 10. If the particular subject stayed overnight at the treatment facility, a blood sample was taken at 23 hours or just prior to discharge. Additional blood samples were collected in subjects 1-10 at 3, 7, 10 and 14 days after the procedure and immediately prior to explant and removal of the substance delivering spacer device 10.

In addition to collection of blood samples as noted above, the patient was asked to fill out a Sino-Nasal Outcomes Test (SNOT-20) questionnaire. (SNOT-20-Piccirillo, J F et al., Psychometric and clinimetric validity of the 20-Item Sino-Nasal Outcome Test (SNOT-20), Copyright© 1996 by Jay F. Piccirillo M. D., Washington University, St. Louis, Mo.) at baseline and at 1, 2 and 6 weeks following explant and removal of the substance delivering spacer device 10. Additionally, the patient was asked to fill out a questionnaire specific to the tolerability of the substance delivering spacer device 10. The device was removed during an office visit at day 14 following implantation. Quantification of residual drug in the device provided additional information relevant to the elution of triamcinolone acetonide from the Ethmoid Sinus Spacer during the implantation of the device.

Investigators provided post-operative care as required except no steroid nasal sprays and nasal rinses were administered. Post-operative antibiotic treatment was administered at the discretion of the Investigator, as needed. This was to minimize the effects of concomitant medications on the study outcome.

A final CT scan of the ethmoid sinuses was taken at eight weeks to assess the condition of the ethmoid sinuses and when compared to baseline, the degree of improvement.
Subject Nos. 11-13:

Subjects Nos. 11 through 13 received the same post-operative care and blood sample collection as Subject Nos. 1-10, with the following exceptions:

Following the baseline blood sample taken prior to the administration of anesthesia, blood was drawn at 4 hours following device implantation on the day of the procedure and days 1, (optional) 3, 7, 14, 21 and 28, prior to explant and removal of the substance delivering spacer device 10.

Six follow-up visits were scheduled throughout the study, at days 3, 7, 14, 21 and 28 and a final visit 10 weeks following the procedure. In addition to collection of blood samples as noted above, the patient was asked to fill out a SNOT-20 Quality of Life (QOL) questionnaire at baseline, and at 1, 2, and 6 weeks following explant. Additionally, the patient was asked to fill out a questionnaire specific to the tolerability of the Ethmoid Sinus Spacer. The device was removed during an office visit at day 28 following implantation.

Investigators provided post-operative care as required except no steroid nasal sprays were administered. Post-operative antibiotic treatment was administered at the discretion of the Investigator, as needed. This was to minimize the effects of concomitant medications on the study outcome.

Figure 15:
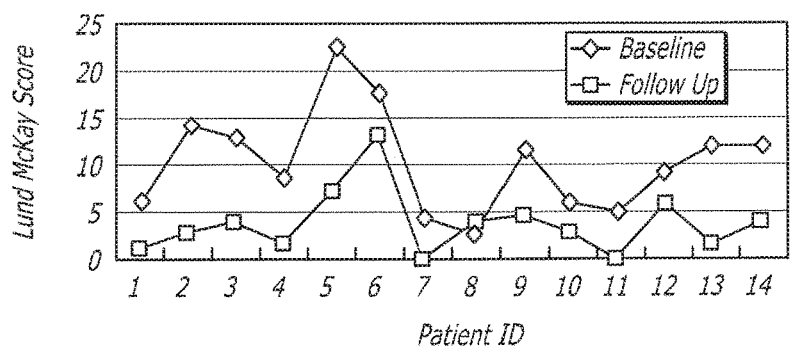
FIG. 15 is a graph showing Lund McKay Scores for 14 human subjects referred to below.
Figure 16:
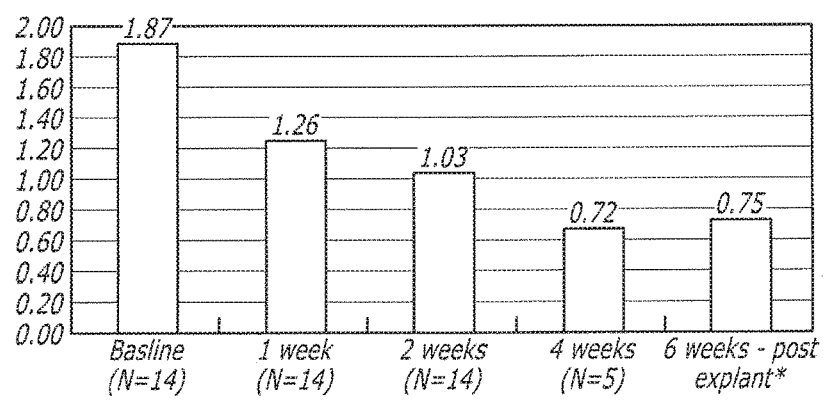
FIG. 16 is a bar graph showing the average SNOT 20 scores at various time points for human subjects referred to below.
Figure 17:
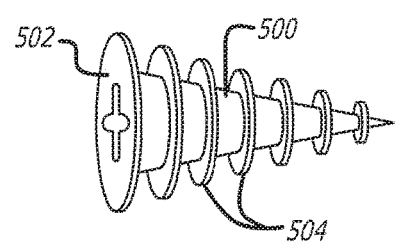
FIG. 17 is a perspective view of a substance delivering/bone penetrating screw device of the present invention.
Figure 17A:
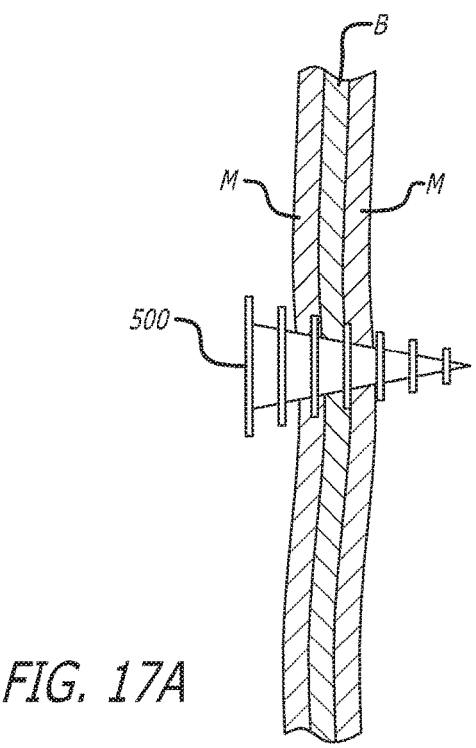
FIG. 17A is a diagram showing the substance delivering/bone penetrating screw device of FIG. 17 implanted in a bony intranasal structure covered with mucosal tissue.

A final CT scan of the ethmoid sinuses was taken at ten weeks (six weeks post explant) to assess the condition of the ethmoid sinuses and when compared to baseline, the degree of improvement.
Subject No. 14:

Subject No. 14 was the one who was treated for frontal sinusitis rather than ethmoid disease. Subject No. 14 received post-operative follow-up and data collection (e.g., blood samples and SNOT-20 questionaires) in substantially the same manner as Subject Nos. 1-10.
CT Scan Results The CT scans were read and improvement in the affected sinuses was scored by the Lund McKay scoring method. These Lund McKay Scores are shown graphically in FIG. 15. At baseline (pre-operative) the average Lund McKay Score was 10.4. The average Lund McKay score at follow-up 3.9. Thus, the 14 subjects studied exhibited an average reduction of 65.1% in Lund McKay score.
SNOT-20 and Questionnaire Results FIG. 16 shows the average improvement from baseline in the SNOT-20 scores as measured at 1, 2, 4, and 6 weeks (Note: One patient deviated from protocol and completed the 6 week follow-up visit at four weeks.) A score of 1.07 or below was deemed to be indicative of a clinically significant reduction of sinusitis symptoms (i.e., a reduction of at least 0.8 from the baseline SNOT 20 score). These data indicate that clinically significant reductions in the average SNOT 20 scores were observed at 2, 4 and 6 weeks after the procedure.

Symptom improvement was also documented in the Patient Questionnaire administered at one, two and six weeks post procedure. All patients reported they were significantly improved or improved six weeks following the procedure, no patients reported feeling worse. At six weeks a majority of patients were satisfied with the results and stated that if given this treatment choice again, they would agree to have the surgery.

Statistical Analysis of Results

The SNOT-20 results were recorded during 5 post-procedural evaluation visits. The null and alternative hypotheses evaluated based on this endpoint are as follows:

Ho: μ (Day 42 minus baseline)=0

Ha: μ (Day 42 minus baseline)≠0

Univariate analysis results from comparing the change in the SNOT-20 scores from baseline were analyzed using a paired-difference t-test. The results from this analysis revealed a significant reduction in the SNOT-20 scores within 7 days of the procedure. A consistent reduction was observed during all successive post-procedure evaluation visits. At the time enrollment was stopped, 13 of the 14 patients (92.9%) had completed the 42-day post-procedure evaluation visit. The reduction from baseline 42 days post-procedure was −22.08 points on the SNOT-20 scale, with a standard deviation of 14.69 and a probability value <0.001. The effect size of this result is 1.50, which is reflective of a very strong treatment effect.

Lund-McKay Scores (CT Scan)

CT scans were performed at baseline and 42 days following the procedure to derive the LMK score. The null and alternative hypotheses evaluated based on this endpoint are as follows:

Ho: μ (Day 42 minus baseline)=0

Ha: μ (Day 42 minus baseline)≠0

Univariate analysis results from comparing the change in the LMK scores from baseline were analyzed using a paired-difference t-test. The results from this analysis revealed a significant reduction in the LMK scores 42 days after the procedure. The reduction for baseline was 6.50 points on the LMK scale, with a standard deviation of 3.96, and a probability value <0.001. The effect size from this result is 1.64, which is reflective of a very strong treatment effect.

A subset analysis was performed comparing the change in the LMK scores from the ethmoid sinuses. The results from this analysis also revealed a significant reduction in the LMK scores 42 days after the procedure. The reduction for baseline was 2.21 points on the LMK scale, with a standard deviation 1.53, and a probability value <0.001. The effect size of this result is 1.44, which is reflective of a very strong treatment effect.

The primary efficacy endpoint was examined using inferential statistics. Based on the performance success of the 14 patients enrolled (100%), the lower 95% exact binomial confidence interval was 76.84%.

Blood Plasma Analysis

To assess the secondary endpoint of the ability of TA to elute from the substance delivering spacer device 10 to over time, TA concentrations were determined in blood plasma from each of the collected blood samples. These data are summarized in Table 2 below.

TABLE 2

Summary of Plasma/levels of TA at Different Time Points (measured in picograms per mL)

| Time of Plasma Sample Post Dose | # Patients Tested | # Patients Detected | Maximum Concentration Detected (pg/mL) | Average Amount (pg/mL) |
|---|---|---|---|---|
| 1 hr | 10 | 10 | 168 | 65.66 |
| 2 hr | 10 | 10 | 237 | 77.18 |
| 4 hour | 13 | 13 | 273 | 86.32 |
| 24 hour | 9 | 9 | 142 | 51.64 |
| 3 days | 14 | 13 | 82.1 | 26.65 |
| 7 days | 13 | 8 | 149 | 32.56 |
| 10 days | 10 | 5 | 86.5 | 33.30 |
| 14 days | 14 | 8 | 85 | 22.08 |
| 21 days | 3 | 3 | 15.8 | 10.88 |
| 28 days | 3 | 2 | 7.94 | 7.36 |

Low (i.e., not systemically active) but detectable TA levels were determined in the subjects' blood plasma as far out as 28 days following implantation and loading of the substance delivering spacer device 10.

CONCLUSION

Locally effective doses of TA were delivered from the substance delivering spacer device 10 for up to 28 days post-procedure. The CT scans indicated significant reduction in sinus inflammation. The subjects also realized substantial improvement in sinusitis symptoms on the basis of the SNOT 20 and patient questionnaire results.

The term substance as used herein is to be broadly construed to include any feasible drugs, prodrugs, proteins, gene therapy preparations, cells, diagnostic agents, contrast or imaging agents, biologicals, etc. Such substances may be in bound or free form, liquid or solid, colloid or other suspension, solution or may be in the form of a gas or other fluid or non-fluid. For example, in some applications where it is desired to treat or prevent a microbial infection, the substance delivered may comprise a pharmaceutically acceptable salt or dosage form of an antimicrobial agent (e.g., antibiotic, antiviral, antiparasitic, antifungal, etc.), a corticosteroid or other anti-inflammatory (e.g., an NSAID), a decongestant (e.g., vasoconstrictor), a mucous thinning agent (e.g., an expectorant or mucolytic), an agent that prevents or modifies an allergic response (e.g., an antihistamine, cytokine inhibitor, leucotriene inhibitor, IgE inhibitor, immunomodulator), an anesthetic agent with or without a vasoconstriction agents (e.g. Xylocaine with or without Epinephrine), an analgesic agent, an allergen or another substance that causes secretion of mucous by tissues, hemostatic agents to stop bleeding, anti-proliferative agents, cytotoxic agents e.g. alcohol, biological agents such as protein molecules, stem cells, genes or gene therapy preparations, viral vectors carrying proteins or nucleic acids such as DNA or mRNA coding for important therapeutic functions or substances, cauterizing agents e.g. silver nitrate, etc.

Some non-limiting examples of antimicrobial agents that may be used in this invention include acyclovir, amantadine, rimantadine, oseltamivir, zanamivir, aminoglycosides (e.g., amikacin, gentamicin and tobramycin), amoxicillin, amoxicillin/clavulanate, amphotericin B, ampicillin, ampicillin/sulbactam, atovaquone, azithromycin, cefazolin, cefepime, cefotaxime, cefotetan, cefpodoxime, ceftazidime, ceftizoxime, ceftriaxone, cefuroxime, cefuroxime axetil, cephalexin, chloramphenicol, clotrimazole, ciprofloxacin, clarithromycin, clindamycin, dapsone, dicloxacillin, doxycycline, erythromycin, fluconazole, foscarnet, ganciclovir, atifloxacin, imipenem/cilastatin, isoniazid, itraconazole, ketoconazole, metronidazole, nafcillin, nafcillin, nystatin, penicillins including penicillin G, pentamidine, piperacillin/tazobactam, rifampin, quinupristin-dalfopristin, ticarcillin/clavulanate, trimethoprim/sulfamethoxazole, valacyclovir, vancomycin, mafenide, silver sulfadiazine, mupirocin, nystatin, triamcinolone/nystatin, clotrimazole/betamethasone, clotrimazole, ketoconazole, butoconazole, miconazole, tioconazole, detergent-like chemicals that disrupt or disable microbes (e.g., nonoxynol-9, octoxynol-9, benzalkonium chloride, menfegol, and N-docasanol); chemicals that block microbial attachment to target cells and/or inhibits entry of infectious pathogens (e.g., sulphated and sulponated polymers such as PC-515 (carrageenan), Pro-2000, and Dextrin 2 Sulphate); antiretroviral agents (e.g., PMPA gel) that prevent retroviruses from replicating in the cells; genetically engineered or naturally occurring antibodies that combat pathogens such as anti-viral antibodies genetically engineered from plants known as "plantibodies;" agents which change the condition of the tissue to make it hostile to the pathogen (such as substances which alter mucosal pH (e.g., Buffer Gel and Acidform); non-pathogenic or "friendly" microbes that cause the production of hydrogen peroxide or other substances that kill or inhibit the growth of pathogenic microbes (e.g., *lactobacillus*); antimicrobial proteins or peptides such as those described in U.S. Pat. No. 6,716,813 (Lin et al.) which is expressly incorporated herein by reference or antimicrobial metals (e.g., colloidal silver).

Additionally or alternatively, in some applications where it is desired to treat or prevent inflammation the substances delivered in this invention may include various steroids or other anti-inflammatory agents (e.g., nonsteroidal anti-inflammatory agents or NSAIDs), analgesic agents or antipyretic agents. For example, corticosteroids that have previously administered by intranasal administration may be used, such as beclomethasone (VANCENASE® or BECONASE®, flunisolide (NASALIDE®), fluticasone proprionate (FLONASE®), triamcinolone acetonide (NASACORT®), budesonide (RHINOCORT AQUA®), loterednol etabonate (Locort) and mometasone (NASONEX®). Other salt forms of the aforementioned corticosteroids may also be used. Also, other non-limiting examples of steroids that may be useable in the present invention include but are not limited to aclometasone, desonide, hydrocortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone. Other anti-inflammatory, analgesic or antipyretic agents that may be used include the nonselective COX inhibitors (e.g., salicylic acid derivatives, aspirin, sodium salicylate, choline magnesium trisalicylate, salsalate, diflunisal, sulfasalazine and olsalazine; para-aminophenol derivatives such as acetaminophen; indole and indene acetic acids such as indomethacin and sulindac; heteroaryl acetic acids such as tolmetin, dicofenac and ketorolac; arylpropionic acids such as ibuprofen, naproxen, flurbiprofen, ketoprofen, fenoprofen and oxaprozin; anthranilic acids (fenamates) such as mefenamic acid and meloxicam; enolic acids such as the oxicams (piroxicam, meloxicam) and alkanones such as nabumetone) and Selective COX-2 Inhibitors (e.g., diaryl-substituted furanones such as rofecoxib; diaryl-substituted pyrazoles such as celecoxib; indole acetic acids such as etodolac and sulfonanilides such as nimesulide).

Additionally or alternatively, in some applications, such as those where it is desired to treat or prevent an allergic or immune response and/or cellular proliferation, the substances delivered in this invention may include a) various cytokine inhibitors such as humanized anti-cytokine antibodies, anti-cytokine receptor antibodies, recombinant (new cell resulting from genetic recombination) antagonists, or soluble receptors; b) various leucotriene modifiers such as zafirlukast, montelukast and zileuton; c) immunoglobulin E (IgE) inhibitors such as Omalizumab (an anti-IgE monoclonal antibody formerly called rhu Mab-E25) and secretory leukocyte protease inhibitor).

Additionally or alternatively, in some applications, such as those where it is desired to shrink mucosal tissue, cause decongestion or effect hemostasis, the substances delivered in this invention may include various vasoconstrictors for decongestant and or hemostatic purposes including but not limited to pseudoephedrine, xylometazoline, oxymetazoline, phenylephrine, epinephrine, etc.

Additionally or alternatively, in some applications, such as those where it is desired to facilitate the flow of mucous, the substances delivered in this invention may include various mucolytics or other agents that modify the viscosity or consistency of mucous or mucoid secretions, including but not limited to acetylcysteine (MUCOMYST®, MUCOSIL®) and guaifenesin.

Additionally or alternatively, in some applications such as those where it is desired to prevent or deter histamine release, the substances delivered in this invention may include various mast cell stabilizers or drugs which prevent the release of histamine such as cromolyn (e.g., NASAL CHROM®) and nedocromil.

Additionally or alternatively, in some applications such as those where it is desired to prevent or inhibit the effect of histamine, the substances delivered in this invention may include various antihistamines such as azelastine (e.g., ASTYLIN®), diphenhydramine, loratidine, etc.

Additionally or alternatively, in some embodiments such as those where it is desired to dissolve, degrade, cut, break or remodel bone or cartilage, the substances delivered in this invention may include substances that weaken or modify bone and/or cartilage to facilitate other procedures of this invention wherein bone or cartilage is remodeled, reshaped, broken or removed. One example of such an agent would be a calcium chelator such as EDTA that could be injected or delivered in a substance delivery implant next to a region of bone that is to be remodeled or modified. Another example would be a preparation consisting of or containing bone degrading cells such as osteoclasts. Other examples would include various enzymes of material that may soften or break down components of bone or cartilage such as collagenase (CGN), trypsin, trypsin/EDTA, hyaluronidase, and tosyllysylchloromethane (TLCM).

Additionally or alternatively, in some applications, the substances delivered in this invention may include other classes of substances that are used to treat rhinitis, nasal polyps, nasal inflammation, and other disorders of the ear, nose and throat including but not limited to anti-cholinergic agents that tend to dry up nasal secretions such as ipratropium (ATROVENT NASAL®), as well as other agents not listed here.

Additionally or alternatively, in some applications such as those where it is desired to draw fluid from polyps or edematous tissue, the substances delivered in this invention may include locally or topically acting diuretics such as furosemide and/or hyperosmolar agents such as sodium chloride gel or other salt preparations that draw water from tissue or substances that directly or indirectly change the osmolar content of the mucous to cause more water to exit the tissue to shrink the polyps directly at their site.

Additionally or alternatively, in some applications such as those wherein it is desired to treat a tumor or cancerous lesion, the substances delivered in this invention may include antitumor agents (e.g., cancer chemotherapeutic agents, biological response modifiers, vascularization inhibitors, hormone receptor blockers, cryotherapeutic agents or other agents that destroy or inhibit neoplasia or tumorigenesis) such as; alkylating agents or other agents which directly kill cancer cells by attacking their DNA (e.g., cyclophosphamide, isophosphamide), nitrosoureas or other agents which kill cancer cells by inhibiting changes necessary for cellular DNA repair (e.g., carmustine (BCNU) and lomustine (CCNU)), antimetabolites and other agents that block cancer cell growth by interfering with certain cell functions, usually DNA synthesis (e.g., 6 mercaptopurine and 5-fluorouracil (5FU), antitumor antibiotics and other compounds that act by binding or intercalating DNA and preventing RNA synthesis (e.g., doxorubicin, daunorubicin, epirubicin, idarubicin, mitomycin-C and bleomycin) plant (vinca) alkaloids and other anti-tumor agents derived from plants (e.g., vincristine and vinblastine), steroid hormones, hormone inhibitors, hormone receptor antagonists and other agents which affect the growth of hormone-responsive cancers (e.g., tamoxifen, herceptin, aromatase ingibitors such as aminoglutethamide and formestane, trriazole inhibitors such as letrozole and anastrazole, steroidal inhibitors such as exemestane), anti-angiogenic proteins, small molecules, gene therapies and/or other agents that inhibit angiogenesis or vascularization of tumors (e.g., meth-1, meth-2, thalidomide), bevacizumab (Avastin), squalamine, endostatin, angiostatin, Angiozyme, E-941 (Neovastat), CC-5013 (Revimid), medi-522 (Vitaxin), 2-methoxyestradiol (2ME2, Panzem), carboxyamidotriazole (CAI), combretastatin A4 prodrug (CA4P), SU6668, SU11248, BMS-275291, COL-3, EMD 121974, IMC-1C11, IM862, TNP-470, celecoxib (Celebrex), rofecoxib (Vioxx), interferon alpha, interleukin-12 (IL-12) or any of the compounds identified in Science Vol. 289, Pages 1197-1201 (Aug. 17, 2000) which is expressly incorporated herein by reference, biological response modifiers (e.g., interferon, bacillus calmette-guerin (BCG), monoclonal antibodies, interluken 2, granulocyte colony stimulating factor (GCSF), etc.), PGDF receptor antagonists, herceptin, asparaginase, busulphan, carboplatin, cisplatin, carmustine, cchlorambucil, cytarabine, dacarbazine, etoposide, flucarbazine, flurouracil, gemcitabine, hydroxyurea, ifosphamide, irinotecan, lomustine, melphalan, mercaptopurine, methotrexate, thioguanine, thiotepa, tomudex, topotecan, treosulfan, vinblastine, vincristine, mitoazitrone, oxaliplatin, procarbazine, streptocin, taxol, taxotere, analogs/congeners and derivatives of such compounds as well as other antitumor agents not listed here.

Additionally or alternatively, in some applications such as those where it is desired to grow new cells or to modify existing cells, the substances delivered in this invention may include cells (mucosal cells, fibroblasts, stem cells or genetically engineered cells) as well as genes and gene delivery vehicles like plasmids, adenoviral vectors or naked DNA, mRNA, etc. injected with genes that code for anti-inflammatory substances, etc., and, as mentioned above, osteoclasts that modify or soften bone when so desired.

Any of the devices and methods described herein may also be used to deliver substances to the brain or alter the functioning of the olfactory system. Such examples include, the delivery of energy or the deposition of devices and/or substances and/or substance delivering implant(s) to occlude or alter olfactory perception, to suppress appetite or otherwise treat obesity, epilepsy (e.g., barbiturates such as phenobarbital or mephoobarbital; iminostilbenes such as carbamazepine and oxcarbazepine; succinimides such as ethylsuximide; valproic acid; benzodiazepines such as clonazepam, clorazepate, diazepam and lorazepam, gabapentin, lamotrigine, acetazolamide, felbamate, levetiraceam, tiagabine, topiramate, zonisamide, etc.), personality or mental disorders (e.g., antidepressants, antianxiety agents, antipsychotics, etc.), chronic pain, Parkinson's disease (e.g., dopamine receptor agonists such as bromocriptine, pergolide, ropinitrol and pramipexole; dopamine precursors such as levodopa; COMT inhibitors such as tolcapone and entacapone; selegiline; muscarinic receptor antagonists such as trihexyphenidyl, benztropine and diphenhydramine) and Alzheimer's disease, Huntington's disease or other dementias, disorders of cognition or chronic degenerative diseases (e.g. tacrine, donepezil, rivastigmine, galantamine, fluoxetine, carbamazepine, clozapine, clonazepam and proteins or genetic therapies that inhibit the formation of beta-amyloid plaques), etc.

The devices and methods disclosed herein may be used to deliver several combinations of two or more substances disclosed herein to a suitable target anatomical region. In one particular embodiment, the devices and methods disclosed herein are used to deliver a combination of an anti-inflammatory agent (e.g. a steroid or an NSAID) and a mucolytic agent.

The devices and methods disclosed herein may be used to deliver gels or viscous liquids comprising one or more substances to anatomical regions such as paranasal sinuses. Such gels or viscous liquids may coat and adhere to a mucous membrane and thus provide sustained delivery of one or more substances to the mucous membrane. In one embodiment, a plasticized hydrocarbon gel comprising gelatin, pectin and sodium carboxymethylcellulose and a suitable substance may be delivered to a mucous membrane such as the mucous membrane of a paranasal sinus. Such gels can be used for sustained delivery of the suitable substance to the mucous membrane.

One or more of the substance reservoirs disclosed herein may comprise multiple compartments such that each compartment stores a particular substance formulation. The multiple compartments prevent mixing of multiple substance formulations before substance formulations are delivered to the anatomy.

One or more of the substance reservoirs comprising holes or pores may be filled with a suitable substance at a sufficiently high pressure to cause a portion of the substance to squirt out of the holes or pores. This process may be used to deliver an initial bolus of the substance to the surrounding anatomy.

One or more of the substance reservoirs disclosed herein may be filled with a suitable substance after the substance reservoir is introduced in an anatomical region. Alternatively, one or more of the substance reservoirs disclosed herein may be filled with a suitable substance before the substance reservoir is introduced in an anatomical region. Alternatively, one or more of the substance reservoirs disclosed herein may be pre-filled with a solid, lyophilized or concentrated substance. The solid, lyophilized or concentrated substance is converted to an active form by introducing a solvent into the substance reservoir. This may be done just before or after the substance reservoir is introduced in an anatomical region. Alternatively, one or more of the substance reservoirs disclosed herein may be pre-filled with an inactive form of a substance. The inactive form of the substance is converted to an active form by introducing an activating agent into the substance reservoir. This may be done just before or after the substance reservoir is introduced in an anatomical region.

It is to be further appreciated that, as described herein, the implantable portion of a substance delivering spacer device 10 may include a through lumen that may function as a vent and/or drain when such implantable portion device is in a paranasal sinus, air cell, Eustachian tube, opening formed in the tympanum or any other location within the body.

The devices and methods disclosed herein may be used to mark an anatomical region with a suitable imageable marker. For example, the devices and methods disclosed herein may be used to deliver a radio opaque marker such as a radio opaque contrast agent to an ostium of a paranasal sinus. This enables a user to image the ostium of the paranasal sinus using X-rays or fluoroscopy.

One or more of the substance delivery devices disclosed herein may comprise a curved, bent or angled region to enable the drug delivery devices to navigate through the anatomy.

The distal-most regions of one or more substance delivery devices disclosed herein may comprise an atraumatic tip. The atraumatic tip is used to prevent or reduce damage to the anatomy by the distal-most regions of the one or more substance delivery devices.

The outer surface of one of more substance delivery devices disclosed herein may comprise a coating that reduces or eliminates the risk of encrusting of the outer surface by a biological material. In one embodiment, the coating comprises a material that absorbs water to form a gel. Examples of such materials include, but are not limited to hyaluronic acid, etc.

One or more of the substance delivery devices disclosed herein may be designed to be easily removable from the anatomy after completion of a treatment.

One or more of the substance delivery devices disclosed herein may be refilled after a significant volume of substance filled in a substance reservoir has been delivered to the anatomy.

One or more of the substance delivery devices disclosed herein may comprise one or more markers to enable a user to locate and/or navigate the substance delivery devices through the anatomy. For example, the substance delivery devices may comprise visual markers to enable the user to determine the depth of insertion of the substance delivery devices into the anatomy. In another example, the substance delivery devices may comprise imaging markers to enable the user to locate and/or navigate the substance delivery devices using imaging modalities such as X-rays, MRI, etc.

As used herein, the term "opening of a paranasal sinus" shall include any opening in a paranasal sinus or air cell such as natural ostia, surgically altered natural ostia, surgically created openings, antrostomy openings, ostiotomy openings, burr holes, drilled holes, ethmoidotomy openings, ethmoidectomy openings, natural or man made passageways, etc.

As used herein, the term "implantable" shall include any device that is maintained in the body of a human or animal for a period ranging from 30 minutes to 60 days.

In each of the above-described examples wherein an endoscope 400 is employed, the endoscope 400 is shown as being inserted separately form the other devices. However, in any applications or embodiments of the invention where feasible, an endoscope may be attached to or integrated with one or more of the other devices used during the procedure as described in parent applications.

It is to be appreciated that Examples 2 and 3 above describe techniques which may be used for introducing the spacer device 10 into frontal sinuses which may or may not have been previously altered by surgery or prior balloon dilations. In some cases, such as where the frontal outflow tract has been previously dilated or modified by surgery so that the frontal sinus FS is relatively easy to access, the operator may simply deliver the spacer device 10 through the constraining tube 42 (or sinus sheath 40, 40*a*) and into the frontal sinus, with or without the use of forceps or other operative instruments, thereby eliminating the need for the use of a guide catheter, guidewire, dilator or other devices for guiding or facilitating advancement of the spacer device 10 into the frontal sinus as described in Examples 2 and 3.

It is to be further appreciated that, although Examples 1, 2 and 3 above describe Triamcinolone Acetonide injectable suspension (KENALOG® 40, Brystol-Myers Squibb Company, Princeton, N.J.) as the therapeutic agent that is loaded into and elutes from the reservoir, various other therapeutic agents may be used in addition to, or as an alternative to, this Triamcinolone Acetonideq injectable suspension. In some cases where it is desired to use the implanted spacer device 10*a* to deliver a steroid, the steroid may be prepared as a solution rather than a suspension. In such cases, the steroid will be dissolved in a suitable, biologically compatible solvent. For example, Cyclodextrins have been described as suitable solvents for dissolution of at least some steroids. Khomutov, S. M., Dovbnya, D. V. and Donova, M. V., Dissolution of a Mixture of Steroids in Cyclodextrin Solutions: a Model Description; Pharmaceutical Chemistry Journal; Vol. 35, No. 1i, pp. 627-629 (November, 2001).

In some instances, the devices of the present invention may be used to deliver steroids or other substances in formulations that are commercially available as, or otherwise suitable for, intra-nasal delivery to the nasal mucosa as nasal drops or sprays (i.e., nasal solutions). In at least some cases, such nasal solutions are prepared so that they are similar to nasal secretions and, thus, do not interfere with normal ciliary action. Such nasal solutions usually are isotonic and slightly buffered to a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics, steroids, antihistamines, decongestants and ipitropium bromide.

Where possible and appropriate, any of the substances delivered by devices of the present invention may be in the form of liposomes or nanoparticles (e.g., nanocapsules). The formation and use of liposomes is generally known to those of skill in the art. Liposomes are formed from phospholipids dispersed in an aqueous medium such that they spontaneously form multilamellar concentric bilayer vesicles sometimes referred to as multilamellar vesicles (MLVs). MLVs are typically from 25 nm to 4 μm in diameter. When sonicated, MLVs form small unilamellar vesicles (SUVs) of about 200 to 500 angstroms in diameters having cores which contain the aqueous solution. In general, when dispersed in an aqueous medium, phospholipids can form various structures other than liposomes, depending on the molar ratio of lipid to water. At low molar lipid to water ratios, liposomes will form. The physical characteristics of liposomes depend on pH, tonicity and the presence or non-presence of divalent cations. Liposomes can interact with cells by different mechanisms, including 1) endocytosis (e.g., phagocytosis of the liposome by cells such as macrophages and neutrophils), adsorption to the cell surface, 2) interaction with cell-surface components, 3) fusion with the plasma cell membrane by insertion of the lipid bilayer of the liposome into the plasma membrane or 4) transfer of liposomal lipids to cellular or subcellular membranes, or vice versa. Varying the liposome formulation can alter which mechanism(s) by which the lyposomes will interact with cells in the paranasal sinus, nasal mucosa, etc.

A nanocapsule is any nanoparticle that consists of a shell and a space, in which desired substances may be placed. Techniques for forming nanocapsules are known in the art. Polymeric nanocapsules can be made in specific sizes and shapes. They can be produced as monodisperse particles which have precisely defined physical and chemical properties and, thus, can be tailored to facilitate release of the therapeutic or diagnostic substance in response to particular bimolecular triggering mechanisms, such as pH, mucous flow or other conditions present within the paranasal sinus or other area in the ear, nose or throat where the device is implanted. Nanocapsules can be used in the present invention as "smart drugs" which have specific chemical receptors or binding sites that will bind to specific target cells (e.g., cancer cells associated with sinus or nasal tumors or cells associated with inflammatory conditions).

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed:

1. A system comprising:
   (a) a tubular guide device configured to extend through a nostril to position a distal end of the guide device in or near an ostium of a paranasal sinus while a proximal end of the guide device is located outside of the nostril;
   (b) a substance delivery device configured to be received within the guide device, wherein at least a distal portion of the substance delivery device is configured to fit within the paranasal sinus ostium, wherein the substance delivery device comprises:
      (i) an elongate tubular shaft having a lumen,
      (ii) an expandable reservoir arranged on a distal portion of the tubular shaft, wherein the expandable reservoir is configured to expand and emit a substance therefrom after the substance delivery device has been positioned in the paranasal sinus ostium, and
      (iii) a retention member, wherein the retention member is transitionable between a collapsed state and an expanded state in which the retention member is configured to engage tissue and thereby maintain a position of the substance delivery device relative to the paranasal sinus ostium, wherein the retention member is biased toward the expanded state; and
   (c) a sheath slidably disposed over the substance delivery device, wherein the sheath is configured to selectively hold the retention member in the collapsed state and release the retention member into the expanded state, wherein the sheath includes a stop member configured to abut a portion of the guide device to thereby limit distal translation of the sheath relative to the guide device while permitting distal translation of the substance delivery device through the sheath.

2. The system of claim 1, wherein the distal portion of the tubular shaft includes an aperture configured to establish fluid communication between the lumen and an interior of the expandable reservoir, wherein the substance delivery device further comprises a one-way valve arranged at the aperture.

3. The system of claim 2, wherein the one-way valve comprises an elastomeric sleeve valve that encircles the distal portion of the tubular shaft containing the aperture.

4. The system of claim 2, wherein the expandable reservoir encircles the distal portion of the tubular shaft containing the one-way valve and the aperture.

5. The system of claim 1, wherein the substance delivery device further comprises a first radiopaque marker arranged at a proximal end of the expandable reservoir and a second radiopaque marker arranged at a distal end of the expandable reservoir, wherein the radiopaque markers are configured to facilitate positioning of the expandable reservoir within the paranasal sinus ostium.

6. The system of claim 1, wherein the retention member is resiliently biased toward the expanded state.

7. The system of claim 1, wherein the retention member is configured to extend distally alongside at least a portion of the expandable reservoir when in the expanded state.

8. The system of claim 1, wherein the retention member comprises a looped wing.

9. The system of claim 1, wherein the sheath is slidably disposed within the guide device.

10. The system of claim 1, wherein an outer wall of the expandable reservoir includes a plurality of openings configured to emit the substance from an interior of the expandable reservoir.

11. The system of claim 10, wherein the expandable reservoir includes a tapered proximal end, a tapered distal end, and a cylindrical side wall extending therebetween, wherein the openings are formed in at least the cylindrical side wall.

12. The system of claim 10, wherein each of the openings has a diameter of about 20 microns to about 40 microns.

13. The system of claim 1, wherein the substance delivery device further includes a shaft marker arranged on the tubular shaft proximally of the expandable reservoir, wherein a longitudinal position of the shaft marker relative to the stop member of the sheath is configured to inform a user of a longitudinal position of the expandable reservoir relative to a distal end of the guide device.

14. The system of claim 1, wherein the tubular shaft includes a severable portion arranged between a proximal portion of the tubular shaft and the distal portion of the tubular shaft, wherein the severable portion is configured to be severed to separate the proximal and distal portions after positioning of the expandable reservoir within the paranasal sinus ostium.

15. The system of claim 1, wherein the guide device includes a deformable distal portion configured to assume a curved shape.

16. The system of claim 1, wherein the substance delivery device further includes a suture loop coupled to the tubular shaft, wherein the suture loop is configured to facilitate attachment of the substance delivery device to a nasal cavity or a frontal sinus outflow tract.

17. A system comprising:
(a) a guide device configured to extend through a nostril to position a distal end of the guide device in or near an ostium of a paranasal sinus while a proximal end of the guide device is located outside of the nostril;
(b) a substance delivery device slidable within the guide device, wherein at least a distal portion of the substance delivery device is configured to fit within the paranasal sinus ostium, wherein the substance delivery device comprises:
(i) a shaft having a lumen,
(ii) an expandable reservoir arranged on a distal portion of the shaft, wherein the expandable reservoir is configured to expand and emit a substance therefrom after the substance delivery device has been positioned in the paranasal sinus ostium, and
(iii) a retention member, wherein the retention member is transitionable between a collapsed state and an expanded state in which the retention member is configured to engage tissue and thereby maintain a position of the substance delivery device relative to the paranasal sinus ostium, wherein the retention member is biased toward the expanded state; and
(c) a constraint device movable relative to the guide device, wherein the constraint device is moveable relative to the substance delivery device between a first position in which the constraint device constrains the retention member in the collapsed state, and a second position in which the constraint device releases the retention member into the expanded state, wherein a portion of the constraint device is configured to engage the guide device to thereby limit movement of the constraint device relative to the guide device while permitting translation of the substance delivery device relative to the constraint device.

18. The system of claim 17, wherein the constraint device comprises a sheath slidably disposed over the substance delivery device.

19. A system comprising:
(a) a guide device configured to extend through a nostril to position a distal end of the guide device in or near an ostium of a paranasal sinus while a proximal end of the guide device is located outside of the nostril;
(b) a substance delivery device slidable within the guide device, wherein at least a distal portion of the substance delivery device is configured to fit within the paranasal sinus ostium, wherein the substance delivery device comprises:
(i) a shaft having a shaft lumen,
(ii) an inflatable member provided on a distal shaft portion of the shaft, wherein the inflatable member includes a plurality of openings that fluidly communicate with the shaft lumen,
wherein the inflatable member is configured to inflate with the substance and emit the substance through the openings, and
(iii) a retention member coupled to the shaft, wherein the retention member is transitionable between a collapsed state and an expanded state independently of inflation of the inflatable member, wherein in the expanded state the retention member is configured to engage tissue and thereby maintain a position of the substance delivery device relative to the paranasal sinus ostium; and,
(c) a constraint device operatively coupled with the guide device and the substance delivery device,
wherein the system is actuatable through a first range of motion in which the substance delivery device and the constraint device translate distally relative to the guide device, wherein the constraint device is configured to constrain the retention member in the collapsed state throughout the first range of motion,
wherein the system is further actuatable through a second range of motion in which the substance delivery device translates distally relative to the constraint device and the guide device, wherein the constraint device is configured to disengage the retention member and permit expansion thereof toward the expanded state in response to actuation of the system through the second range of motion.

20. The system of claim 19, wherein the retention member comprises a looped wing.

* * * * *